US008666718B2

(12) United States Patent
Lawrence et al.

(10) Patent No.: US 8,666,718 B2
(45) Date of Patent: Mar. 4, 2014

(54) STRUCTURE OF THE C-TERMINAL REGION OF THE INSULIN RECEPTOR α-CHAIN AND OF THE INSULIN-LIKE GROWTH FACTOR RECEPTOR α-CHAIN

(75) Inventors: Michael Colin Lawrence, Melbourne (AU); Brian John Smith, Melbourne (AU); John Gerbrandt Tasman Menting, Melbourne (AU); Colin Wesley Ward, Melbourne (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 0 days.

(21) Appl. No.: 13/265,879

(22) PCT Filed: Mar. 9, 2010

(86) PCT No.: PCT/AU2010/000271
§ 371 (c)(1),
(2), (4) Date: Oct. 24, 2011

(87) PCT Pub. No.: WO2010/121288
PCT Pub. Date: Oct. 28, 2010

(65) Prior Publication Data
US 2012/0122771 A1     May 17, 2012

Related U.S. Application Data

(60) Provisional application No. 61/214,472, filed on Apr. 22, 2009.

(51) Int. Cl.
*G01N 33/48* (2006.01)
*G06G 7/58* (2006.01)

(52) U.S. Cl.
USPC ................................ 703/11; 702/19; 530/350

(58) Field of Classification Search
None
See application file for complete search history.

(56) References Cited

PUBLICATIONS

Lawrence et al. Current Opinion in Structural Biology, vol. 17, Issue 6, 2007, pp. 699-705.*
Lou et al. PNAS, 2006, vol. 103, No. 33, 12429-12434.*
McKern, N.M. et al (2006) Nature, 443:218-221.*
Ward et al., "Ligand-induced activation of the insulin receptor: a multi-step process involving structural changes in both the ligand and the receptor", BioEssays, 2009, vol. 31, pp. 422-434.
Weiner et al., "A new force field for molecular mechanical simulation of nucleic acids and proteins", J Am Chem Soc, 1984, vol. 106, No. 765-784.
Yin et al., "Terphenyl-based helical mimetics that disrupt the p53/HDM2 interaction", Angew Chem Int Ed, 2005, vol. 44, pp. 2704-2707.
Yip et al., "Localization of the insulin-binding site to the cysteine-rich region of the insulin receptor a-subunit", Biochemical and Biophysical Research Communications, 1988, vol. 157, No. 1, pp. 321-329.
Yip et al., "Three-dimensional structural interactions of insulin and its receptor", Journal of Biological Chemistry, 2003, vol. 278, No. 30, pp. 27329-27332.
Zuckermann et al., "Discovery of nanomolar ligands for 7-transmembrane G-protein-coupled receptors from a diverse N-(Substituted) glycine peptoid library", J Med Chem, 1994, vol. 37, pp. 2678-2685.
Jones, "Improved methods for building protein models in electron density maps and the location of errors in these models", Acta Cryst, 1991, vol. A47, pp. 110-119.
Jones, "Interactive electron-density map interpretation: from INTER to O", Acta Cryst, 2004, vol. D60, pp. 2115-2125.
Jorgensen et al., "The OPLS potential functions for proteins. Energy minimizations for crystals of cyclic peptides and crambin", Journal of the American Chemical Society, 1988, vol. 110, pp. 1657-1666.
Kabsch, "Automatic processing of rotation diffraction data from crystals of initially unknown symmetry and cell constants", J Appl Cryst, 1993, vol. 26, pp. 795-800.
Kiselyov et al., "Harmonic oscillator model of the insulin and IGF1 receptors' allosteric binding and activation", Mol Sys Biol, 2009, vol. 5, No. 243, p. 1-12.
Kitamura et al, "Insulin receptor knockout mice", Annu Rev Physiol, 2003, vol. 65, pp. 313-332.
Kuntz et al., "A geometric approach to macromolecule-ligand interactions", J Mol Biol, 1982, vol. 161, pp. 269-288.
Kurose et al., "Cross-linking of a B25 azidophenylalanine insulin derivative to the carboxyl-terminal region of the a-subunit of the insulin receptor", J Biol Chem, 1994, vol. 269, No. 46, pp. 29190-29197.
Lam et al., "A new type of synthetic peptide library for identifying ligand-binding activity", Nature, 1991, vol. 354, pp. 82-84.
Lawrence et al., "Shape complementarity at protein/protein interfaces", J Mol Biol, 1993, vol. 234, pp. 946-950.
Lawrence et al., "Insulin receptor structure and its implications for the IGF-1 receptor", Current Opinion in Structural Biology, 2007, vol. 17, pp. 699-705.
Liu et al., Mice carrying null mutations of the genes encoding insulin-like growth factor 1 (Igf-1) and type1 IGF receptor (Igf1r 993), Cell, vol. 75, pp. 59-72.
Lou et al., "The first three domains of the insulin receptor differ structurally from the insulin-like growth factor 1 receptor in the regions governing ligand specificity", Proc Nat Acad Sci, 2006, vol. 103, No. 33, pp. 12429-12434.
Lou et al., "Quaternary structure of the insulin-insulin receptor complex", Science, 1999, vol. 285, pp. 1077-1080.
Marsh et al., "Molecular regulations of GLUT-4 targeting in 3T3-L1 adipocytes", The Journal of Cell Biology, 1995, vol. 130, No. 5, pp. 1081-1091.
Martin, "3D database searching in drug design", Journal of Medicinal Chemistry, 1992, vol. 35, No. 12, pp. 2145-2154.
McCoy, "Solving structures of protein complexes by molecular replacement with Phaser", Acta Cryst, 2007, Vol D63, pp. 32-41.
McKern et al., "Structure of the insulin receptor ectodomain reveals a folded-over conformation", Nature, 2006, vol. 443, pp. 218-221.

(Continued)

*Primary Examiner* — Michael Borin
(74) *Attorney, Agent, or Firm* — Klauber & Jackson LLC

(57) ABSTRACT

The present invention relates generally to structural studies of the insulin binding site of the insulin receptor (IR) and the insulin-like growth factor 1 receptor (IGF-1R). More particularly, the present invention relates to the crystal structure of the low affinity insulin binding site of the IR ectodomain comprising the C-terminal region of the IR α-chain, as well as the corresponding region of IGF-1R, and to methods of using the crystal and related structural information to screen for and design compounds that interact with or modulate the function of IR and/or IGF-1R.

11 Claims, 12 Drawing Sheets

(56) References Cited

PUBLICATIONS

Figure 1:
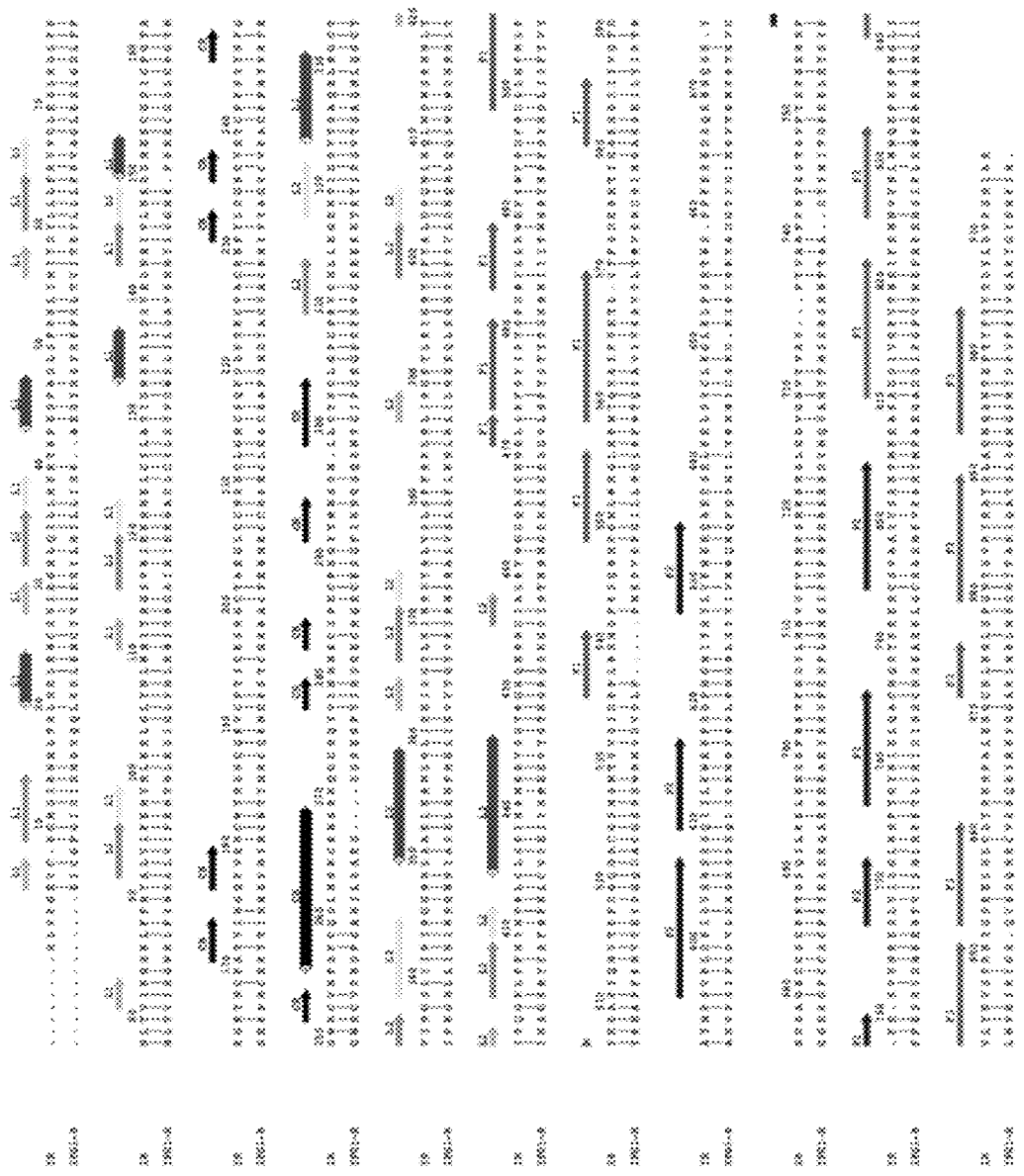

Menting et al., "A thermodynamic study of ligand binding to the first three domains of the human insulin receptor: relationship between the receptor a-chain C-terminal peptide and the site1 insulin mimetic peptides", Biochemistry, 2009, vol. 48, pp. 5492-5500.

Miranker et al., "Functionality maps of binding sites: a multiple copy simultaneous search method", Proteins: structure, function, and genetics, 1991, vol. 11, 29-34.

Moody et al., "A simple free fat cell biassay for insulin", Horm Metab Res, 1974, vol. 6, pp. 12-16.

Morton et a., "Kinetic analysis of macromolecular interactions using surface plasmon resonance biosensors", Methods in Enzymology, 1998, vol. 295, vol. 268-294.

Navaza et al., "AMoRe: An automated molecular replacement program package", Methods in Enzymology, 1997, vol. 276, pp. 581-594.

Navia et al., "Use of structural information in drug design", Curr Opinion in Structural Biology, 1992, vol. 2, pp. 202-210.

Nice et al., "Instrumental biosensors: new perspectives for the analysis of biomolecular interactions", Bioessays, 1999, vol. 21, pp. 339-352.

Olefsky, "Mechanisms of the ability of insulin to activate the glucose-transport systems in rat adipocytes", Biochem J., 1978, vol. 172, pp. 137-145.

Ottensmeyer et al., "Mechanism of transmembrane signaling: insulin binding and the insulin receptor", Biochemistry, 2000, vol. 39, No. 40, pp. 12103-12112.

Ottensmeyer et al., "Mechanism of transmembrane signaling: insulin binding and the insulin receptor", Biochemistry, 2001, vol. 40, p. 6988.

Pflugrath, "The finer things in X-ray diffraction data collection", Acta Cryst, 1999, vol. D55, pp. 1718-1725.

Pillutla et al., "Peptides identify the critical hotspots involved in the biological activation of the insulin receptor", J Biol Chem, 2002, vol. 277, No. 25, pp. 22590-22594.

Rarey et al., "A fast flexible docking method using an incremental construction algorithm", J Mol Biol, 1996, vol. 261, pp. 470-489.

Robinson et al., "Insulin-regulated sorting of glucose transporters in 3T3-L1 adipocytes", Am J Physiol, 1992, vol. 263, pp. E383-E393.

Sali et al., "Comparative protein modelling by satisfaction of spatial restraints", J Mol Biol, 1993, vol. 234, pp. 779-815.

Schaffer, "A model for insulin binding to the insulin receptor", Eur J Biochem, 1994, vol. 221, pp. 1127-1132.

Schaffer et al., "Assembly of high-affinity insulin receptor agonists and antagonists from peptide building blocks", Proc Natl Acad Sci, 2003, vol. 100, pp. 4435-4439.

Scott et al., "Searching for peptide ligands with an epitope library", Science, 1990, vol. 249, pp. 386-390.

Silverman et al., "Multivalent avimer proteins evolved by exon shuffling of a family of human receptor domains", Nature Biotech, 2005, vol. 23, No. 12, pp. 1556-1561.

Smith et al., "Regulation of vascular endothelial growth factor-dependent retinal neovascularizatoin by insulin-like growth factor-1 receptor", Nat Med, 1999, vol. 5, pp. 1390-1395.

Songyang et al., "SH2 domains recognize specific phosphopeptide sequences", Cell, 1993, vol. 72, pp. 767-778.

Sparrow et al., "The disulfide bonds in the C-terminal domains of the human insulin receptor ectodomain", J Biol Chem, 1997, vol. 272, No. 47, pp. 29460-29467.

Surinya et al., "An investigation of the ligand binding properties and negative cooperativity of soluble insulin-like growth factor receptors", J Biol Chem, 2008, vol. 283, pp. 5355-5363.

Svenson et al., "Altered activity and physicochemical properties of short cationic antimicrobial peptides by incorporation of arginine analogues", Molecular Pharmaceutics, 2009, vol. 6, No. 3, pp. 996-1005.

Tong et al., "Rotation function calculations with GLRF program", Methods in Enzymology, 1997, vol. 276, pp. 594-611.

Totrov et al., "Flexible ligand docking to multiple receptor conformations: a practical alternative", Current Opinion in Structural Biology, 2008, vol. 18, pp. 178-184.

Tulloch et al., "Single-molecule imaging of human insulin receptor ectodomain and its fab complexes", Journal of Structural Biology, 1999, vol. 125, pp. 11-18.

Ullrich et al., "Human insulin receptor and its relationship to the tyrosine kinase family of oncogenes", Nature, 1985, vol. 313, pp. 756-761.

Ullrich et al., "Insulin-like growth factor I receptor primary structure: comparison with insulin receptor suggests structural determinants that define functionality specificity", The EMBO Journal, 1986, vol. 5, No. 10, pp. 2503-2512.

Ulrich, "RNA aptamers: from basic science towards therapy", Handbook Exp Pharmacol, 2006, vol. 173, pp. 305-326.

Van Der Spoel et al., "GROMACS: fast, flexible, and free", J Comp Chem, 2005, vol. 26, pp. 1701-1718.

Wada et al., "New twist on neuronal insulin receptor signaling in health, disease and therapeutics", J Pharmacol Sci, 2005, vol. 99, pp. 128-143.

Hewish et al., "Insulin-like growth factor 1 receptor targeted therapeutics: novel compounds and novel treatment strategies for cancer medicine", Recent Patents on Anti-Cancer Drug Discovery, 2009, vol. 4, pp. 54-72.

Houghten et al., "The use of synthetic peptide combinatorial libraries for the identification of bioactive peptides", BioTechniques, 1992, vol. 13, No. 3, pp. 412-421.

Kristensen et al., "Functional reconstitution of insulin receptor binding site from non-binding receptor fragments", J Biol Chem, 2002, vol. 277, No. 21, pp. 18340-18345.

Lam, "Application of combinatorial library methods in cancer research and drug discovery", Anti-Cancer Drug Design, 1997, vol. 12, pp. 145-167.

Stumpp et al., "DARPins: a true alternative to antibodies", Current Opinion Drug Discovery & Development, 2007, vol. 10, No. 2, pp. 153-159.

Adams et al., "Structure and function of the type 1 insulin-like growth factor receptor", Cell. Mol. Life Sci., 2000, vol. 57, pp. 1050-1093.

Adams et al., "PHENIX: Building new software for automated crystallographic structure determination", Acta Crysta, 2002, vol. D58, pp. 1948-1954.

Apfel, "Neurotrophic factors in the therapy of diabetic neuropathy", Am J Med, 1999, vol. 107, pp. 34S-42S.

Auer, "Insulin, blood glucose levels, and ischemic brain damage", Neurology, 1998, vol. 51, pp. S39-S43.

Bailyes et al., "Insulin receptor/IGF-I receptor hybrids are widely distributed in mammalian tissues: quantification of individual receptor species by selective immunoprecipitation and immunoblotting", Biochem J, 1997, vol. 327, pp. 209-215.

Bartlett et al., "CAVEAT: A program to facilitate the structure-derived design of biologically active molecules", Royal, Royal Chem Soc, 1989, vol. 78, pp. 182-196.

Bentley, "Phased translation function", Methods in Enzymology, 1997, vol. 276, pp. 611-619.

Binz et al., "Engineering novel binding proteins from nonimmunoglobulin domains", Nature Biotechnology, 2005, vol. 23, No. 10, pp. 1257-1268.

Blondelle et al., "Novel antimicrobial compounds identified using synthetic combinatorial library technology", Trends Biotechnol, 1996, vol. 14, pp. 60-65.

Bohm et al., "Rapid Empirical scoring functions in virtual screening applications", Med Chem Res, 1999, vol. 9, pp. 445-462.

Brooks et al., "CHARMM: A program for macromolecular energy, minimizaton, and dynamics calculations", Journal of Computational Chemistry, 1983, vol. 4, No. 2, pp. 187-217.

Brunger, "Patterson correlation searches and refinement", Methods in Enzymology, 1997, vol. 276, pp. 558-580.

Brunger et al., "Crystallography & NMR system: A new software suite for macromolecular structure determination", Acta Cryst, 1998, vol. D54, pp. 905-921.

Brunger et al., "X-ray structure determination at low resolution", Acta Cryst, 2009, vol. D65, pp. 128-133.

(56) References Cited

OTHER PUBLICATIONS

Bruns et al., "Human glutathione transferase A4-4 crystal structures and mutagenesis reveal the basis of high catalytic efficiency with toxic lipid peroxidation products", J Mol Biol, 1999, vol. 288, pp. 427-439.

Bussi et al., "Canonical sampling through velocity rescaling", The Journal of Chemical Physics, 2007, vol. 126, pp. 14101-1 thru 14101-7.

Butt et al., "The IGF axis and programmed cell death", Immunology and Cell Biology, 1999, vol. 77, pp. 256-262.

Carell et al., "A novel procedure for the synthesis of libraries containing small organic molecules", Angew Chem Int Ed Engl, 1994, vol. 33, No. 20, p. 2059-2060.

Carell et al., "A solution-phase screening procedure for the isolation of active compounds from a library of molecules", Angew Chem Int Ed Engl, 1994, vol. 33, No. 20, p. 2060-2061.

Cho et al., "An unnatural biopolymer", Science, 1993, vol. 261, pp. 1303-1305.

Chow et al., "Insulin-like growth factor-I receptor internalizaton regulates signaling via the Shc/Mitogen-activated protein kinase pathway, but not the insulin receptor substrate-1 pathway", Journal of Biological Chemistry, 1998, vol. 273, No. 8, pp. 4672-4680.

Clarke et al., "In vivo biodistribution of a humanized anti-lewis Y monoclonal antibody (hu3S193) in MCF-7 xenografted BALB/c nude mice", Cancer Research, 2000, vol. 60, pp. 4804-4811.

Cohen et al., "Molecular modeling software and methods for medicinal chemistry", Journal of Medicinal Chemistry, 1990, vol. 33, No. 3, pp. 883-894.

Cull et al., "Screening for receptor ligands using large libraries of peptides linked to the C terminus of the lac repressor", Proc Natl Acad Sci, 1992, vol. 89, pp. 1865-1869.

Cwirla e a., "Peptides on phage: A vast library of peptides for identifying ligands", Proc Natl Acad Sci, 1990, vol. 87, pp. 6378-6382.

Danial et al., "Dual role of proapoptotic BAD in insulin secretion and beta cell survival", Nature Medicine, 2008, vol. 14, No. 2, pp. 144-153.

Davis et al., "Synthetic non-peptide mimetics of a-helices", Chemical Society Reviews, 2007, vol. 36, pp. 326-334.

Dey et al., "Fragment-based de novo ligand design by multiobjective evolutionary optimization", J Chem Inf Model, 2008, vol. 48, No. 679-690.

Degterev et al, "Identification of small-molecule inhbitors of interaction between the BH3 domain and Bcl-xl", Nat Cell Biology, 2001, vol. 3, pp. 173-182.

De Meyts, "The structural basis of insulin and insulin-like growth factor-I receptor binding and negative co-operativity, and its relevance to mitogenic versus metabolic signalling", Diabetologia, 1994, vol. 37, pp. 135-148.

De Meyts et al., "Structural biology of insulin and IGF1 receptors: implications for drug design", Nature Reviews Drug Discovery, 2002, vol. 1, pp. 769-783.

De Meyts, "Insulin and its receptor: structure, function and evolution", BioEssays, 2004, vol. 26, No. 1351-1362.

Denley et al., "The insulin receptor isoform Exon 11-(IR-A) in cancer and other diseases: a review", Horm Metab Res, 2003, vol. 35, pp. 778-785.

Denley et al., "Structural determinants for high-affinity binding of insulin-like growth factor II to insulin receptor (IR)-A, the Exon 11 minus isoform of the IR", Molecular Endocrinology, 2004, vol. 18, No. 10, pp. 2502-2512.

Devlin et al, "Random peptide libraries: A source of specific protein binding molecules", Science, 1990, vol. 249, pp. 404-406.

Dewitt et al., "Diversomers: An approach to nonpeptide, nonoligomeric chemical diversity", Proc Natl Acad Sci, 1993, vol. 90, pp. 6909-6913.

Eramian et al., "A composite score for predicting errors in protein structure models", Protein Science, 2006, vol. 15, pp. 1653-1666.

Erb et al., "Recursive deconvolution of combinatorial chemical libraries", Proc Natl Acad Sci, 1994, vol. 91, pp. 11422-11426.

Ernst et al., "Changes in cerebral metabolism are detected prior to perfusion changes in early HIV-CMC: a coregistered 1H MRS and SPECT study", Journal of Magnetic Resonance Imaging, 2000, vol. 12, pp. 859-865.

Ewing, "DOCK 4.0: search strategies for automated molecular docking of flexible molecule databases", Journal of Computer-Aided Molecular Design, 2001, vol. 15, pp. 411-428.

Felici, "Selection of antibody ligands from a large library of oligopeptides expressed on a multivalent exposition vector", J Mol Biol, 1991, vol. 222, pp. 301-310.

Fodor, "Multiplexed biochemical assays with biological chips", Nature, 1993, vol. 364, pp. 555-556.

Friesner et al., "Glide: A new approach for rapid, accurate docking and scoring. 1. method and assessment of docking accuracy", J Med Chem, 2004, vol. 47, pp. 1739-1749.

Garrett e a., "Crystal structure of the first three domains of the type-1 insulin-like growth factor receptor", Nature, 1998, vol. 394, pp. 395-399.

Gallop et al., "Application of combinatorial technologies to drug discovery. 1. background and peptide combinatorial libraries", Journal of Medicinal Chemistry, 1994, vol. 37, No. 9, pp. 1233-1251.

Goodford, "A computational procedure for determining energetically favorable binding sites on biologically important macromolecules", J Med Chem, 1985, vol. 28, pp. 849-857.

Goodsell et al., "Automated docking of substrates to proteins by simulated annealing", Proteins: Structure, Function and Genetics, 1990, vol. 8, pp. 195-202.

Guida, "Software for structure-based drug design", Current Opinion in Structural Biology, 1994, vol. 4, pp. 777-781.

Hess et al., "LINCS: A linear constraint solver for molecular simulations", Journal of Computational Chemistry, 1997, vol. 18, No. 12, pp. 1463-1472.

Houghten et al., "Generation and use of synthetic peptide combinatorial libraries for basic research and drug discovery", Nature, 1991, vol. 354, pp. 84-86.

Kristensen et al., "Expression and characterization of a 70-kDa fragment of the insulin receptor that binds insulin: minimizing ligand binding domain of the insulin receptor", J Biol Chem, 1998, 273, 17780-17786.

Mynarcik et al., "Alanine-scanning mutagenesis of a C-terminal ligand binding domain of the insulin receptor alpha subunit", J Biol Chem, 1996, 271, 2439-2442.

* cited by examiner (C-terminal region of IR α-chain with IGF-1R ectodomain)

(C-terminal region of IGF-1R α-chain with IR ectodomain)

(C-terminal region of IGF-1R α-chain with IGF-1R ectodomain)

(S519C16 peptide with IR ectodomain)

(SS19C16 peptide with IGF-1R ectodomain)

SEQUENCE LISTING

<160> NUMBER OF SEQ ID NOS: 19

<210> SEQ ID NO 1
<211> LENGTH: 917
<212> TYPE: PRT
<213> ORGANISM: Homo sapiens

<400> SEQUENCE: 1

His Leu Tyr Pro Gly Glu Val Cys Pro Gly Met Asp Ile Arg Asn Asn
 1               5                  10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn His
    130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
        195                 200                 205

His Ser Glu Cys Leu Gly Asn Cys Ser Gln Pro Asp Asp Pro Thr Lys
    210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255

Ser Phe Cys Gln Asp Leu His His Lys Cys Lys Asn Ser Arg Arg Gln
            260                 265                 270

Gly Cys His Gln Tyr Val Ile His Asn Asn Lys Cys Ile Pro Glu Cys
        275                 280                 285

Pro Ser Gly Tyr Thr Met Asn Ser Ser Asn Leu Leu Cys Thr Pro Cys
    290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
            340                 345                 350

Glu Leu Glu Ala Asn Leu Gly Leu Ile Glu Glu Ile Ser Gly Tyr Leu
        355                 360                 365

```
Lys Ile Arg Arg Ser Tyr Ala Leu Val Ser Leu Ser Phe Phe Arg Lys
    370                 375                 380

Leu Arg Leu Ile Arg Gly Glu Thr Leu Glu Ile Gly Asn Tyr Ser Phe
385                 390                 395                 400

Tyr Ala Leu Asp Asn Gln Asn Leu Arg Gln Leu Trp Asp Trp Ser Lys
            405                 410                 415

His Asn Leu Thr Ile Thr Gln Gly Lys Leu Phe Phe His Tyr Asn Pro
        420                 425                 430

Lys Leu Cys Leu Ser Glu Ile His Lys Met Glu Glu Val Ser Gly Thr
    435                 440                 445

Lys Gly Arg Gln Glu Arg Asn Asp Ile Ala Leu Lys Thr Asn Gly Asp
450                 455                 460

Gln Ala Ser Cys Glu Asn Glu Leu Leu Lys Phe Ser Tyr Ile Arg Thr
465                 470                 475                 480

Ser Phe Asp Lys Ile Leu Leu Arg Trp Glu Pro Tyr Trp Pro Pro Asp
            485                 490                 495

Phe Arg Asp Leu Leu Gly Phe Met Leu Phe Tyr Lys Glu Ala Pro Tyr
        500                 505                 510

Gln Asn Val Thr Glu Phe Asp Gly Gln Asp Ala Cys Gly Ser Asn Ser
        515                 520                 525

Trp Thr Val Val Asp Ile Asp Pro Pro Leu Arg Ser Asn Asp Pro Lys
530                 535                 540

Ser Gln Asn His Pro Gly Trp Leu Met Arg Gly Leu Lys Pro Trp Thr
545                 550                 555                 560

Gln Tyr Ala Ile Phe Val Lys Thr Leu Val Thr Phe Ser Asp Glu Arg
            565                 570                 575

Arg Thr Tyr Gly Ala Lys Ser Asp Ile Ile Tyr Val Gln Thr Asp Ala
        580                 585                 590

Thr Asn Pro Ser Val Pro Leu Asp Pro Ile Ser Val Ser Asn Ser Ser
        595                 600                 605

Ser Gln Ile Ile Leu Lys Trp Lys Pro Pro Ser Asp Pro Asn Gly Asn
610                 615                 620

Ile Thr His Tyr Leu Val Phe Trp Glu Arg Gln Ala Glu Asp Ser Glu
625                 630                 635                 640

Leu Phe Glu Leu Asp Tyr Cys Leu Lys Gly Leu Lys Leu Pro Ser Arg
            645                 650                 655

Thr Trp Ser Pro Pro Phe Glu Ser Glu Asp Ser Gln Lys His Asn Gln
        660                 665                 670

Ser Glu Tyr Glu Asp Ser Ala Gly Glu Cys Cys Ser Cys Pro Lys Thr
        675                 680                 685

Asp Ser Gln Ile Leu Lys Glu Leu Glu Glu Ser Ser Phe Arg Lys Thr
    690                 695                 700

Phe Glu Asp Tyr Leu His Asn Val Val Phe Val Pro Arg Pro Ser Arg
705                 710                 715                 720

Lys Arg Arg Ser Leu Gly Asp Val Gly Asn Val Thr Val Ala Val Pro
            725                 730                 735

Thr Val Ala Ala Phe Pro Asn Thr Ser Ser Thr Ser Val Pro Thr Ser
        740                 745                 750

Pro Glu Glu His Arg Pro Phe Glu Lys Val Val Asn Lys Glu Ser Leu
        755                 760                 765

Val Ile Ser Gly Leu Arg His Phe Thr Gly Tyr Arg Ile Glu Leu Gln
770                 775                 780

Ala Cys Asn Gln Asp Thr Pro Glu Glu Arg Cys Ser Val Ala Ala Tyr
```

```
                785                 790                 795                 800
Val Ser Ala Arg Thr Met Pro Glu Ala Lys Ala Asp Asp Ile Val Gly
                    805                 810                 815

Pro Val Thr His Glu Ile Phe Glu Asn Asn Val Val His Leu Met Trp
                820                 825                 830

Gln Glu Pro Lys Glu Pro Asn Gly Leu Ile Val Leu Tyr Glu Val Ser
                835                 840                 845

Tyr Arg Arg Tyr Gly Asp Glu Glu Leu His Leu Cys Asp Thr Arg Lys
                850                 855                 860

His Phe Ala Leu Glu Arg Gly Cys Arg Leu Arg Gly Leu Ser Pro Gly
865                 870                 875                 880

Asn Tyr Ser Val Arg Ile Arg Ala Thr Ser Leu Ala Gly Asn Gly Ser
                885                 890                 895

Trp Thr Glu Pro Thr Tyr Phe Tyr Val Thr Asp Tyr Leu Asp Val Pro
                900                 905                 910

Ser Asn Ile Ala Lys
                915

<210> SEQ ID NO 2
<211> LENGTH: 929
<212> TYPE: PRT
<213> ORGANISM: Homo sapiens

<400> SEQUENCE: 2

His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
                20                  25                  30

Leu Gln Ile Leu Leu Met Phe Lys Thr Arg Pro Glu Asp Phe Arg Asp
            35                  40                  45

Leu Ser Phe Pro Lys Leu Ile Met Ile Thr Asp Tyr Leu Leu Leu Phe
        50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
                100                 105                 110

Thr Arg Gly Ser Val Arg Ile Glu Lys Asn Asn Glu Leu Cys Tyr Leu
            115                 120                 125

Ala Thr Ile Asp Trp Ser Arg Ile Leu Asp Ser Val Glu Asp Asn His
        130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
                180                 185                 190

Pro Thr Ile Cys Lys Ser His Gly Cys Thr Ala Glu Gly Leu Cys Cys
            195                 200                 205

His Ser Glu Cys Leu Gly Asn Cys Ser Gln Pro Asp Asp Pro Thr Lys
        210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
```

```
                    245                 250                 255
Ser Phe Cys Gln Asp Leu His His Lys Cys Lys Asn Ser Arg Arg Gln
                260                 265                 270
Gly Cys His Gln Tyr Val Ile His Asn Asn Lys Cys Ile Pro Glu Cys
            275                 280                 285
Pro Ser Gly Tyr Thr Met Asn Ser Ser Asn Leu Leu Cys Thr Pro Cys
        290                 295                 300
Leu Gly Pro Cys Pro Lys Val Cys His Leu Leu Glu Gly Glu Lys Thr
    305                 310                 315                 320
Ile Asp Ser Val Thr Ser Ala Gln Glu Leu Arg Gly Cys Thr Val Ile
                325                 330                 335
Asn Gly Ser Leu Ile Ile Asn Ile Arg Gly Gly Asn Asn Leu Ala Ala
            340                 345                 350
Glu Leu Glu Ala Asn Leu Gly Leu Ile Glu Glu Ile Ser Gly Tyr Leu
        355                 360                 365
Lys Ile Arg Arg Ser Tyr Ala Leu Val Ser Leu Ser Phe Phe Arg Lys
    370                 375                 380
Leu Arg Leu Ile Arg Gly Glu Thr Leu Glu Ile Gly Asn Tyr Ser Phe
385                 390                 395                 400
Tyr Ala Leu Asp Asn Gln Asn Leu Arg Gln Leu Trp Asp Trp Ser Lys
                405                 410                 415
His Asn Leu Thr Ile Thr Gln Gly Lys Leu Phe Phe His Tyr Asn Pro
            420                 425                 430
Lys Leu Cys Leu Ser Glu Ile His Lys Met Glu Glu Val Ser Gly Thr
        435                 440                 445
Lys Gly Arg Gln Glu Arg Asn Asp Ile Ala Leu Lys Thr Asn Gly Asp
    450                 455                 460
Gln Ala Ser Cys Glu Asn Glu Leu Leu Lys Phe Ser Tyr Ile Arg Thr
465                 470                 475                 480
Ser Phe Asp Lys Ile Leu Leu Arg Trp Glu Pro Tyr Trp Pro Pro Asp
                485                 490                 495
Phe Arg Asp Leu Leu Gly Phe Met Leu Phe Tyr Lys Glu Ala Pro Tyr
            500                 505                 510
Gln Asn Val Thr Glu Phe Asp Gly Gln Asp Ala Cys Gly Ser Asn Ser
        515                 520                 525
Trp Thr Val Val Asp Ile Asp Pro Pro Leu Arg Ser Asn Asp Pro Lys
    530                 535                 540
Ser Gln Asn His Pro Gly Trp Leu Met Arg Gly Leu Lys Pro Trp Thr
545                 550                 555                 560
Gln Tyr Ala Ile Phe Val Lys Thr Leu Val Thr Phe Ser Asp Glu Arg
                565                 570                 575
Arg Thr Tyr Gly Ala Lys Ser Asp Ile Ile Tyr Val Gln Thr Asp Ala
            580                 585                 590
Thr Asn Pro Ser Val Pro Leu Asp Pro Ile Ser Val Ser Asn Ser Ser
        595                 600                 605
Ser Gln Ile Ile Leu Lys Trp Lys Pro Pro Ser Asp Pro Asn Gly Asn
    610                 615                 620
Ile Thr His Tyr Leu Val Phe Trp Glu Arg Gln Ala Glu Asp Ser Glu
625                 630                 635                 640
Leu Phe Glu Leu Asp Tyr Cys Leu Lys Gly Leu Lys Leu Pro Ser Arg
                645                 650                 655
Thr Trp Ser Pro Pro Phe Glu Ser Glu Asp Ser Gln Lys His Asn Gln
            660                 665                 670
```

```
Ser Glu Tyr Glu Asp Ser Ala Gly Glu Cys Cys Ser Cys Pro Lys Thr
        675                 680                 685

Asp Ser Gln Ile Leu Lys Glu Leu Glu Ser Ser Phe Arg Lys Thr
690                 695                 700

Phe Glu Asp Tyr Leu His Asn Val Val Phe Val Pro Arg Lys Thr Ser
705                 710                 715                 720

Ser Gly Thr Gly Ala Glu Asp Pro Arg Pro Ser Arg Lys Arg Arg Ser
        725                 730                 735

Leu Gly Asp Val Gly Asn Val Thr Val Ala Val Pro Thr Val Ala Ala
            740                 745                 750

Phe Pro Asn Thr Ser Ser Thr Ser Val Pro Thr Ser Pro Glu Glu His
        755                 760                 765

Arg Pro Phe Glu Lys Val Val Asn Lys Glu Ser Leu Val Ile Ser Gly
770                 775                 780

Leu Arg His Phe Thr Gly Tyr Arg Ile Glu Leu Gln Ala Cys Asn Gln
785                 790                 795                 800

Asp Thr Pro Glu Glu Arg Cys Ser Val Ala Ala Tyr Val Ser Ala Arg
            805                 810                 815

Thr Met Pro Glu Ala Lys Ala Asp Asp Ile Val Gly Pro Val Thr His
            820                 825                 830

Glu Ile Phe Glu Asn Asn Val Val His Leu Met Trp Gln Glu Pro Lys
835                 840                 845

Glu Pro Asn Gly Leu Ile Val Leu Tyr Glu Val Ser Tyr Arg Arg Tyr
        850                 855                 860

Gly Asp Glu Glu Leu His Leu Cys Asp Thr Arg Lys His Phe Ala Leu
865                 870                 875                 880

Glu Arg Gly Cys Arg Leu Arg Gly Leu Ser Pro Gly Asn Tyr Ser Val
            885                 890                 895

Arg Ile Arg Ala Thr Ser Leu Ala Gly Asn Gly Ser Trp Thr Glu Pro
            900                 905                 910

Thr Tyr Phe Tyr Val Thr Asp Tyr Leu Asp Val Pro Ser Asn Ile Ala
        915                 920                 925

Lys

<210> SEQ ID NO 3
<211> LENGTH: 1372
<212> TYPE: PRT
<213> ORGANISM: Mus musculus

<400> SEQUENCE: 3

Met Gly Phe Gly Arg Gly Cys Glu Thr Thr Ala Val Pro Leu Leu Val
1               5                   10                  15

Ala Val Ala Ala Leu Leu Val Gly Thr Ala Gly His Leu Tyr Pro Gly
            20                  25                  30

Glu Val Cys Pro Gly Met Asp Ile Arg Asn Asn Leu Thr Arg Leu His
        35                  40                  45

Glu Leu Glu Asn Cys Ser Val Ile Glu Gly His Leu Gln Ile Leu Leu
    50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
```

```
                115                 120                 125
Lys Glu Leu Gly Leu Tyr Asn Leu Met Asn Ile Thr Arg Gly Ser Val
        130                 135                 140
Arg Ile Glu Lys Asn Asn Glu Leu Cys Tyr Leu Ala Thr Ile Asp Trp
145                 150                 155                 160
Ser Arg Ile Leu Asp Ser Val Glu Asp Asn Tyr Ile Val Leu Asn Lys
                165                 170                 175
Asp Asp Asn Glu Glu Cys Gly Asp Val Cys Pro Gly Thr Ala Lys Gly
            180                 185                 190
Lys Thr Asn Cys Pro Ala Thr Val Ile Asn Gly Gln Phe Val Glu Arg
                195                 200                 205
Cys Trp Thr His Ser His Cys Gln Lys Val Cys Pro Thr Ile Cys Lys
        210                 215                 220
Ser His Gly Cys Thr Ala Glu Gly Leu Cys Cys His Lys Glu Cys Leu
225                 230                 235                 240
Gly Asn Cys Ser Glu Pro Asp Asp Pro Thr Lys Cys Val Ala Cys Arg
                245                 250                 255
Asn Phe Tyr Leu Asp Gly Gln Cys Val Glu Thr Cys Pro Pro Pro Tyr
            260                 265                 270
Tyr His Phe Gln Asp Trp Arg Cys Val Asn Phe Ser Phe Cys Gln Asp
                275                 280                 285
Leu His Phe Lys Cys Arg Asn Ser Arg Lys Pro Gly Cys His Gln Tyr
        290                 295                 300
Val Ile His Asn Asn Lys Cys Ile Pro Glu Cys Pro Ser Gly Tyr Thr
305                 310                 315                 320
Met Asn Ser Ser Asn Leu Met Cys Thr Pro Cys Leu Gly Pro Cys Pro
                325                 330                 335
Lys Val Cys Gln Ile Leu Glu Gly Glu Lys Thr Ile Asp Ser Val Thr
            340                 345                 350
Ser Ala Gln Glu Leu Arg Gly Cys Thr Val Ile Asn Gly Ser Leu Ile
                355                 360                 365
Ile Asn Ile Arg Gly Gly Asn Asn Leu Ala Ala Glu Leu Glu Ala Asn
        370                 375                 380
Leu Gly Leu Ile Glu Glu Ile Ser Gly Phe Leu Lys Ile Arg Arg Ser
385                 390                 395                 400
Tyr Ala Leu Val Ser Leu Ser Phe Phe Arg Lys Leu His Leu Ile Arg
                405                 410                 415
Gly Glu Thr Leu Glu Ile Gly Asn Tyr Ser Phe Tyr Ala Leu Asp Asn
            420                 425                 430
Gln Asn Leu Arg Gln Leu Trp Asp Trp Ser Lys His Asn Leu Thr Ile
                435                 440                 445
Thr Gln Gly Lys Leu Phe Phe His Tyr Asn Pro Lys Leu Cys Leu Ser
        450                 455                 460
Glu Ile His Lys Met Glu Glu Val Ser Gly Thr Lys Gly Arg Gln Glu
465                 470                 475                 480
Arg Asn Asp Ile Ala Leu Lys Thr Asn Gly Asp Gln Ala Ser Cys Glu
                485                 490                 495
Asn Glu Leu Leu Lys Phe Ser Phe Ile Arg Thr Ser Phe Asp Lys Ile
            500                 505                 510
Leu Leu Arg Trp Glu Pro Tyr Trp Pro Pro Asp Phe Arg Asp Leu Leu
        515                 520                 525
Gly Phe Met Leu Phe Tyr Lys Glu Ala Pro Tyr Gln Asn Val Thr Glu
        530                 535                 540
```

-continued

```
Phe Asp Gly Gln Asp Ala Cys Gly Ser Asn Ser Trp Thr Val Val Asp
545                 550                 555                 560

Ile Asp Pro Pro Gln Arg Ser Asn Asp Pro Lys Ser Gln Thr Pro Ser
            565                 570                 575

His Pro Gly Trp Leu Met Arg Gly Leu Lys Pro Trp Thr Gln Tyr Ala
        580                 585                 590

Ile Phe Val Lys Thr Leu Val Thr Phe Ser Asp Glu Arg Arg Thr Tyr
    595                 600                 605

Gly Ala Lys Ser Asp Ile Ile Tyr Val Gln Thr Asp Ala Thr Asn Pro
610                 615                 620

Ser Val Pro Leu Asp Pro Ile Ser Val Ser Asn Ser Ser Ser Gln Ile
625                 630                 635                 640

Ile Leu Lys Trp Lys Pro Pro Ser Asp Pro Asn Gly Asn Ile Thr His
            645                 650                 655

Tyr Leu Val Tyr Trp Glu Arg Gln Ala Glu Asp Ser Glu Leu Phe Glu
        660                 665                 670

Leu Asp Tyr Cys Leu Lys Gly Leu Lys Leu Pro Ser Arg Thr Trp Ser
    675                 680                 685

Pro Pro Phe Glu Ser Asp Asp Ser Gln Lys His Asn Gln Ser Glu Tyr
690                 695                 700

Asp Asp Ser Ala Ser Glu Cys Cys Ser Cys Pro Lys Thr Asp Ser Gln
705                 710                 715                 720

Ile Leu Lys Glu Leu Glu Ser Ser Phe Arg Lys Thr Phe Glu Asp
            725                 730                 735

Tyr Leu His Asn Val Val Phe Val Pro Arg Pro Ser Arg Lys Arg Arg
        740                 745                 750

Ser Leu Glu Glu Val Gly Asn Val Thr Ala Thr Thr Leu Thr Leu Pro
    755                 760                 765

Asp Phe Pro Asn Val Ser Ser Thr Ile Val Pro Thr Ser Gln Glu Glu
    770                 775                 780

His Arg Pro Phe Glu Lys Val Val Asn Lys Glu Ser Leu Val Ile Ser
785                 790                 795                 800

Gly Leu Arg His Phe Thr Gly Tyr Arg Ile Glu Leu Gln Ala Cys Asn
            805                 810                 815

Gln Asp Ser Pro Asp Glu Arg Cys Ser Val Ala Ala Tyr Val Ser Ala
        820                 825                 830

Arg Thr Met Pro Glu Ala Lys Ala Asp Asp Ile Val Gly Pro Val Thr
    835                 840                 845

His Glu Ile Phe Glu Asn Asn Val Val His Leu Met Trp Gln Glu Pro
850                 855                 860

Lys Glu Pro Asn Gly Leu Ile Val Leu Tyr Glu Val Ser Tyr Arg Arg
865                 870                 875                 880

Tyr Gly Asp Glu Glu Leu His Leu Cys Val Ser Arg Lys His Phe Ala
            885                 890                 895

Leu Glu Arg Gly Cys Arg Leu Arg Gly Leu Ser Pro Gly Asn Tyr Ser
        900                 905                 910

Val Arg Val Arg Ala Thr Ser Leu Ala Gly Asn Gly Ser Trp Thr Glu
    915                 920                 925

Pro Thr Tyr Phe Tyr Val Thr Asp Tyr Leu Asp Val Pro Ser Asn Ile
    930                 935                 940

Ala Lys Ile Ile Ile Gly Pro Leu Ile Phe Val Phe Leu Phe Ser Val
945                 950                 955                 960

Val Ile Gly Ser Ile Tyr Leu Phe Leu Arg Lys Arg Gln Pro Asp Gly
            965                 970                 975
```

```
Pro Met Gly Pro Leu Tyr Ala Ser Ser Asn Pro Glu Tyr Leu Ser Ala
            980                 985                 990

Ser Asp Val Phe Pro Ser Ser Val Tyr Val Pro Asp Glu Trp Glu Val
            995                1000                1005

Pro Arg Glu Lys Ile Thr Leu Leu Arg Glu Leu Gly Gln Gly Ser Phe
           1010                1015                1020

Gly Met Val Tyr Glu Gly Asn Ala Lys Asp Ile Ile Lys Gly Glu Ala
1025                1030                1035                1040

Glu Thr Arg Val Ala Val Lys Thr Val Asn Glu Ser Ala Ser Leu Arg
           1045                1050                1055

Glu Arg Ile Glu Phe Leu Asn Glu Ala Ser Val Met Lys Gly Phe Thr
           1060                1065                1070

Cys His His Val Arg Leu Leu Gly Val Val Ser Lys Gly Gln Pro
           1075                1080                1085

Thr Leu Val Val Met Glu Leu Met Ala His Gly Asp Leu Lys Ser His
           1090                1095                1100

Leu Arg Ser Leu Arg Pro Asp Ala Glu Asn Asn Pro Gly Arg Pro Pro
1105                1110                1115                1120

Pro Thr Leu Gln Glu Met Ile Gln Met Thr Ala Glu Ile Ala Asp Gly
           1125                1130                1135

Met Ala Tyr Leu Asn Ala Lys Lys Phe Val His Arg Asp Leu Ala Ala
           1140                1145                1150

Arg Asn Cys Met Val Ala His Asp Phe Thr Val Lys Ile Gly Asp Phe
           1155                1160                1165

Gly Met Thr Arg Asp Ile Tyr Glu Thr Asp Tyr Tyr Arg Lys Gly Gly
           1170                1175                1180

Lys Gly Leu Leu Pro Val Arg Trp Met Ser Pro Glu Ser Leu Lys Asp
1185                1190                1195                1200

Gly Val Phe Thr Ala Ser Ser Asp Met Trp Ser Phe Gly Val Val Leu
           1205                1210                1215

Trp Glu Ile Thr Ser Leu Ala Glu Gln Pro Tyr Gln Gly Leu Ser Asn
           1220                1225                1230

Glu Gln Val Leu Lys Phe Val Met Asp Gly Gly Tyr Leu Asp Pro Pro
           1235                1240                1245

Asp Asn Cys Pro Glu Arg Leu Thr Asp Leu Met Arg Met Cys Trp Gln
1250                1255                1260

Phe Asn Pro Lys Met Arg Pro Thr Phe Leu Glu Ile Val Asn Leu Leu
1265                1270                1275                1280

Lys Asp Asp Leu His Pro Ser Phe Pro Glu Val Ser Phe Phe Tyr Ser
           1285                1290                1295

Glu Glu Asn Lys Ala Pro Glu Ser Glu Glu Leu Glu Met Glu Phe Glu
           1300                1305                1310

Asp Met Glu Asn Val Pro Leu Asp Arg Ser Ser His Cys Gln Arg Glu
           1315                1320                1325

Glu Ala Gly Gly Arg Glu Gly Gly Ser Ser Leu Ser Ile Lys Arg Thr
           1330                1335                1340

Tyr Asp Glu His Ile Pro Tyr Thr His Met Asn Gly Gly Lys Lys Asn
1345                1350                1355                1360

Gly Arg Val Leu Thr Leu Pro Arg Ser Asn Pro Ser
           1365                1370

<210> SEQ ID NO 4
<211> LENGTH: 443
<212> TYPE: PRT
```

<213> ORGANISM: Macaca mulatta

<400> SEQUENCE: 4

```
Met Met Ser Phe Glu Leu Asp Asn Leu Ala Glu Leu Glu Ala Asn
 1               5                  10                  15

Leu Gly Leu Ile Glu Glu Ile Ser Gly Tyr Leu Lys Ile Arg Arg Ser
                20                  25                  30

Tyr Ala Leu Val Ser Leu Ser Phe Phe Arg Lys Leu Arg Leu Ile Arg
                35                  40                  45

Gly Glu Thr Leu Glu Ile Gly Asn Tyr Ser Phe Tyr Ala Leu Asp Asn
            50                  55                  60

Gln Asn Leu Arg Gln Leu Trp Asp Trp Ser Lys His Asn Leu Thr Ile
 65                 70                  75                  80

Thr Gln Gly Lys Leu Phe Phe His Tyr Asn Pro Lys Leu Cys Leu Ser
                    85                  90                  95

Glu Ile His Lys Met Glu Glu Val Ser Gly Thr Lys Gly Arg Gln Glu
                100                 105                 110

Arg Asn Asp Ile Ala Leu Lys Thr Asn Gly Asp Gln Ala Ser Cys Glu
            115                 120                 125

Asn Glu Leu Leu Lys Phe Ser Tyr Ile Arg Thr Ser Phe Asp Lys Ile
130                 135                 140

Leu Leu Arg Trp Glu Pro Tyr Trp Pro Asp Phe Arg Asp Leu Leu
145                 150                 155                 160

Gly Phe Met Leu Phe Tyr Lys Glu Ala Pro Tyr Gln Asn Val Thr Glu
                    165                 170                 175

Phe Asp Gly Gln Asp Ala Cys Gly Ser Asn Ser Trp Thr Val Val Asp
                180                 185                 190

Ile Asp Pro Pro Leu Arg Ser Asn Asp Pro Lys Ser Gln Asn His Pro
            195                 200                 205

Gly Trp Leu Met Arg Gly Leu Lys Pro Trp Thr Gln Tyr Ala Ile Phe
        210                 215                 220

Val Lys Thr Leu Val Thr Phe Ser Asp Glu Arg Arg Thr Tyr Gly Ala
225                 230                 235                 240

Lys Ser Asp Ile Ile Tyr Val Gln Thr Asp Ala Thr Asn Pro Ser Val
                    245                 250                 255

Pro Leu Asp Pro Ile Ser Val Ser Asn Ser Ser Ser Gln Ile Ile Leu
                260                 265                 270

Lys Trp Lys Pro Pro Ser Asp Pro Asn Gly Asn Ile Thr His Tyr Leu
            275                 280                 285

Val Phe Trp Glu Arg Gln Ala Glu Asp Ser Glu Leu Phe Glu Leu Asp
        290                 295                 300

Tyr Cys Leu Lys Gly Leu Lys Leu Pro Ser Arg Thr Trp Ser Pro Pro
305                 310                 315                 320

Phe Glu Ser Glu Asp Ser Gln Lys His Asn Gln Ser Glu Tyr Glu Asp
                    325                 330                 335

Ser Ala Gly Glu Cys Cys Ser Cys Pro Lys Thr Asp Ser Gln Ile Leu
                340                 345                 350

Lys Glu Leu Glu Glu Ser Ser Phe Arg Lys Thr Phe Glu Asp Tyr Leu
            355                 360                 365

His Asn Val Val Phe Val Pro Arg Lys Thr Ser Ser Gly Thr Gly Ala
        370                 375                 380

Glu Asp Pro Arg Tyr Asp Ser Pro Val Arg Pro Leu Val Pro Ala Pro
385                 390                 395                 400

Cys Arg Ala Gly Gly Val Pro Gly Arg Arg Leu Gly Glu Arg Arg Gly
```

```
                    405                 410                 415
Phe Cys Gly Phe Leu His Ala Ala Gly Cys Cys Ala Gly Asp Glu Met
                420                 425                 430

Leu His Gln Phe Arg Asn Pro Met Pro Ser Leu
        435                 440

<210> SEQ ID NO 5
<211> LENGTH: 1279
<212> TYPE: PRT
<213> ORGANISM: Bos taurus

<400> SEQUENCE: 5

Met Asp Ile Arg Asn Asn Leu Thr Arg Leu His Glu Leu Ala Asn Cys
1               5                   10                  15

Ser Val Ile Glu Gly His Leu Gln Ile Leu Leu Met Phe Lys Thr Arg
            20                  25                  30

Pro Glu Asp Phe Arg Asp Leu Ser Phe Pro Lys Leu Ile Met Ile Thr
        35                  40                  45

Asp Tyr Leu Leu Leu Phe Arg Val Tyr Gly Leu Glu Ser Leu Lys Asp
    50                  55                  60

Leu Phe Pro Asn Leu Thr Val Ile Arg Gly Ser Arg Leu Phe Phe Asn
65                  70                  75                  80

Tyr Ala Leu Val Ile Phe Glu Met Val His Leu Lys Glu Leu Gly Leu
                85                  90                  95

Tyr Asn Leu Met Asn Ile Thr Arg Gly Ser Val Arg Ile Glu Lys Asn
            100                 105                 110

Asn Glu Leu Cys Tyr Leu Ala Thr Ile Asp Trp Ser Arg Ile Leu Asp
        115                 120                 125

Ser Val Glu Asp Asn Tyr Ile Val Leu Asn Lys Asp Asp Asn Glu Glu
    130                 135                 140

Cys Gly Asp Ile Cys Pro Gly Thr Ala Lys Gly Lys Thr Asn Cys Pro
145                 150                 155                 160

Ala Thr Val Ile Asn Gly Gln Phe Val Glu Arg Cys Trp Thr His Ser
                165                 170                 175

His Cys Gln Lys Gly Pro Pro Ser Ala Ile Pro Gly Ala Ala Cys His
            180                 185                 190

Ala Val Thr Arg Ser Pro Pro Gly His Thr Pro Ser Ser Val Arg Gly
        195                 200                 205

Pro Ser His Thr Ala Ala Ala Arg Gly Gly Pro His Thr Arg Phe Leu
    210                 215                 220

Leu Phe Phe Asn Phe Phe Gln Thr Pro Ile Leu Cys Gly Pro Ala Leu
225                 230                 235                 240

Gln Gly Leu Asn Pro Arg Lys Gly Pro Pro Gly Ala Pro Gly Ala
                245                 250                 255

Asp Arg Pro Ala Ala Val Thr Arg Ala Pro Val Gly Arg Ala Glu
            260                 265                 270

Pro Arg Ala Pro Glu Gly Arg Gly Gln Ser Pro Ser Ser Thr Pro Ala
        275                 280                 285

His Trp Leu Ser Ala Arg Ala Ala Leu Arg Leu Pro Pro Pro Gly
    290                 295                 300

Pro Asp Ser Thr Glu Arg Ser Ala Pro Arg Ala Leu Cys Phe Ser Ala
305                 310                 315                 320

Ala Ala Gly Leu Arg Gly Ala Gly Leu Leu Pro Pro Asn Tyr Ser Phe
                325                 330                 335

Tyr Ala Leu Asp Asn Gln Asn Leu Arg Gln Leu Trp Asp Trp Ser Lys
```

```
                    340             345                 350
His Asn Leu Thr Ile Thr Gln Gly Lys Leu Phe Phe His Tyr Asn Pro
            355                 360                 365
Lys Leu Cys Leu Ser Glu Ile His Lys Met Glu Glu Val Ser Gly Thr
        370                 375                 380
Lys Gly Arg Gln Glu Arg Asn Asp Ile Ala Leu Lys Thr Asn Gly Asp
385                 390                 395                 400
Gln Ala Ser Cys Glu Asn Glu Leu Leu Lys Phe Ser Tyr Ile Arg Thr
                405                 410                 415
Ser Tyr Asp Lys Ile Leu Leu Lys Trp Glu Pro Tyr Trp Pro Pro Asp
            420                 425                 430
Phe Arg Asp Leu Leu Gly Phe Met Leu Phe Tyr Lys Glu Ala Pro Tyr
        435                 440                 445
Gln Asn Val Thr Glu Phe Asp Gly Gln Asp Ala Cys Gly Ser Asn Ser
    450                 455                 460
Trp Thr Val Val Asp Ile Asp Pro Pro Thr Arg Ser Asn Asp Pro Lys
465                 470                 475                 480
Ser Gln Asn His Pro Gly Trp Leu Met Arg Gly Leu Lys Pro Trp Thr
                485                 490                 495
Gln Tyr Ala Ile Phe Val Lys Thr Leu Val Thr Phe Ser Asp Glu Arg
            500                 505                 510
Arg Thr Tyr Gly Ala Lys Ser Asp Ile Ile Tyr Val Gln Thr Asp Ala
        515                 520                 525
Thr Asn Pro Ser Val Pro Leu Asp Pro Ile Ser Val Ser Asn Ser Ser
    530                 535                 540
Ser Gln Ile Ile Leu Lys Trp Lys Pro Pro Ser Asp Pro Asn Gly Asn
545                 550                 555                 560
Ile Thr His Tyr Leu Val Phe Trp Glu Arg Gln Ala Glu Asp Ser Glu
                565                 570                 575
Leu Tyr Glu Leu Asp Tyr Cys Leu Lys Gly Leu Lys Leu Pro Ser Arg
            580                 585                 590
Thr Trp Ser Pro Pro Phe Glu Ser Glu Gly Ser Gln Lys His Asn Gln
        595                 600                 605
Ser Glu Tyr Glu Glu Ser Ala Gly Glu Cys Cys Ser Cys Pro Lys Thr
    610                 615                 620
Asp Ser Gln Ile Leu Lys Glu Leu Glu Glu Ser Ser Phe Arg Lys Thr
625                 630                 635                 640
Phe Glu Asp Tyr Leu His Asn Val Val Phe Ile Pro Arg Pro Ser Arg
                645                 650                 655
Lys Arg Arg Ala Leu Gly Asp Val Gly Asn Val Thr Ala Ala Val Pro
            660                 665                 670
Thr Ala Leu Gly Leu Pro Asn Thr Ser Ser Thr Ser Thr Pro Met Ser
        675                 680                 685
Ser Glu Glu His Arg Pro Phe Glu Lys Val Val Asn Lys Glu Ser Leu
    690                 695                 700
Val Ile Ser Gly Leu Arg His Phe Thr Gly Tyr Arg Ile Glu Leu Gln
705                 710                 715                 720
Ala Cys Asn Gln Asp Ser Pro Glu Glu Arg Cys Ser Val Ala Ala Tyr
                725                 730                 735
Val Ser Ala Arg Thr Met Pro Glu Ala Lys Ala Asp Asp Ile Val Gly
            740                 745                 750
Pro Val Thr His Glu Ile Phe Glu Asn Asn Val Val His Leu Met Trp
        755                 760                 765
```

-continued

```
Gln Glu Pro Lys Glu Pro Asn Gly Leu Ile Val Leu Tyr Glu Val Ser
    770                 775                 780

Tyr Arg Arg Tyr Gly Glu Glu Leu His Leu Cys Val Ser Arg Arg
785                 790                 795                 800

His Tyr Ala Leu Glu Arg Gly Cys Arg Leu Arg Gly Leu Leu Pro Gly
                805                 810                 815

Asn Tyr Ser Val Arg Val Arg Ala Thr Ser Leu Ala Gly Asn Gly Ser
            820                 825                 830

Trp Thr Glu Ala Thr Tyr Phe Tyr Val Thr Asp Tyr Leu Asp Val Pro
        835                 840                 845

Ser Asn Ile Ala Lys Ile Ile Gly Pro Leu Ile Phe Val Phe Leu
    850                 855                 860

Phe Ser Val Val Ile Gly Ser Ile Cys Leu Phe Leu Arg Lys Arg Gln
865                 870                 875                 880

Pro Asp Gly Pro Leu Gly Pro Leu Tyr Ala Ser Ser Asn Pro Glu Tyr
                885                 890                 895

Leu Ser Ala Ser Asp Val Phe Pro Cys Ser Val Tyr Val Pro Asp Glu
            900                 905                 910

Trp Glu Val Pro Arg Glu Lys Ile Thr Leu Leu Arg Glu Leu Gly Gln
        915                 920                 925

Gly Ser Phe Gly Met Val Tyr Glu Gly Asn Ala Arg Asp Ile Val Lys
    930                 935                 940

Gly Glu Ala Glu Thr Arg Val Ala Val Lys Thr Val Asn Glu Ser Ala
945                 950                 955                 960

Ser Leu Arg Glu Arg Ile Glu Phe Leu Asn Glu Ala Ser Val Met Lys
                965                 970                 975

Gly Phe Thr Cys His His Val Val Arg Leu Leu Gly Val Val Ser Lys
            980                 985                 990

Gly Gln Pro Thr Leu Val Val Met Glu Leu Met Ala His Gly Asp Leu
        995                 1000                1005

Lys Ser Tyr Leu Arg Ser Leu Arg Pro Glu Ala Glu Asn Asn Pro Gly
    1010                1015                1020

Arg Pro Pro Pro Thr Leu Gln Glu Met Ile Gln Met Ala Ala Glu Ile
1025                1030                1035                1040

Ala Asp Gly Met Ala Tyr Leu Asn Ala Lys Lys Phe Val His Arg Asp
                1045                1050                1055

Leu Ala Ala Arg Asn Cys Met Val Ala His Asp Phe Thr Val Lys Ile
            1060                1065                1070

Gly Asp Phe Gly Met Thr Arg Asp Ile Tyr Glu Thr Asp Tyr Tyr Arg
        1075                1080                1085

Lys Gly Gly Lys Gly Leu Leu Pro Val Arg Trp Met Ala Pro Glu Ser
    1090                1095                1100

Leu Lys Asp Gly Val Phe Thr Thr Ser Ser Asp Met Trp Ser Phe Gly
1105                1110                1115                1120

Val Val Leu Trp Glu Ile Thr Ser Leu Ala Glu Gln Pro Tyr Gln Gly
                1125                1130                1135

Leu Ser Asn Glu Gln Val Leu Lys Phe Val Met Asp Gly Gly Tyr Leu
            1140                1145                1150

Asp Gln Pro Asp Asn Cys Pro Glu Arg Val Thr Asp Leu Met Arg Met
        1155                1160                1165

Cys Trp Gln Phe Asn Pro Lys Met Arg Pro Thr Phe Leu Glu Ile Val
    1170                1175                1180

Asp Leu Leu Lys Asp Asp Leu His Pro Ser Phe Pro Glu Val Ser Phe
1185                1190                1195                1200
```

```
Phe His Ser Glu Glu Asn Lys Ala Pro Glu Ser Glu Leu Glu Met
                1205                1210                1215

Glu Phe Glu Asp Met Glu Ser Val Pro Leu Asp Arg Ala Ser His Ala
            1220                1225                1230

Gln Arg Glu Glu Ala Gly Gly Arg Asp Gly Gly Ser Ala Leu Gly Leu
        1235                1240                1245

Lys Arg Asn Tyr Asp Glu His Ile Pro Tyr Thr His Met Asn Gly Gly
    1250                1255                1260

Lys Lys Asn Gly Arg Ile Leu Thr Leu Pro Arg Ser Asn Pro Ser
1265                1270                1275

<210> SEQ ID NO 6
<211> LENGTH: 906
<212> TYPE: PRT
<213> ORGANISM: Homo sapiens

<400> SEQUENCE: 6

Glu Ile Cys Gly Pro Gly Ile Asp Ile Arg Asn Asp Tyr Gln Gln Leu
 1               5                  10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
        35                  40                  45

Thr Val Ile Thr Glu Tyr Leu Leu Leu Phe Arg Val Ala Gly Leu Glu
    50                  55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
        115                 120                 125

Leu Ile Leu Asp Ala Val Ser Asn Asn Tyr Ile Val Gly Asn Lys Pro
    130                 135                 140

Pro Lys Glu Cys Gly Asp Leu Cys Pro Gly Thr Met Glu Glu Lys Pro
145                 150                 155                 160

Met Cys Glu Lys Thr Thr Ile Asn Asn Glu Tyr Asn Tyr Arg Cys Trp
                165                 170                 175

Thr Thr Asn Arg Cys Gln Lys Met Cys Pro Ser Thr Cys Gly Lys Arg
            180                 185                 190

Ala Cys Thr Glu Asn Asn Glu Cys Cys His Pro Glu Cys Leu Gly Ser
        195                 200                 205

Cys Ser Ala Pro Asp Asn Asp Thr Ala Cys Val Ala Cys Arg His Tyr
    210                 215                 220

Tyr Tyr Ala Gly Val Cys Val Pro Ala Cys Pro Pro Asn Thr Tyr Arg
225                 230                 235                 240

Phe Glu Gly Trp Arg Cys Val Asp Arg Asp Phe Cys Ala Asn Ile Leu
                245                 250                 255

Ser Ala Glu Ser Ser Asp Ser Glu Gly Phe Val Ile His Asp Gly Glu
            260                 265                 270

Cys Met Gln Glu Cys Pro Ser Gly Phe Ile Arg Asn Gly Ser Gln Ser
        275                 280                 285

Met Tyr Cys Ile Pro Cys Glu Gly Pro Cys Pro Lys Val Cys Glu Glu
    290                 295                 300
```

```
Glu Lys Lys Thr Lys Thr Ile Asp Ser Val Thr Ser Ala Gln Met Leu
305                 310                 315                 320

Gln Gly Cys Thr Ile Phe Lys Gly Asn Leu Leu Ile Asn Ile Arg Arg
                325                 330                 335

Gly Asn Asn Ile Ala Ser Glu Leu Glu Asn Phe Met Gly Leu Ile Glu
                340                 345                 350

Val Val Thr Gly Tyr Val Lys Ile Arg His Ser His Ala Leu Val Ser
                355                 360                 365

Leu Ser Phe Leu Lys Asn Leu Arg Leu Ile Leu Gly Glu Glu Gln Leu
370                 375                 380

Glu Gly Asn Tyr Ser Phe Tyr Val Leu Asp Asn Gln Asn Leu Gln Gln
385                 390                 395                 400

Leu Trp Asp Trp Asp His Arg Asn Leu Thr Ile Lys Ala Gly Lys Met
                405                 410                 415

Tyr Phe Ala Phe Asn Pro Lys Leu Cys Val Ser Glu Ile Tyr Arg Met
                420                 425                 430

Glu Glu Val Thr Gly Thr Lys Gly Arg Gln Ser Lys Gly Asp Ile Asn
                435                 440                 445

Thr Arg Asn Asn Gly Glu Arg Ala Ser Cys Glu Ser Asp Val Leu His
450                 455                 460

Phe Thr Ser Thr Thr Thr Ser Lys Asn Arg Ile Ile Ile Thr Trp His
465                 470                 475                 480

Arg Tyr Arg Pro Pro Asp Tyr Arg Asp Leu Ile Ser Phe Thr Val Tyr
                485                 490                 495

Tyr Lys Glu Ala Pro Phe Lys Asn Val Thr Glu Tyr Asp Gly Gln Asp
                500                 505                 510

Ala Cys Gly Ser Asn Ser Trp Asn Met Val Asp Val Asp Leu Pro Pro
                515                 520                 525

Asn Lys Asp Val Glu Pro Gly Ile Leu Leu His Gly Leu Lys Pro Trp
                530                 535                 540

Thr Gln Tyr Ala Val Tyr Val Lys Ala Val Thr Leu Thr Met Val Glu
545                 550                 555                 560

Asn Asp His Ile Arg Gly Ala Lys Ser Glu Ile Leu Tyr Ile Arg Thr
                565                 570                 575

Asn Ala Ser Val Pro Ser Ile Pro Leu Asp Val Leu Ser Ala Ser Asn
                580                 585                 590

Ser Ser Ser Gln Leu Ile Val Lys Trp Asn Pro Pro Ser Leu Pro Asn
                595                 600                 605

Gly Asn Leu Ser Tyr Tyr Ile Val Arg Trp Gln Arg Gln Pro Gln Asp
                610                 615                 620

Gly Tyr Leu Tyr Arg His Asn Tyr Cys Ser Lys Asp Lys Ile Pro Ile
625                 630                 635                 640

Arg Lys Tyr Ala Asp Gly Thr Ile Asp Ile Glu Glu Val Thr Glu Asn
                645                 650                 655

Pro Lys Thr Glu Val Cys Gly Gly Glu Lys Gly Pro Cys Cys Ala Cys
                660                 665                 670

Pro Lys Thr Glu Ala Glu Lys Gln Ala Glu Lys Glu Glu Ala Glu Tyr
                675                 680                 685

Arg Lys Val Phe Glu Asn Phe Leu His Asn Ser Ile Phe Val Pro Arg
                690                 695                 700

Pro Glu Arg Lys Arg Arg Asp Val Met Gln Val Ala Asn Thr Thr Met
705                 710                 715                 720

Ser Ser Arg Ser Arg Asn Thr Thr Ala Ala Asp Thr Tyr Asn Ile Thr
```

```
                    725                 730                 735
Asp Pro Glu Glu Leu Glu Thr Glu Tyr Pro Phe Phe Glu Ser Arg Val
                740                 745                 750

Asp Asn Lys Glu Arg Thr Val Ile Ser Asn Leu Arg Pro Phe Thr Leu
                755                 760                 765

Tyr Arg Ile Asp Ile His Ser Cys Asn His Glu Ala Glu Lys Leu Gly
                770                 775                 780

Cys Ser Ala Ser Asn Phe Val Phe Ala Arg Thr Met Pro Ala Glu Gly
785                 790                 795                 800

Ala Asp Asp Ile Pro Gly Pro Val Thr Trp Glu Pro Arg Pro Glu Asn
                805                 810                 815

Ser Ile Phe Leu Lys Trp Pro Glu Pro Glu Asn Pro Asn Gly Leu Ile
                820                 825                 830

Leu Met Tyr Glu Ile Lys Tyr Gly Ser Gln Val Glu Asp Gln Arg Glu
                835                 840                 845

Cys Val Ser Arg Gln Glu Tyr Arg Lys Tyr Gly Gly Ala Lys Leu Asn
                850                 855                 860

Arg Leu Asn Pro Gly Asn Tyr Thr Ala Arg Ile Gln Ala Thr Ser Leu
865                 870                 875                 880

Ser Gly Asn Gly Ser Trp Thr Asp Pro Val Phe Phe Tyr Val Gln Ala
                885                 890                 895

Lys Thr Gly Tyr Glu Asn Phe Ile His Leu
                900                 905

<210> SEQ ID NO 7
<211> LENGTH: 1369
<212> TYPE: PRT
<213> ORGANISM: Mus musculus

<400> SEQUENCE: 7

Met Lys Ser Gly Ser Gly Gly Gly Ser Pro Thr Ser Leu Trp Gly Leu
  1               5                  10                  15

Val Phe Leu Ser Ala Ala Leu Ser Leu Trp Pro Thr Ser Gly Glu Ile
                 20                  25                  30

Cys Gly Pro Gly Ile Asp Ile Arg Asn Asp Tyr Gln Gln Leu Lys Arg
             35                  40                  45

Leu Glu Asn Cys Thr Val Ile Glu Gly Phe Leu His Ile Leu Leu Ile
 50                  55                  60

Ser Lys Ala Glu Asp Tyr Arg Ser Tyr Arg Phe Pro Lys Leu Thr Val
 65                  70                  75                  80

Ile Thr Glu Tyr Leu Leu Leu Phe Arg Val Ala Gly Leu Glu Ser Leu
                 85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
            130                 135                 140

Lys Asn Ala Asp Leu Cys Tyr Leu Ser Thr Ile Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Leu Glu Glu Lys Pro Met Cys
                180                 185                 190

Glu Lys Thr Thr Ile Asn Asn Glu Tyr Asn Tyr Arg Cys Trp Thr Thr
```

```
              195                 200                 205
Asn Arg Cys Gln Lys Met Cys Pro Ser Val Cys Gly Lys Arg Ala Cys
210                 215                 220

Thr Glu Asn Asn Glu Cys Cys His Pro Glu Cys Leu Gly Ser Cys His
225                 230                 235                 240

Thr Pro Asp Asp Asn Thr Thr Cys Val Ala Cys Arg His Tyr Tyr Tyr
                245                 250                 255

Lys Gly Val Cys Val Pro Ala Cys Pro Pro Gly Thr Tyr Arg Phe Glu
            260                 265                 270

Gly Trp Arg Cys Val Asp Arg Asp Phe Cys Ala Asn Ile Pro Asn Ala
        275                 280                 285

Glu Ser Ser Asp Ser Asp Gly Phe Val Ile His Asp Asp Glu Cys Met
290                 295                 300

Gln Glu Cys Pro Ser Gly Phe Ile Arg Asn Ser Thr Gln Ser Met Tyr
305                 310                 315                 320

Cys Ile Pro Cys Glu Gly Pro Cys Pro Lys Val Cys Gly Asp Glu Glu
                325                 330                 335

Lys Lys Thr Lys Thr Ile Asp Ser Val Thr Ser Ala Gln Met Leu Gln
            340                 345                 350

Gly Cys Thr Ile Leu Lys Gly Asn Leu Leu Ile Asn Ile Arg Arg Gly
        355                 360                 365

Asn Asn Ile Ala Ser Glu Leu Glu Asn Phe Met Gly Leu Ile Glu Val
370                 375                 380

Val Thr Gly Tyr Val Lys Ile Arg His Ser His Ala Leu Val Ser Leu
385                 390                 395                 400

Ser Phe Leu Lys Asn Leu Arg Leu Ile Leu Gly Glu Glu Gln Leu Glu
                405                 410                 415

Gly Asn Tyr Ser Phe Tyr Val Leu Asp Asn Gln Asn Leu Gln Gln Leu
            420                 425                 430

Trp Asp Trp Asn His Arg Asn Leu Thr Val Arg Ser Gly Lys Met Tyr
        435                 440                 445

Phe Ala Phe Asn Pro Lys Leu Cys Val Ser Glu Ile Tyr Arg Met Glu
450                 455                 460

Glu Val Thr Gly Thr Lys Gly Arg Gln Ser Lys Gly Asp Ile Asn Thr
465                 470                 475                 480

Arg Asn Asn Gly Glu Arg Ala Ser Cys Glu Ser Asp Val Leu Arg Phe
                485                 490                 495

Thr Ser Thr Thr Thr Trp Lys Asn Arg Ile Ile Ile Thr Trp His Arg
            500                 505                 510

Tyr Arg Pro Pro Asp Tyr Arg Asp Leu Ile Ser Phe Thr Val Tyr Tyr
        515                 520                 525

Lys Glu Ala Pro Phe Lys Asn Val Thr Glu Tyr Asp Gly Gln Asp Ala
530                 535                 540

Cys Gly Ser Asn Ser Trp Asn Met Val Asp Val Asp Leu Pro Pro Asn
545                 550                 555                 560

Lys Glu Gly Glu Pro Gly Ile Leu Leu His Gly Leu Lys Pro Trp Thr
                565                 570                 575

Gln Tyr Ala Val Tyr Val Lys Ala Val Thr Leu Thr Met Val Glu Asn
            580                 585                 590

Asp His Ile Arg Gly Ala Lys Ser Glu Ile Leu Tyr Ile Arg Thr Asn
        595                 600                 605

Ala Ser Val Pro Ser Ile Pro Leu Asp Val Leu Ser Ala Ser Asn Ser
610                 615                 620
```

-continued

```
Ser Ser Gln Leu Ile Val Lys Trp Asn Pro Pro Thr Leu Pro Asn Gly
625                 630                 635                 640

Asn Leu Ser Tyr Tyr Ile Val Arg Trp Gln Arg Gln Pro Gln Asp Gly
            645                 650                 655

Tyr Leu Tyr Arg His Asn Tyr Cys Ser Lys Asp Lys Ile Pro Ile Arg
        660                 665                 670

Lys Tyr Ala Asp Gly Thr Ile Asp Val Glu Glu Val Thr Glu Asn Pro
    675                 680                 685

Lys Thr Glu Val Cys Gly Gly Asp Lys Gly Pro Cys Cys Ala Cys Pro
690                 695                 700

Lys Thr Glu Ala Glu Lys Gln Ala Glu Lys Glu Ala Glu Tyr Arg
705                 710                 715                 720

Lys Val Phe Glu Asn Phe Leu His Asn Ser Ile Phe Val Pro Arg Pro
                725                 730                 735

Glu Arg Arg Arg Arg Asp Val Met Gln Val Ala Asn Thr Thr Met Ser
            740                 745                 750

Ser Arg Ser Arg Asn Thr Thr Val Ala Asp Thr Tyr Asn Ile Thr Asp
        755                 760                 765

Pro Glu Glu Phe Glu Thr Glu Tyr Pro Phe Phe Glu Ser Arg Val Asp
770                 775                 780

Asn Lys Glu Arg Thr Val Ile Ser Asn Leu Arg Pro Phe Thr Leu Tyr
785                 790                 795                 800

Arg Ile Asp Ile His Ser Cys Asn His Glu Ala Glu Lys Leu Gly Cys
                805                 810                 815

Ser Ala Ser Asn Phe Val Phe Ala Arg Thr Met Pro Ala Glu Gly Ala
            820                 825                 830

Asp Asp Ile Pro Gly Pro Val Thr Trp Glu Pro Arg Pro Glu Asn Ser
        835                 840                 845

Ile Phe Leu Lys Trp Pro Glu Pro Glu Asn Pro Asn Gly Leu Ile Leu
    850                 855                 860

Met Tyr Glu Ile Lys Tyr Gly Ser Gln Val Glu Asp Gln Arg Glu Cys
865                 870                 875                 880

Val Ser Arg Gln Glu Tyr Arg Lys Tyr Gly Gly Ala Lys Leu Asn Arg
                885                 890                 895

Leu Asn Pro Gly Asn Tyr Thr Ala Arg Ile Gln Ala Thr Ser Leu Ser
            900                 905                 910

Gly Asn Gly Ser Trp Thr Asp Pro Val Phe Phe Tyr Val Pro Ala Lys
        915                 920                 925

Thr Thr Tyr Glu Asn Phe Met His Leu Ile Ile Ala Leu Pro Val Ala
    930                 935                 940

Ile Leu Leu Ile Val Gly Gly Leu Val Ile Met Leu Tyr Val Phe His
945                 950                 955                 960

Arg Lys Arg Asn Asn Ser Arg Leu Gly Asn Gly Val Leu Tyr Ala Ser
                965                 970                 975

Val Asn Pro Glu Tyr Phe Ser Ala Ala Asp Val Tyr Val Pro Asp Glu
            980                 985                 990

Trp Glu Val Ala Arg Glu Lys Ile Thr Met Asn Arg Glu Leu Gly Gln
        995                 1000                1005

Gly Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala Ala
1025                1030                1035                1040

Ser Met Arg Glu Arg Ile Glu Phe Leu Asn Glu Ala Ser Val Met Lys
                1045                1050                1055
```

Glu Phe Asn Cys His His Val Arg Leu Leu Gly Val Val Ser Gln
                1060                1065                1070

Gly Gln Pro Thr Leu Val Ile Met Glu Leu Met Thr Arg Gly Asp Leu
            1075                1080                1085

Lys Ser Tyr Leu Arg Ser Leu Arg Pro Glu Val Glu Gln Asn Asn Leu
        1090                1095                1100

Val Leu Ile Pro Pro Ser Leu Ser Lys Met Ile Gln Met Ala Gly Glu
1105                1110                1115                1120

Ile Ala Asp Gly Met Ala Tyr Leu Asn Ala Asn Lys Phe Val His Arg
                1125                1130                1135

Asp Leu Ala Ala Arg Asn Cys Met Val Ala Glu Asp Phe Thr Val Lys
            1140                1145                1150

Ile Gly Asp Phe Gly Met Thr Arg Asp Ile Tyr Glu Thr Asp Tyr Tyr
        1155                1160                1165

Arg Lys Gly Gly Lys Gly Leu Leu Pro Val Arg Trp Met Ser Pro Glu
1170                1175                1180

Ser Leu Lys Asp Gly Val Phe Thr Thr His Ser Asp Val Trp Ser Phe
1185                1190                1195                1200

Gly Val Val Leu Trp Glu Ile Ala Thr Leu Ala Glu Gln Pro Tyr Gln
                1205                1210                1215

Gly Leu Ser Asn Glu Gln Val Leu Arg Phe Val Met Glu Gly Gly Leu
            1220                1225                1230

Leu Asp Lys Pro Asp Asn Cys Pro Asp Met Leu Phe Glu Leu Met Arg
        1235                1240                1245

Met Cys Trp Gln Tyr Asn Pro Lys Met Arg Pro Ser Phe Leu Glu Ile
1250                1255                1260

Ile Gly Ser Ile Lys Asp Glu Met Glu Pro Ser Phe Gln Glu Val Ser
1265                1270                1275                1280

Phe Tyr Tyr Ser Glu Glu Asn Lys Pro Pro Glu Pro Glu Leu Glu
                1285                1290                1295

Met Glu Pro Glu Asn Met Glu Ser Val Pro Leu Asp Pro Ser Ala Ser
            1300                1305                1310

Ser Ala Ser Leu Pro Leu Pro Glu Arg His Ser Gly His Lys Ala Glu
        1315                1320                1325

Asn Gly Pro Gly Pro Gly Val Leu Val Leu Arg Ala Ser Phe Asp Glu
1330                1335                1340

Arg Gln Pro Tyr Ala His Met Asn Gly Gly Arg Ala Asn Glu Arg Ala
1345                1350                1355                1360

Leu Pro Leu Pro Gln Ser Ser Thr Cys
                1365

<210> SEQ ID NO 8
<211> LENGTH: 1367
<212> TYPE: PRT
<213> ORGANISM: Macaca mulatta

<400> SEQUENCE: 8

Met Lys Ser Gly Ser Gly Glu Gly Ser Pro Thr Ser Leu Trp Gly Leu
 1               5                  10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
            85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
            115                 120                 125

Gly Leu Tyr Asn Leu Arg Asn Ile Thr Arg Gly Ala Ile Arg Ile Glu
        130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
                180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Ala Cys Gly Lys Arg Ala Cys
        210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
        290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
        355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr

```
                485                 490                 495
Ser Thr Thr Thr Trp Lys Asn Arg Ile Ile Thr Trp His Arg Tyr
            500                 505                 510

Arg Pro Pro Asp Tyr Arg Asp Leu Ile Ser Phe Thr Val Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
            690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Val Ala Asp Thr Tyr Asn Ile Thr Asp Leu
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910
```

```
Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys Asp
    1010                1015                1020

Glu Pro Glu Thr Arg Val Ala Ile Lys Thr Val Asn Glu Ala Ala Ser
1025                1030                1035                1040

Met Arg Glu Arg Ile Glu Phe Leu Asn Glu Ala Ser Val Met Lys Glu
                1045                1050                1055

Phe Asn Cys His His Val Val Arg Leu Leu Gly Val Val Ser Gln Gly
            1060                1065                1070

Gln Pro Thr Leu Val Ile Met Glu Leu Met Thr Arg Gly Asp Leu Lys
        1075                1080                1085

Ser Tyr Leu Arg Ser Leu Arg Pro Glu Met Glu Asn Asn Pro Val Leu
    1090                1095                1100

Ala Pro Pro Ser Leu Ser Lys Met Ile Gln Met Ala Gly Glu Ile Ala
1105                1110                1115                1120

Asp Gly Met Ala Tyr Leu Asn Ala Asn Lys Phe Val His Arg Asp Leu
                1125                1130                1135

Ala Ala Arg Asn Cys Met Val Ala Glu Asp Phe Thr Val Lys Ile Gly
            1140                1145                1150

Asp Phe Gly Met Thr Arg Asp Ile Tyr Glu Thr Asp Tyr Tyr Arg Lys
        1155                1160                1165

Gly Gly Lys Gly Leu Leu Pro Val Arg Trp Met Ser Pro Glu Ser Leu
    1170                1175                1180

Lys Asp Gly Val Phe Thr Thr Tyr Ser Asp Val Trp Ser Phe Gly Val
1185                1190                1195                1200

Val Leu Trp Glu Ile Ala Thr Leu Ala Glu Gln Pro Tyr Gln Gly Leu
                1205                1210                1215

Ser Asn Glu Gln Val Leu Arg Phe Val Met Glu Gly Gly Leu Leu Asp
            1220                1225                1230

Lys Pro Asp Asn Cys Pro Asp Met Leu Phe Glu Leu Met Arg Met Cys
        1235                1240                1245

Trp Gln Tyr Asn Pro Lys Met Arg Pro Ser Phe Leu Glu Ile Ile Ser
    1250                1255                1260

Ser Ile Lys Asp Glu Met Glu Pro Gly Phe Arg Glu Val Ser Phe Tyr
1265                1270                1275                1280

Tyr Ser Glu Glu Asn Lys Leu Pro Glu Pro Glu Glu Leu Asp Leu Glu
                1285                1290                1295

Pro Glu Asn Met Glu Ser Val Pro Leu Asp Pro Ser Ala Ser Ser Ser
            1300                1305                1310

Ser Leu Pro Leu Pro Asp Arg His Ser Gly His Lys Ala Glu Asn Gly
        1315                1320                1325

Pro Gly Pro Gly Val Leu Val Leu Arg Ala Ser Phe Asp Glu Arg Gln
    1330                1335                1340
```

<210> SEQ ID NO 9
<211> LENGTH: 1204
<212> TYPE: PRT
<213> ORGANISM: Bos taurus

<400> SEQUENCE: 9

```
Pro Tyr Ala His Met Asn Gly Gly Arg Lys Asn Glu Arg Ala Leu Pro
1345                1350                1355                1360
Leu Pro Gln Ser Ser Thr Cys
                1365

Met Gln Ser Thr Cys Ser Leu Pro Gln Arg Asn Ser Gln His Val Thr
1               5                   10                  15
Leu Val Ile Gln Ala Leu Gly Pro Arg Arg Val Ala Gly Gly Leu Gly
                20                  25                  30
Val Pro Gly Gly Gly Pro Ser Ala Gln Arg Pro His Thr Leu Pro Val
            35                  40                  45
Pro Thr Val Cys Pro Ser Ala Cys Gly Lys Arg Ala Cys Thr Glu Thr
        50                  55                  60
His Glu Cys Cys His Pro Glu Cys Leu Gly Ser Cys Ser Ala Pro Asp
65                  70                  75                  80
Asn Ala Thr Ala Cys Val Ala Cys Arg His Tyr Tyr Tyr Ala Gly Val
                85                  90                  95
Cys Val Pro Ser Cys Pro Pro Asn Thr Tyr Arg Phe Glu Gly Trp Arg
            100                 105                 110
Cys Val Asp Arg Asp Phe Cys Ala Asn Ile Pro Asn Ala Glu Ser Ser
        115                 120                 125
Asp Ser Glu Gly Phe Val Ile His Asp Gly Glu Cys Met Gln Glu Cys
130                 135                 140
Pro Ser Gly Phe Ile Arg Asn Gly Ser Gln Ser Met Tyr Cys Ile Pro
145                 150                 155                 160
Cys Glu Gly Pro Cys Pro Lys Val Cys Glu Glu Lys Lys Thr Lys Thr
            165                 170                 175
Thr Ile Asp Ser Val Thr Ser Ala Gln Met Leu Gln Gly Cys Thr Ile
        180                 185                 190
Phe Lys Gly Asn Leu Leu Ile Asn Ile Arg Arg Gly Asn Asn Ile Ala
    195                 200                 205
Ser Glu Leu Glu Asn Phe Met Gly Leu Ile Glu Val Val Thr Gly Tyr
210                 215                 220
Val Lys Ile Arg His Ser His Ala Leu Val Ser Leu Ser Phe Leu Lys
225                 230                 235                 240
Asn Leu Arg Gln Ile Leu Gly Glu Glu Gln Leu Glu Gly Asn Tyr Ser
                245                 250                 255
Phe Tyr Val Leu Asp Asn Gln Asn Leu Gln Gln Leu Trp Asp Trp Asp
            260                 265                 270
His Arg Asn Leu Thr Ile Lys Ala Gly Lys Met Tyr Phe Ala Phe Asn
        275                 280                 285
Pro Lys Leu Cys Val Ser Glu Ile Tyr Arg Met Glu Glu Val Thr Gly
    290                 295                 300
Thr Lys Gly Arg Gln Ser Lys Gly Asp Ile Asn Thr Arg Asn Asn Gly
305                 310                 315                 320
Glu Arg Ala Ser Cys Glu Ser Asp Val Leu His Phe Thr Ser Thr Thr
                325                 330                 335
Thr Ser Lys Asn Arg Ile Ile Ile Thr Trp His Arg Tyr Arg Pro Pro
            340                 345                 350
```

```
Asp Tyr Arg Asp Leu Ile Ser Phe Thr Val Tyr Tyr Lys Glu Ala Pro
            355                 360                 365

Phe Lys Asn Val Thr Glu Tyr Asp Gly Gln Asp Ala Cys Gly Ser Asn
        370                 375                 380

Ser Trp Asn Met Val Asp Val Asp Leu Pro Pro Asn Lys Asp Val Glu
385                 390                 395                 400

Pro Gly Ile Leu Leu His Gly Leu Lys Pro Trp Thr Gln Tyr Ala Val
                405                 410                 415

Tyr Val Lys Ala Val Thr Leu Thr Met Val Glu Asn Asp His Ile Arg
            420                 425                 430

Gly Ala Lys Ser Glu Ile Leu Tyr Ile Arg Thr Asn Ala Ser Val Pro
        435                 440                 445

Ser Ile Pro Leu Asp Val Leu Ser Ala Ser Asn Ser Ser Ser Gln Leu
    450                 455                 460

Ile Val Lys Trp Asn Pro Pro Ser Leu Pro Asn Gly Asn Leu Ser Tyr
465                 470                 475                 480

Tyr Ile Val Arg Trp Gln Arg Gln Pro Gln Asp Ser Tyr Leu Tyr Arg
                485                 490                 495

His Asn Tyr Cys Ser Lys Asp Lys Ile Pro Ile Arg Lys Tyr Ala Asp
            500                 505                 510

Gly Thr Ile Asp Val Glu Glu Val Thr Glu Asn Pro Lys Thr Glu Val
        515                 520                 525

Cys Gly Gly Glu Lys Gly Pro Cys Cys Ala Cys Pro Lys Thr Glu Ala
    530                 535                 540

Glu Lys Gln Ala Glu Lys Glu Glu Ala Glu Tyr Arg Lys Val Phe Glu
545                 550                 555                 560

Asn Phe Leu His Asn Ala Ile Phe Val Pro Arg Pro Glu Arg Lys Arg
                565                 570                 575

Arg Glu Val Met Gln Ile Ala Asn Thr Thr Met Ser Ser Arg Ser Arg
            580                 585                 590

Asn Thr Thr Val Leu Asp Thr Tyr Asn Ile Thr Asp Pro Glu Glu Leu
        595                 600                 605

Glu Thr Glu Tyr Pro Phe Phe Glu Ser Arg Val Asp Asn Lys Glu Arg
    610                 615                 620

Thr Val Ile Ser Asn Leu Arg Pro Phe Thr Leu Tyr Arg Ile Asp Ile
625                 630                 635                 640

His Ser Cys Asn His Glu Ala Glu Lys Leu Gly Cys Ser Ala Ser Asn
                645                 650                 655

Phe Val Phe Ala Arg Thr Met Pro Ala Glu Gly Ala Asp Asp Ile Pro
            660                 665                 670

Gly Pro Val Thr Trp Glu Pro Arg Pro Glu Asn Ser Ile Phe Leu Lys
        675                 680                 685

Trp Pro Glu Pro Glu Asn Pro Asn Gly Leu Ile Leu Met Tyr Glu Ile
    690                 695                 700

Lys Tyr Gly Ser Gln Val Glu Asp Gln Arg Glu Cys Val Ser Arg Gln
705                 710                 715                 720

Glu Tyr Arg Lys Tyr Gly Gly Ala Lys Leu Asn Arg Leu Asn Pro Gly
                725                 730                 735

Asn Tyr Thr Ala Arg Ile Gln Ala Thr Ser Leu Ser Gly Asn Gly Ser
            740                 745                 750

Trp Thr Asp Pro Val Phe Phe Tyr Val Gln Ala Lys Thr Thr Tyr Glu
        755                 760                 765

Asn Phe Ile His Leu Met Ile Ala Leu Pro Ile Ala Val Leu Leu Ile
```

-continued

```
            770                 775                 780
Val Gly Gly Leu Val Ile Met Leu Tyr Val Phe His Arg Lys Arg Asn
785                 790                 795                 800

Ser Ser Arg Leu Gly Asn Gly Val Leu Tyr Ala Ser Val Asn Pro Glu
                805                 810                 815

Tyr Phe Ser Ala Ala Asp Val Tyr Val Pro Asp Glu Trp Glu Val Ala
                820                 825                 830

Arg Glu Lys Ile Thr Met Ser Arg Glu Leu Gly Gln Gly Ser Phe Gly
                835                 840                 845

Met Val Tyr Glu Gly Val Ala Lys Gly Val Val Lys Asp Glu Pro Glu
850                 855                 860

Thr Arg Val Ala Ile Lys Thr Val Asn Glu Ala Ala Ser Met Arg Glu
865                 870                 875                 880

Arg Ile Glu Phe Leu Asn Glu Ala Ser Val Met Lys Glu Phe Asn Cys
                885                 890                 895

His His Val Val Arg Leu Leu Gly Val Val Ser Gln Gly Gln Pro Thr
                900                 905                 910

Leu Val Ile Met Glu Leu Met Thr Arg Gly Asp Leu Lys Ser Tyr Leu
                915                 920                 925

Arg Ser Leu Arg Pro Glu Met Glu Asn Asn Pro Val Leu Ala Pro Pro
930                 935                 940

Ser Leu Ser Lys Met Ile Gln Met Ala Gly Glu Ile Ala Asp Gly Met
945                 950                 955                 960

Ala Tyr Leu Asn Ala Asn Lys Phe Val His Arg Asp Leu Ala Ala Arg
                965                 970                 975

Asn Cys Met Val Ala Glu Asp Phe Thr Val Lys Ile Gly Asp Phe Gly
                980                 985                 990

Met Thr Arg Asp Ile Tyr Glu Thr Asp Tyr Tyr Arg Lys Gly Gly Lys
                995                 1000                1005

Gly Leu Leu Pro Val Arg Trp Met Ser Pro Glu Ser Leu Lys Asp Gly
                1010                1015                1020

Val Phe Thr Thr His Ser Asp Val Trp Ser Phe Gly Val Val Leu Trp
1025                1030                1035                1040

Glu Ile Ala Thr Leu Ala Glu Gln Pro Tyr Gln Gly Leu Ser Asn Glu
                1045                1050                1055

Gln Val Leu Arg Phe Val Met Glu Gly Gly Leu Leu Asp Lys Pro Asp
                1060                1065                1070

Asn Cys Pro Asp Met Leu Phe Glu Leu Met Arg Met Cys Trp Gln Tyr
                1075                1080                1085

Asn Pro Lys Met Arg Pro Ser Phe Leu Glu Ile Ile Ser Ser Val Lys
                1090                1095                1100

Asp Glu Met Glu Ala Gly Phe Arg Glu Val Ser Phe Tyr Tyr Ser Glu
1105                1110                1115                1120

Glu Asn Lys Pro Pro Glu Pro Glu Glu Leu Asp Leu Glu Pro Glu Asn
                1125                1130                1135

Met Glu Ser Val Pro Leu Asp Pro Ser Ala Ser Ser Ala Ser Leu Pro
                1140                1145                1150

Leu Pro Asp Arg His Ser Gly His Lys Ala Glu Asn Gly Pro Gly Pro
                1155                1160                1165

Gly Val Leu Val Leu Arg Ala Ser Phe Asp Glu Arg Gln Pro Tyr Ala
                1170                1175                1180

His Met Asn Gly Gly Arg Lys Asn Glu Arg Ala Leu Pro Leu Pro Gln
1185                1190                1195                1200
```

Ser Ser Thr Cys

<210> SEQ ID NO 10
<211> LENGTH: 502
<212> TYPE: PRT
<213> ORGANISM: Homo sapiens

<400> SEQUENCE: 10

His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn His
    130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
        195                 200                 205

His Ser Glu Cys Leu Gly Asn Cys Ser Gln Pro Asp Asp Pro Thr Lys
    210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255

Ser Phe Cys Gln Asp Leu His His Lys Cys Lys Asn Ser Arg Arg Gln
            260                 265                 270

Gly Cys His Gln Tyr Val Ile His Asn Asn Lys Cys Ile Pro Glu Cys
        275                 280                 285

Pro Ser Gly Tyr Thr Met Asn Ser Ser Asn Leu Leu Cys Thr Pro Cys
    290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
            340                 345                 350

Glu Leu Glu Ala Asn Leu Gly Leu Ile Glu Glu Ile Ser Gly Tyr Leu
        355                 360                 365

Lys Ile Arg Arg Ser Tyr Ala Leu Val Ser Leu Ser Phe Phe Arg Lys

```
                370             375             380
Leu Arg Leu Ile Arg Gly Glu Thr Leu Glu Ile Gly Asn Tyr Ser Phe
385                 390                 395                 400

Tyr Ala Leu Asp Asn Gln Asn Leu Arg Gln Leu Trp Asp Trp Ser Lys
                405                 410                 415

His Asn Leu Thr Thr Thr Gln Gly Lys Leu Phe Phe His Tyr Asn Pro
            420                 425                 430

Lys Leu Cys Leu Ser Glu Ile His Lys Met Glu Glu Val Ser Gly Thr
        435                 440                 445

Lys Gly Arg Gln Glu Arg Asn Asp Ile Ala Leu Lys Thr Asn Gly Asp
450                 455                 460

Lys Ala Ser Cys Glu Asn Glu Leu Leu Lys Phe Ser Tyr Ile Arg Thr
465                 470                 475                 480

Ser Phe Asp Lys Ile Ser Asp Asp Asp Lys Glu Gln Lys Leu Ile
                485                 490                 495

Ser Glu Glu Asp Leu Asn
            500

<210> SEQ ID NO 11
<211> LENGTH: 16
<212> TYPE: PRT
<213> ORGANISM: Homo sapiens

<400> SEQUENCE: 11

Thr Phe Glu Asp Tyr Leu His Asn Val Val Phe Val Pro Arg Pro Ser
1               5                   10                  15

<210> SEQ ID NO 12
<211> LENGTH: 16
<212> TYPE: PRT
<213> ORGANISM: Homo sapiens

<400> SEQUENCE: 12

Thr Phe Glu Asp Tyr Leu His Asn Val Val Ala Val Pro Arg Pro Ser
1               5                   10                  15

<210> SEQ ID NO 13
<211> LENGTH: 18
<212> TYPE: PRT
<213> ORGANISM: Homo sapiens

<400> SEQUENCE: 13

Leu Lys Glu Leu Glu Glu Ser Ser Phe Arg Lys Thr Phe Glu Asp Tyr
1               5                   10                  15

Leu His

<210> SEQ ID NO 14
<211> LENGTH: 16
<212> TYPE: PRT
<213> ORGANISM: Homo sapiens

<400> SEQUENCE: 14

Val Phe Glu Asn Phe Leu His Asn Ser Ile Phe Val Pro Arg Pro Glu
1               5                   10                  15

<210> SEQ ID NO 15
<211> LENGTH: 17
<212> TYPE: PRT
<213> ORGANISM: Homo sapiens

<400> SEQUENCE: 15
```

```
Ala Glu Lys Glu Glu Ala Glu Tyr Arg Lys Val Phe Glu Asn Phe Leu
1               5                   10                  15

His

<210> SEQ ID NO 16
<211> LENGTH: 36
<212> TYPE: PRT
<213> ORGANISM: Homo sapiens

<400> SEQUENCE: 16

Ser Leu Glu Glu Glu Trp Ala Gln Val Glu Cys Glu Val Tyr Gly Arg
1               5                   10                  15

Gly Cys Pro Ser Gly Ser Leu Asp Glu Ser Phe Tyr Asp Trp Phe Glu
            20                  25                  30

Arg Gln Leu Gly
        35

<210> SEQ ID NO 17
<211> LENGTH: 20
<212> TYPE: PRT
<213> ORGANISM: Homo sapiens

<400> SEQUENCE: 17

Ser Leu Glu Glu Glu Trp Ala Gln Val Glu Cys Glu Val Tyr Gly Arg
1               5                   10                  15

Gly Cys Pro Ser
            20

<210> SEQ ID NO 18
<211> LENGTH: 16
<212> TYPE: PRT
<213> ORGANISM: Homo sapiens

<400> SEQUENCE: 18

Gly Ser Leu Asp Glu Ser Phe Tyr Asp Trp Phe Glu Arg Gln Leu Gly
1               5                   10                  15

<210> SEQ ID NO 19
<211> LENGTH: 5
<212> TYPE: PRT
<213> ORGANISM: Artificial Sequence
<220> FEATURE:
<223> OTHER INFORMATION: Conserved motif of insulin-mimetic peptides
<220> FEATURE:
<221> NAME/KEY: misc_feature
<222> LOCATION: (3)..(3)
<223> OTHER INFORMATION: Xaa = any amino acid

<400> SEQUENCE: 19

Phe Tyr Xaa Trp Phe
1               5
```

STRUCTURE OF THE C-TERMINAL REGION OF THE INSULIN RECEPTOR α-CHAIN AND OF THE INSULIN-LIKE GROWTH FACTOR RECEPTOR α-CHAIN

CROSS REFERENCE TO RELATED APPLICATIONS

The present application is a National Stage Application claiming the priority of co-pending PCT Application No. PCT/AU2010/000271 filed Mar. 9, 2010, which in turn, claims priority from U.S. Provisional Application Ser. No. 61/214,472, filed Apr. 22, 2009. Applicants claim the benefits of 35 U.S.C. §120 as to the PCT application and priority under 35 U.S.C. §119 as to the said U.S. provisional application, and the entire disclosures of both applications are incorporated herein by reference in their entireties.

FIELD OF THE INVENTION

The present invention relates generally to structural studies of the insulin binding site of the insulin receptor (IR) and the insulin-like growth factor 1 receptor (IGF-1R). More particularly, the present invention relates to the crystal structure of the low affinity insulin binding site of the IR ectodomain comprising the C-terminal region of the IR α-chain, as well as the corresponding region of IGF-1R, and to methods of using the crystal and related structural information to screen for and design compounds that interact with or modulate the function of IR and/or IGF-1R.

BACKGROUND TO THE INVENTION

The insulin receptor (IR) and its homologue the type 1 insulin-like growth factor 1 receptor (IGF-1R), are closely related members of the tyrosine kinase receptor family and are large, transmembrane, glycoprotein dimers consisting of several structural domains.

The key role of the insulin receptor (IR) is in glucose uptake and metabolism by muscle and fat. Mouse knockout studies have also shown IR to be important in adipogenesis, neovascularization, the regulation of hepatic glucose synthesis and glucose-induced pancreatic insulin secretion (Kitamura et al., 2003). IR signalling is also important in the brain, being involved in the regulation of food intake, peripheral fat deposition and the reproductive endocrine axis as well as in learning and memory (Wada et al., 2005). Dysfunctional IR signalling has been implicated in diseases including type I and type II diabetes, dementia and cancer.

IR exists as two splice variant isoforms, IR-A and IR-B, which respectively lack or contain the 12 amino acids coded by exon 11. The longer variant, IR-B, is the isoform responsible for signalling metabolic responses. In contrast, IR-A signals predominantly mitogenic responses, is the preferentially expressed isoform in several cancers (Denley et al., 2003) and is capable of binding insulin-like growth factor 2 (IGF-II) with high affinity (Denley et al., 2004).

The sequence of IR is highly homologous to the sequence of IGF-1R, indicating that the three-dimensional structures of both receptors are most likely closely similar. The mature human IR and IGF-1R molecules are each homodimers comprising two α-chains and two β-chains, the α- and β-chains arising from the post-translational cleavage at the furin cleavage site at residues 720-723 (IR-A numbering with the mature N-terminal residue numbered 1) or 707-710 (IGF-1R). The structural organization of IR and IGF-1R has been reviewed extensively (Adams et al., 2000; De Meyts and Whittaker, 2002; Ward et al., 2003; Lawrence et al., 2007; Ward and Lawrence, 2009). The sequence relationship, and domain organization of these receptors are presented in FIG. 1.

The extracellular part of each IR or IGF-1R monomer contains (sequentially from N- to C-terminus) a leucine-rich repeat domain (L1), a cysteine-rich region (CR) and a second leucine-rich repeat domain (L2), followed by three fibronectin type III domains, (FnIII-1, -2 and -3). The FnIII-2 domain contains a large insert domain (ID) of approximately 120 residues, within which lies the α-β cleavage site. Intracellularly, each monomer contains a tyrosine kinase catalytic domain flanked by two regulatory regions that contain the phosphotyrosine binding sites for signalling molecules. Each α-chain is linked to its partner β-chain via a disulphide bond between residues Cys647 and Cys860 (Sparrow et al., 1997) in the case of IR and/or Cys633-Cys849 in the case of IGF-1R. The α-chains of both IR and IGF-1R are cross-linked by disulphide bonds in two places. The first is at Cys524 (IR) or Cys514 (IGF-1R) in the FnIII-1 domain, cross-linked to its counterpart in the opposite monomer, and the second involves one or more of the residues Cys682, Cys683 and Cys685 (IR) or Cys669, Cys670 and Cys672 (IGF-1R) in the insert region of each FnIII-2 domain, cross-linked to their counterparts in the opposite monomer (Sparrow et al., 1997).

The domains of IR and IGF-1R exhibit high (47-67%) amino acid sequence identity indicative of high conservation of three-dimensional structure. The crystal structure of the first three domains of IGF-1R (L1-CR-L2) has been determined (Garrett et al., 1998) and revealed that the L domains consist of a single-stranded right-handed β-helix (a helical arrangement of β-strands), while the cysteine-rich region is composed of eight related disulfide-bonded modules. The crystal structure of the first three domains of IR (L1-CR-L2) has also been determined (WO 07/147,213; Lou et al., 2006) and as anticipated is closely similar to that of its IGF-1R counterpart. Other evidence for the close structural similarity of IR and IGF-1R arises from: (i) electron microscopic analyses (Tulloch et al., 1999), (ii) the fact that hybrid receptors (heterodimers of one IR monomer disulphide-bonded to one of IGF-1R monomer) exist naturally and are commonly found in tissues expressing both receptors (Bailyes et al., 1997); and (iii) the fact that receptor chimeras can be constructed which have whole domains or smaller segments of polypeptide from one receptor replaced by the corresponding domain or sequence from the other (reviewed in Adams et al., 2000).

The current model for insulin binding proposes that, in the basal state, the IR homodimer contains two identical pairs of binding sites (referred to as Site 1 and Site 2) on each monomer (De Meyts and Whittaker, 2002; Schäffer, 1994; De Meyts, 1994; De Meyts, 2004; Kiselyov et al., 2009). Binding of insulin to a low affinity site (Site 1) on one α-subunit is followed by a second binding event between the bound insulin and a different region of the second IR α-subunit (Site 2). This ligand-mediated bridging between the two α-subunits generates the high affinity state that results in signal transduction. In contrast, soluble IR ectodomain, which is not tethered at its C-terminus, cannot generate the high affinity receptor-ligand complex. The soluble IR ectodomain can bind two molecules of insulin simultaneously at its two Site 1s, but only with low affinity (Adams et al., 2000). The model for IGF-I or IGF-II binding to IGF-1R is the same as that just described for insulin binding to IR and involves IGF-I (or IGF-II) binding to an initial low affinity site (Site 1) and subsequent cross-linking to a second site (Site 2) on the opposite monomer to form the high affinity state, as described for the IR. However, the values of the kinetic parameters describing these events are somewhat different in the two systems (Surinya et al., 2008; Kiselyov et al., 2009).

While similar in structure, IGF-1R and IR serve different physiological functions. IGF-1R is expressed in almost all normal adult tissue except for liver, which is itself the major site of IGF-I production (Buttel et al., 1999). A variety of signalling pathways are activated following binding of IGF-I or IGF-II to IGF-1R, including Src and Ras, as well as downstream pathways, such as the MAP kinase cascade and the PI3K/AKT axis (Chow et al., 1998). IR is primarily involved in metabolic functions whereas IGF-1R mediates growth and differentiation. Consistent with this, ablation of IGF-I (i.e. in IGF-I knock-out mice) results in embryonic growth deficiency, impaired postnatal growth, and infertility. In addition, IGF-1R knock-out mice were only 45% of normal size and died of respiratory failure at birth (Liu et al., 1993). However, both insulin and IGF-I can induce both mitogenic and metabolic effects.

Various non-crystallographic 3-D structural analyses of the IR and the interaction of insulin with the IR have been undertaken using electron microscopic techniques (Luo et al., 1999; Ottensmeyer et al., 2000, 2001; Yip and Ottensmeyer, 2001). However, due to the low resolution information obtained (>20 angstrom), the conclusions of these studies have been questioned (De Meyts and Whittaker, 2002).

Crystal structures of the ectodomain of IR have been presented previously (WO 07/147,213, McKern et al., 2006; Lou et al., 2006) and have elucidated some potential ligand/IR interactions, in particular part of the low affinity site on the surface of IR L1. However, an area of ambiguous electron density on the surface of the IR L1 domain could not be resolved (WO 07/147,213, McKern et al., 2006). Accordingly, there is a need in the art to more fully resolve the structures of both IR and IGF-1R in order to elucidate all potential ligand/receptor interactions. This information would provide a more complete understanding of the mechanisms of action of both IR and IGF-1R necessary for the development of IR and IGF-1R agonists/antagonists.

SUMMARY OF THE INVENTION

The present inventors have determined the crystal structure of the low affinity insulin binding site of human IR. In particular, the crystal structure of the low affinity insulin binding site of human IR ectodomain comprising the C-terminal region of the insulin receptor α-chain has been determined. This structure allows visualisation, for the first time, of the intact low affinity insulin receptor binding site region controlling the initial binding of insulin and the subsequent formation of the high affinity insulin-IR complex that leads to signal transduction. The structure shows, for the first time, the way in which the C-terminal region of the insulin receptor α-chain associates with the first leucine-rich repeat (L1) domain of the receptor to form the complete low affinity insulin binding site. The structure also provides direct insight, for the first time, into the way the so-called Site 1 insulin mimetic peptides bind to the low affinity binding site of the insulin receptor and also provides a basis for designing insulin mimetic peptides that interact with the low affinity insulin binding site of IR. The structural information presented also indicates, by analogy, the corresponding regions in the closely related IGF-1R that are involved in insulin growth factor (IGF) binding.

The identification of molecular structures having a high degree of specificity for only one of IR or IGF-1R is important in the development of efficacious and, safe therapeutics. For example, a molecule developed as an insulin agonist should have little or no IGF-I activity in order to avoid the mitogenic activity of IGF-I and a potential for facilitating neoplastic growth. The determination of which regions of IR and IGF-1R have sufficient differences to confer selectivity for their respective ligands or for therapeutic molecules such as chemical entities or biological reagents is therefore an important and significant advancement. Similarly, it is believed that the ability to be able to identify molecular structures that mimic the active binding regions of insulin and/or IGF-I and which impart selective agonist or antagonist activity will also aid and advance the development of new drugs.

To assist in the design of agonists/antagonists of IR and/or IGF-1R, the present inventors have used the structure of human IR ectodomain comprising the C-terminal region of the insulin receptor α-chain (Appendix I) to place a model of the C-terminal region of the insulin receptor α-chain in the 3D structure of IGF-1R ectodomain (Appendix II). The present inventors have also used these models to place a model of the C-terminal region of the IGF-1R α-chain in the 3D structure of IR ectodomain and IGF-1R ectodomain (Appendixes III and IV, respectively). The present inventors used all of these structures to place a model of an insulin mimetic peptide (S519C16) in the binding site of IR and IGF-1R (Appendixes V and VI; respectively). The models, with coordinates in Appendixes II to VI, are oriented relative to atomic coordinates found in Appendix I and may be used in conjunction with atomic coordinates of Appendix I to design a compound which binds to the insulin binding site of IR and/or a compound which binds to the IGF binding site of IGF-1R.

With regards to defining structures by combining subsets of coordinates from Appendix I to Appendix VI, such combinations may be achieved by methods such as assembling combinations of complete domains from each set, assembling combinations of complete domains from each set wherein the coordinates and corresponding amino acid sequence from one structure are transposed onto those of the other, refining less resolved regions of one crystal using the corresponding coordinates of the other.

Accordingly, the present invention provides a method of identifying, designing or screening for a compound that can potentially interact with insulin receptor (IR) and/or insulin-like growth factor-1 receptor (IGF-1R), comprising performing structure-based identification, design or screening of a compound based on the compound's interactions with a structure defined by the atomic coordinates of one or more of Appendixes I to VI, or a subset of atomic coordinates of one or more thereof at least representing the C-terminal region of the α-chain of IR, the C-terminal region of the α-chain of IGF-1R, or a mimetic of the C-terminal region of the α-chain of IR and/or IGF-1R.

In one embodiment, the method comprises identifying, designing or screening for a compound which interacts with the three-dimensional structure of (i) the low affinity insulin binding site of IR, the structure being defined by the atomic coordinates shown in one or more of Appendixes I, III and V, and/or (ii) the low affinity insulin-like growth factor (IGF) binding site of IGF-1R, the structure being defined by the atomic coordinates shown in one or more of Appendixes II, IV and VI, wherein interaction of the compound with the structure is favoured energetically.

In another embodiment, the method further comprises synthesising or obtaining an identified or designed candidate compound and determining the ability of the candidate compound to interact with IR and/or IGF-1R.

In a further embodiment, the atomic coordinates define one or more regions of the low affinity binding site of IR for insulin, and/or the low affinity binding site of IGF-1R for IGF, comprising the C-terminal region of the α-chain of IR, the C-terminal region of the α-chain of IGF-1R, or a mimetic of the C-terminal region of the α-chain of IR and/or IGF-1R.

In a particularly preferred embodiment, the C-terminal region of the α-chain of IR comprise's amino acids 693 to 710 of IR α-chain (SEQ ID NO: 13).

In another preferred embodiment, the atomic coordinates defining the low affinity insulin binding site of IR further comprise the leucine-rich repeat 1 (L1) domain and/or the cysteine-rich (CR) domain of the IR ectodomain.

In yet another preferred embodiment, the atomic coordinates define portions of the molecular surface of the central β-sheet of the L1 domain and portions of the molecular surface of the second leucine-rich repeat (LRR) which contain Phe39 and/or the loop in the fourth LRR rung of the L1 domain.

In yet another preferred embodiment, the atomic coordinates define module 6 of the CR domain of IR.

In another embodiment, the atomic coordinates further define one or more amino acid sequences selected from IR amino acid residues 1-156, 157-310, 594 and 794.

In a preferred embodiment, the one or more amino acids selected from IR amino acid residues 1-156 comprise at least one amino acid selected from Arg14, Asn15, Gln34, Leu36, Leu37, Phe39, Pro43, Phe46, Leu62, Phe64, Leu87, Phe88, Phe89, Asn90, Phe96, Glu97, Arg118, Glu120 and His144.

In another embodiment, the one or more amino acids selected from IR amino acid residues 157-310 comprise at least one of the amino acid sequences selected from 192-310, 227-303 and 259-284.

The crystal structure of the first three domains of the ectodomain of IGF-1R has been previously reported (WO 99/028347). The crystal structure of the first three domains of the ectodomain of IR was subsequently reported (WO 07/147,213), enabling, for the first time, direct comparison of the regions controlling ligand specificity in the closely related IGF-1R and IR. However, the structure of the intact low affinity insulin binding site (i.e. inclusive of the C-terminal region of the receptor α-chain) could not be elucidated. As will be evident to the skilled person, the findings presented here on the intact insulin binding site of IR ectodomain structure, shape and orientation can be transposed onto the IGF binding site of IGF-1R ectodomain structure, shape and orientation.

The present invention has enabled the identification of previously unrecognised regions of the insulin binding site of IR ectodomain. By analogy, the present invention also identifies the equivalent regions in the IGF-1R, given the structural organisation of domains in the two receptors is effectively the same. The present invention has identified the critical regions of IR involved in the binding of insulin and in mediating the subsequent formation of the high affinity insulin-IR complex that leads to signal transduction. Once again, it will be evident to the skilled person that these findings can be transposed onto IGF-1R.

The present invention is therefore also useful in the identification and/or design of compounds which bind to the low affinity IGF binding site of IGF-1R.

In one embodiment, the atomic coordinates defining one or more regions of the low affinity binding site of IGF-1R for IGF, comprise the C-terminal region of the α-chain of IGF-1R. In a preferred embodiment, the C-terminal region of the α-chain of IGF-1R comprises amino acids 681 to 697 of IGF-1R α-chain (SEQ ID NO: 15).

In another embodiment, the atomic coordinates defining the low affinity IGF binding site of IGF-1R further comprise the L1 domain and/or the CR domain of IGF-1R ectodomain.

In a preferred embodiment, the atomic coordinates define the central n-sheet of the L1 domain, and/or that part of the second LRR containing Ser35, and/or the loop in the fourth LRR rung of the L1 domain.

In another preferred embodiment, the atomic coordinates define module 6 of the CR domain of IGF-1R.

In one embodiment, the mimetic of the C-terminal region of the α-chain of IR and/or IGF-1R is S519C16 (SEQ ID NO: 18).

In further embodiment, the compound substitutes for the C-terminal region of the α-chain of IR and/or the C-terminal region of the α-chain of IGF-1R in the formation of the low affinity binding site of IR or IGF-1R. Such compounds may act as either agonists or antagonists of these receptors. In one alternative of this embodiment, insulin and/or IGF-1R binds the low affinity binding site of IR and/or IGF-1R in the presence of the compound. In another alternative of this embodiment, insulin and/or IGF-1R does not bind, or has reduced binding to, the low affinity binding site of IR and/or IGF-1R in the presence of the compound.

In another embodiment, a candidate compound for interacting with IR and/or IGF-1R is chemically modified as a result of structure-based evaluation.

In a further embodiment, the chemical modification is designed to either:
i) reduce the potential for the candidate compound to bind to IR whilst maintaining binding to IGF-1R; or
ii) reduce the potential for the candidate compound to bind to IGF-1R, whilst maintaining binding to IR.

Candidate compounds and compounds identified or designed using a method of the present invention may be any suitable compound, including naturally occurring compounds, de novo designed compounds, library generated compounds (chemically or recombinantly generated), mimetics etc., and include organic compounds, new chemical entities, antibodies, binding proteins other than antibody-based molecules (nonimmunoglobulin proteins) including, for example, protein scaffolds such as lipocalins, designed ankyrin repeat proteins (DARPins, Stumpp et al., 2007) and protein A domains (reviewed in Binz et al, 2005), avimers (Silverman et al., 2005), and other new biological entities such as nucleic acid aptamers (reviewed in Ulrich, 2006).

The present invention is also useful for improving the properties of known ligands for the low affinity binding sites of IR and/or IGF-1R. For example, existing IR or IGF-1R low affinity binding site ligands can be screened against the 3D structure of the insulin binding site of IR ectodomain or a region of the insulin binding site of IR ectodomain defined by the atomic coordinates of Appendix I or a portion thereof (optionally utilising the atomic coordinates given in Appendixes II to VI to further refine the screen and/or the assessment of the potential to energetically interact with IR), and an assessment made of the potential to energetically interact with the insulin binding site of IR.

Thus, the present invention also provides a method for, redesigning a compound which is known to bind to IR and/or IGF-1R comprising performing structure-based evaluation of the compound based on the compound's interactions with a structure defined by the atomic coordinates of one or more of Appendixes I to VI, or a subset of atomic coordinates of one or more thereof at least representing the C-terminal region of the α-chain of IR, the C-terminal region of the α-chain of IGF-1R, or a mimetic of the C-terminal region of the α-chain of IR and/or IGF-1R, and redesigning or chemically modifying the compound as a result of the evaluation.

In one embodiment, the compound which is known to bind to IR and/or IGF-1R is redesigned or chemically modified to (i) improve affinity for binding to IR, and/or (ii) lower affinity for binding to IGF-1R.

In another embodiment, the compound which is known to bind to IR and/or IGF-1R is redesigned or chemically modified to (i) improve affinity for binding to IGF-1R, and/or (ii) lower affinity for binding to IR.

When screening potential ligands or compounds for selectivity for binding to the insulin binding site of IR or IGF-1R, it will be important to concentrate on those areas of difference in the 3D structure between the low affinity binding site of ectodomains of IR and IGF-1R. Such areas are identified and described herein. In particular, it will be important to concentrate on those areas of difference which are identified as being potentially important in the binding of insulin to the receptors.

Accordingly, in a further embodiment the compound is redesigned or modified so as to lower the affinity to IR or IGF-1R by virtue of the structural differences between IR and IGF-1R at or in the vicinity of the C-terminal region of the α-chain of IR and the C-terminal region of the α-chain of IGF-1R.

The present invention also provides a computer system for identifying one or more compounds that can potentially interact with IR and/or IGF-1R, the system containing data representing the structure of: (i) the low affinity insulin binding site of IR, the structure being defined by the atomic coordinates shown in one or more of Appendixes I, III and V; (ii) the low affinity IGF binding site of IGF-1R, the structure being defined by the atomic coordinates shown in one or more of Appendixes II, IV and VI; and/or (iii) the C-terminal region of the α-chain of IR, the C-terminal region of the α-chain of IGF-1R, or a mimetic of the C-terminal region of the α-chain of IR and/or IGF-1R, the structure being defined by a subset of atomic coordinates shown in one or more of Appendixes I to VI.

In another aspect, the present invention provides a computer-readable medium having recorded thereon data representing a model and/or the atomic coordinates as shown in one or more of Appendixes I to VI, or a subset of atomic coordinates of one or more thereof at least representing:

i) the C-terminal region of the α-chain of IR;

ii) the C-terminal region of the α-chain of IGF-1R; and/or iii) a mimetic of the C-terminal region of the α-chain of IR and/or IGF-1R, as any one of i) to iii) associates with IR and/or IGF-1R.

Also provided are a set of coordinates as shown in one or more of Appendixes I to VI, or a subset of atomic coordinates of one or more thereof at least representing:

i) the C-terminal region of the α-chain of IR;

ii) the C-terminal region of the α-chain of IGF-1R; and/or iii) a mimetic of the C-terminal region of the α-chain of IR and/or IGF-1R, as any one of i) to iii) associates with IR and/or IGF-1R.

The three-dimensional structure of the C-terminal region of the IR and/or IGF-1R α-chain may be used to develop models useful for drug design and/or in silico screening of candidate compounds that interact with and/or modulate IR and/or IGF-1R. Other physicochemical characteristics may also be used in developing the model, e.g. bonding, electrostatics, etc.

Generally the term "in silico" refers to the creation in a computer memory, i.e., on a silicon or other like chip. Stated otherwise "in silico" means "virtual". When used herein the term "in silico" is intended to refer to screening methods based on the use of computer models rather than in vitro or in vivo experiments.

Accordingly, the present invention also provides a computer-assisted method of identifying a compound that potentially interacts with IR and/or IGF-1R, which method comprises fitting the structure of: (i) the low affinity insulin binding site of IR, the structure being defined by the atomic coordinates shown in one or more of Appendixes I, III and V; (ii) the low affinity IGF binding site of IGF-1R, the structure being defined by the atomic coordinates shown in one or more of Appendixes II, IV and VI; and/or (iii) the C-terminal region of the α-chain of IR, the C-terminal region of the α-chain of IGF-1R, or a mimetic of the C-terminal region of the α-chain of IR and/or IGF-1R, the structure being defined by a subset of atomic coordinates shown in one or more of Appendixes I to VI, to the structure of a candidate compound.

Also provided by the present invention is a computer-assisted method for identifying a compound able to interact with IR and/or IGF-1R using a programmed computer comprising a processor, which method comprises the steps of: (a) generating, using computer methods, a set of atomic coordinates of a structure that possesses energetically favourable interactions with the atomic coordinates of: (i) the low affinity insulin binding site of IR, the structure being defined by the atomic coordinates shown in one or more of Appendixes I, III and V; (ii) the low affinity IGF binding site of IGF-1R, the structure being defined by the atomic coordinates shown in one or more of Appendixes II, IV and VI; and/or (iii) the C-terminal region of the α-chain of IR, the C-terminal region of the α-chain of IGF-1R, or a mimetic of the C-terminal region of the α-chain of IR and/or IGF-1R, the structure being defined by a subset of atomic coordinates shown in one or more of Appendixes I to VI, which coordinates are entered into the computer thereby generating a criteria data set; (b) comparing, using the processor, the criteria data set to a computer database of chemical structures; (c) selecting from the database, using computer methods, chemical structures which are complementary or similar to a region of the criteria data set; and optionally, (d) outputting, to an output device, the selected chemical structures which are complementary to or similar to a region of the criteria data set.

The present invention further provides a computer-assisted method for identifying potential mimetics of IR and/or IGF-1R using a programmed computer comprising a processor, the method comprising the steps of: (a) generating a criteria data set from a set of atomic coordinates of: (i) the low affinity insulin binding site of IR, the structure being defined by the atomic coordinates shown in one or more of Appendixes I, III and V; (ii) the low affinity IGF binding site of IGF-1R, the structure being defined by the atomic coordinates shown in one or more of Appendixes II, IV and VI; and/or (iii) the C-terminal region of the α-chain of IR, the C-terminal region of the α-chain of IGF-1R, or a mimetic of the C-terminal region of the α-chain of IR and/or IGF-1R, the structure being defined by a subset of atomic coordinates shown in one or more of Appendixes I to VI, which coordinates are entered into the computer; (b) (i) comparing, using the processor, the criteria data set to a computer database of chemical structures stored in a computer data storage system and selecting from the database, using computer methods, chemical structures having a region that is structurally similar to the criteria data set; or (ii) constructing, using computer methods, a model of a chemical structure having a region that is structurally similar to the criteria data set; and, optionally, (c) outputting to an output device: (i) the selected chemical structures from step (b)(i) having a region similar to the criteria data set; or (ii) the constructed model from step (b)(ii).

The present invention further provides a method for evaluating the ability of a compound to interact with IR and/or IGF-1R, the method comprising the steps of: (a) employing computational means to perform a fitting operation between the compound and the binding surface of a computer model of the low affinity binding site for insulin on IR ectodomain, and/or the low affinity binding site for IGF on IGF-1R ectodomain, using atomic coordinates wherein the root mean square deviation between the atomic coordinates and a subset of atomic coordinates of one or more of Appendixes I to VI or a subset of atomic coordinates of one or more thereof at least representing the C-terminal region of the α-chain of IR, the C-terminal region of the α-chain of IGF-1R, or a mimetic of the C-terminal region of the α-chain of IR and/or IGF-1R, is not more than 1.5 Å; and (b) analysing the results of the fitting operation to quantify the association between the compound and the binding surface model.

The present invention also provides a method of using molecular replacement to obtain structural information about a molecule or a molecular complex of unknown structure, comprising the steps of: (i) generating an X-ray diffraction pattern of the crystallized molecule or molecular complex; and (ii) applying the atomic coordinates of one or more of Appendixes I to VI, or a subset of atomic coordinates of one or more thereof at least representing the C-terminal region of the α-chain of IR, the C-terminal region of the α-chain of IGF-1R, or a mimetic of the C-terminal region of the α-chain of IR and/or IGF-1R, to the X-ray diffraction pattern to generate a three-dimensional electron density map of at least a region of the molecule or molecular complex whose structure is unknown.

The present invention provides a compound that binds to IR and/or IGF-1R ectodomain designed, redesigned or modified using the methods, of the invention. Preferably, such compounds have an affinity ($K_d$) for IR and/or IGF-1R of less than $10^{-5}$ M. In a particularly preferred embodiment, the compound binds to the low affinity binding site of IR and/or to the low affinity binding site of IGF-1R.

The present invention also provides an isolated peptide or mimetic thereof which binds the L1 domain of IR and/or the L1 domain of IGF-1R, the peptide comprising: (i) an amino acid sequence as provided in SEQ ID NO: 13 or SEQ ID NO: 15; (ii) an amino acid sequence which is at least 50% identical, more preferably at least 80% identical, more preferably at least 90% identical, more preferably at least 95% identical, to SEQ ID NO: 13 and/or SEQ ID NO: 15; or (iii) a fragment of i) or ii) which binds the L1 domain of IR and/or the L1 domain of IGF-1R, wherein the peptide has a helical structure.

Further provided is an isolated polynucleotide encoding the isolated peptide or mimetic thereof, as well as a vector comprising said polynucleotide and a host cell comprising said vector.

The present invention also provides a composition comprising a compound of the invention, a peptide or mimetic of the invention, and/or a polynucleotide of the invention, and optionally an acceptable carrier or diluent, more preferably a pharmaceutically acceptable carrier or diluent.

The present invention further provides a method for preventing or treating a disease associated with aberrant IR and/or IGF-1R functioning and/or signalling, the method comprising administering to a subject in need thereof a compound of the invention, a peptide or mimetic of the invention, and/or a polynucleotide of the invention.

Also provided by the present invention is use of a compound of the invention, a peptide or mimetic of the invention, and/or a polynucleotide of the invention, for the manufacture of a medicament for treating a disease in a subject associated with aberrant IR and/or IGF-1R functioning and/or signalling.

Examples of diseases associated with aberrant IR and/or IGF-1R functioning and/or signalling include, but are not limited to, obesity, type I and type II diabetes, cardiovascular disease, osteoporosis, dementia and cancer.

It is also intended that embodiments of the present invention include manufacturing steps such as incorporating the compound, such as a peptide, into a pharmaceutical composition in the manufacture of a medicament.

Throughout this specification, preferred aspects and embodiments apply, as appropriate, separately, or in combination, to other aspects and embodiments, mutatis mutandis, whether or not explicitly stated as such.

The present invention will now be described further with reference to the following examples, which are illustrative only and non-limiting.

FIG. 1: Shows the sequence alignment of the ectodomains of human insulin receptor (IR, exon 11-isoform) and human IGF1 receptor (IGF-1R). Residues conserved between the sequences are indicated by vertical bars and potential N-linked glycosylation sites are indicated by shading. Disulphide links are indicated by square braces above the alignment. Sequence sources were: IR (Ullrich et al., 1985), human type 1 IGF receptor (Ullrich et al., 1986).

Figure 2:
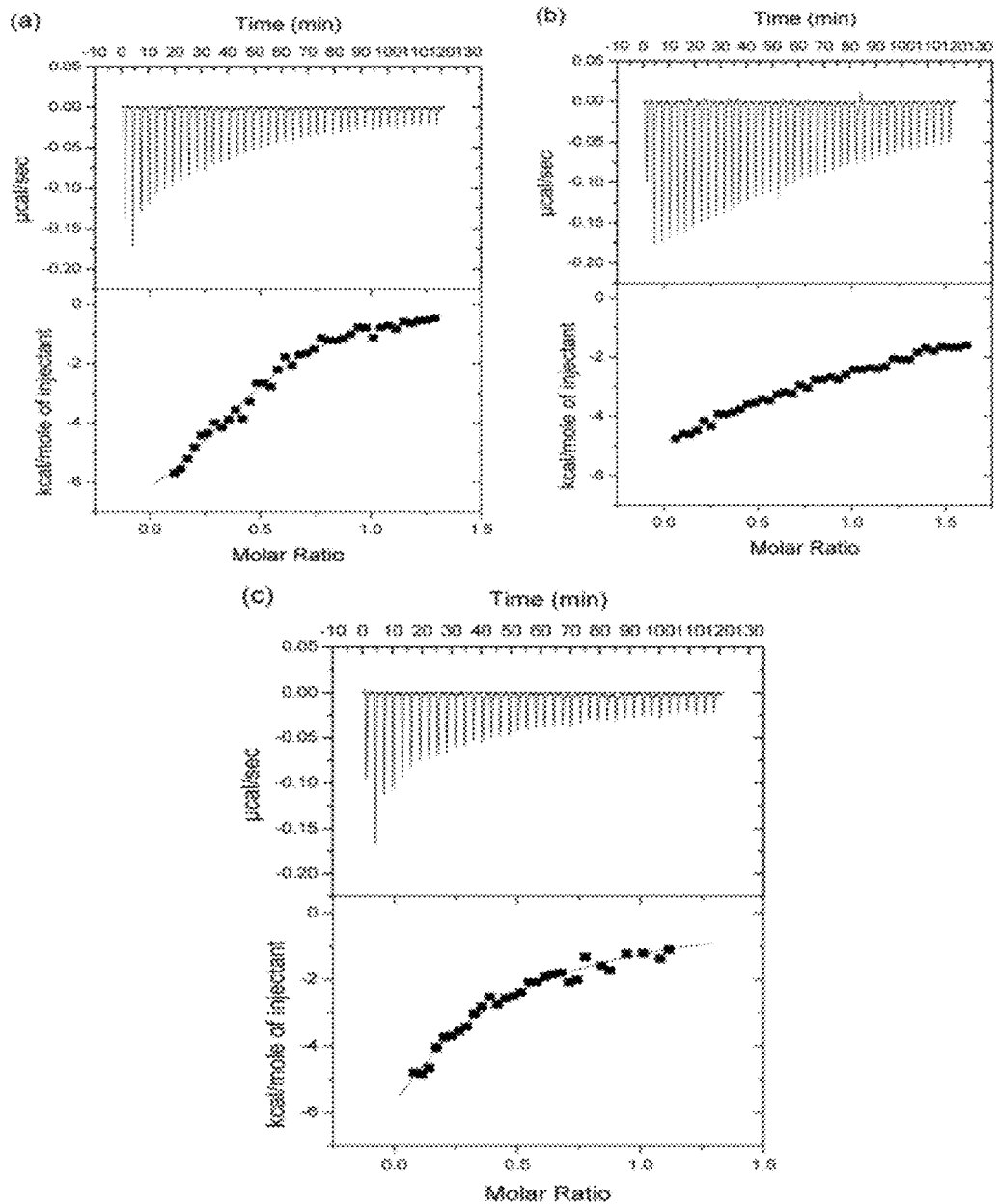

FIG. 2. ITC curves for the titration of (a) IR classical αCT peptide against IR485, (b) IGF-1R classical αCT peptide against IR485, and (c) IR classical αCT.714A peptide against IR485.

Figure 3:
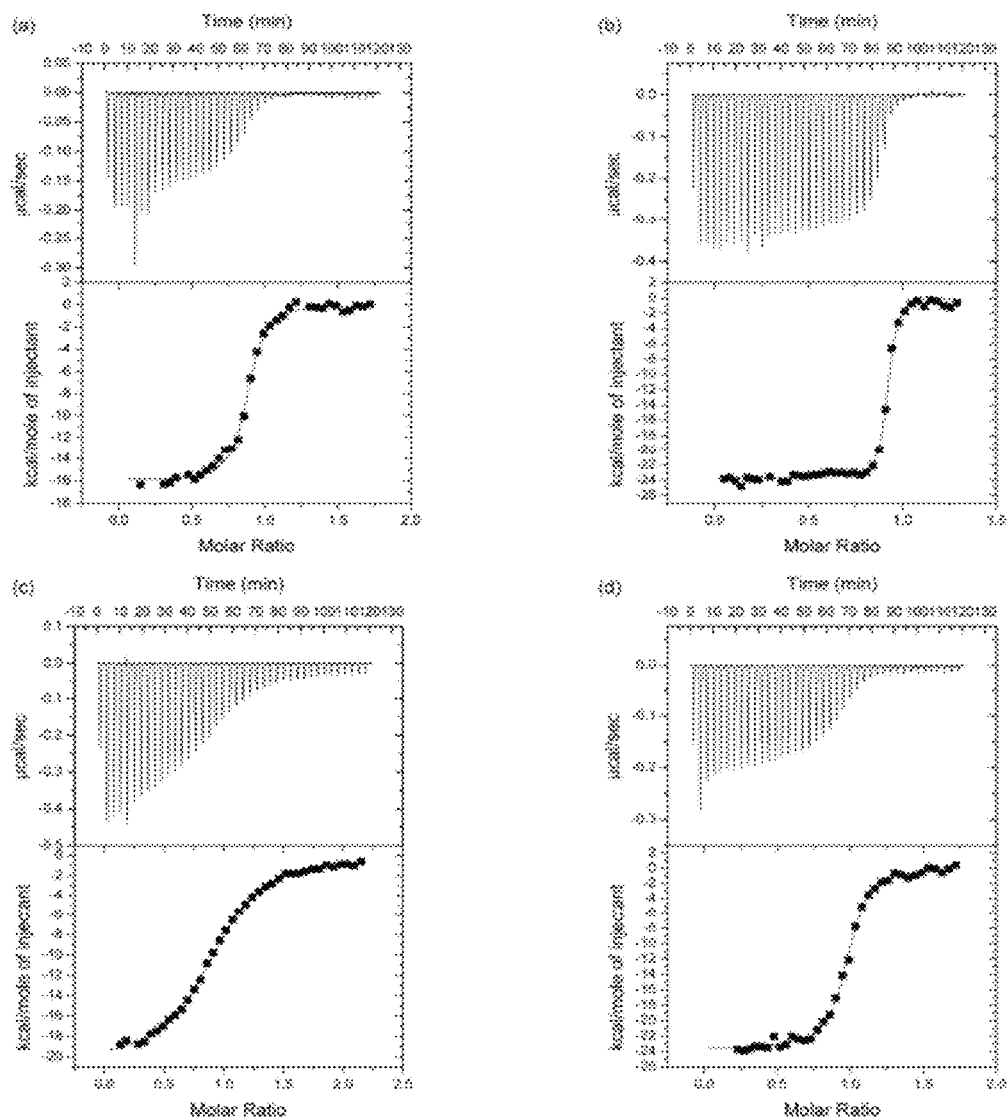

FIG. 3. ITC curves for the titration of (a) ZFP-insulin against IR485 pre-complexed with a 10-fold molar ratio of IR classical αCT peptide, (b) ZFP-insulin against IR485 pre-complexed with a 10-fold molar ratio of IGF-1R classical αCT peptide, (c) IGF-1R against IR485 pre-complexed with a 10-fold molar ratio of IR classical αCT peptide, and (d) IGF-1R against IR485 pre-complexed with a 10-fold molar ratio of IGF-1R classical αCT peptide.

Figure 4:
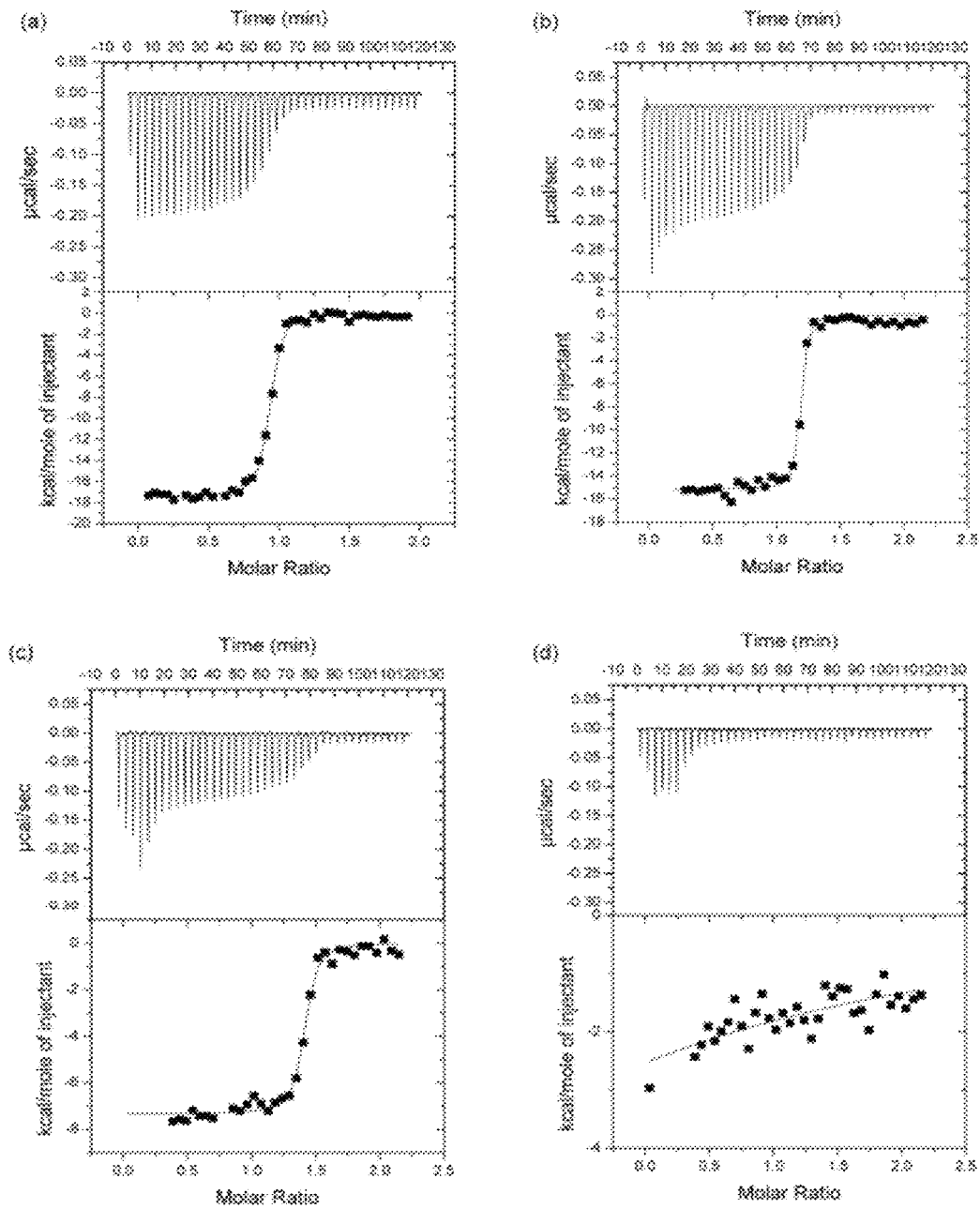

FIG. 4. ITC curves for the titration of (a) S519C16 against IR485, (b) S519C16 against IR485 pre-complexed with a 10-fold molar ratio of IR classical αCT peptide, (c) S519N20 against IR485, and (d) 5519 against IR485.

Figure 5:
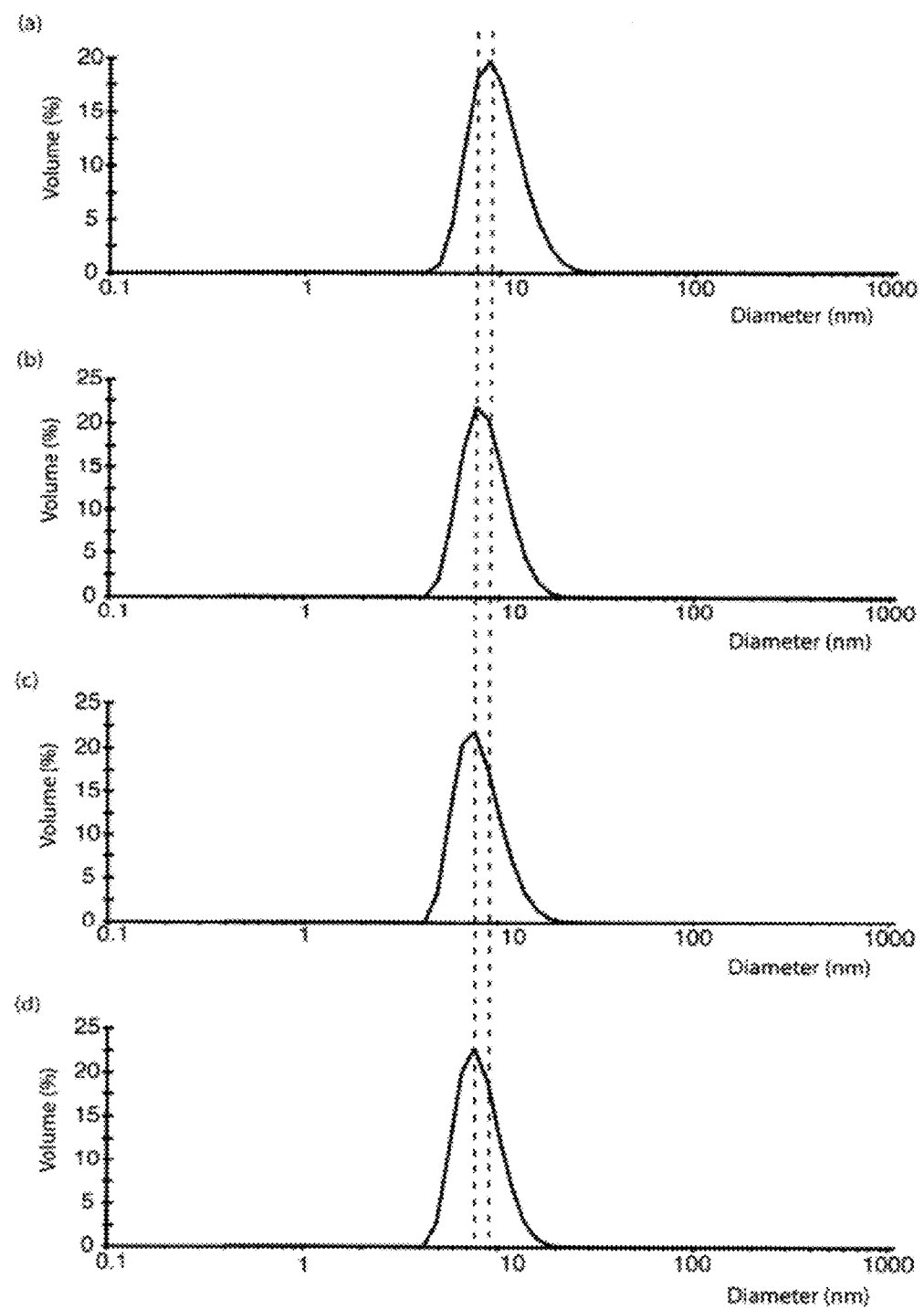

FIG. 5. Dynamic light scattering volume distribution curves obtained from samples of (a) IR485 at 6 mg/ml, (b) IR485 at 0.5 mg/ml, (c) IR485 at 6 mg/ml plus a 3-fold molar ratio of IR αCT peptide, (d) IR485 at 6 mg/ml plus a 3-fold molar ratio of IR classical αCT peptide and a 2-fold molar ratio of ZFP-insulin.

Figure 6:
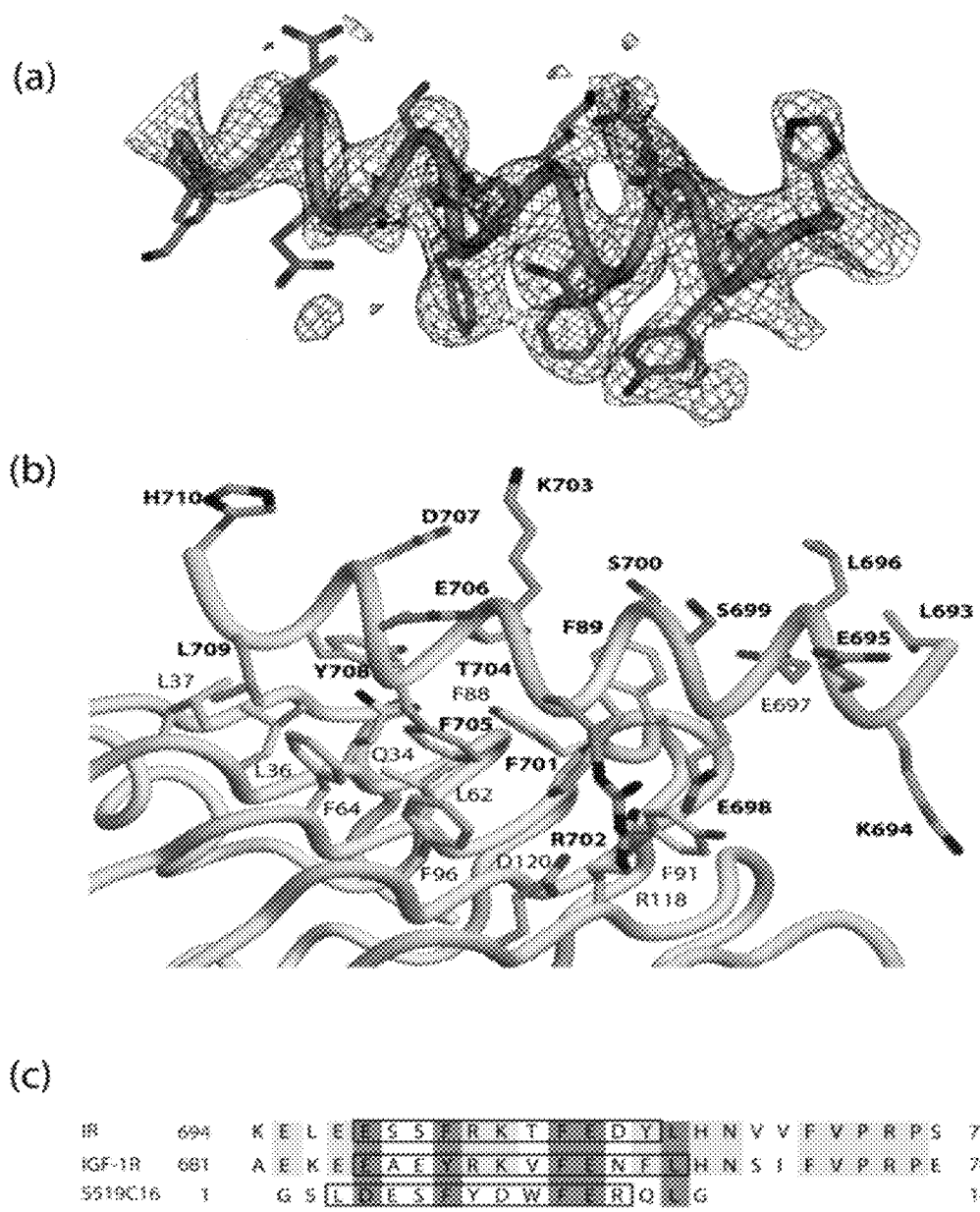

FIG. 6. The crystal structure of IR ectodomain comprising the C-terminal region of the α-chain of IR. (a) Negative B-factor enhanced ($F_o$-$F_c$) electron density overlaid with the final model of IR residues 693-710; (b) Detail of the interaction between IR residues 693-710 (yellow backbone, green carbons, non-bold numbering) and the surface of L1-β2 (pink backbones; cyan carbons, bold numbering); (c) Sequence alignment of the C-terminal regions of the α-chains of IR and IGF-1R and the S519C16 peptide (Menting et al., 2009). Shaded regions show, conservation between the three sequences and boxed regions show segments predicted to be helical in conformation (Menting et al., 2009).

Figure 7:
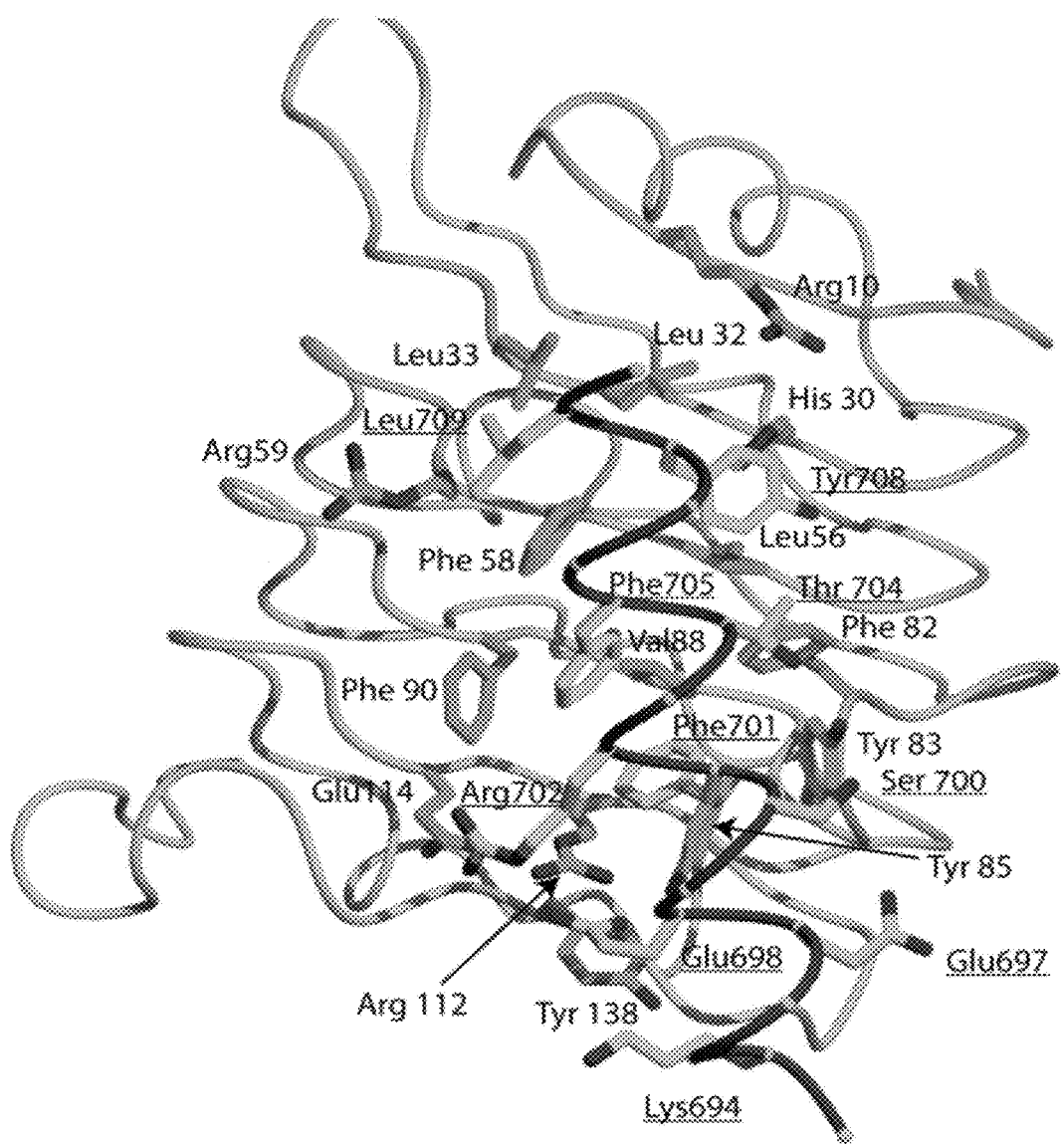

FIG. 7. Model structure of the C-terminal region of IR α-chain bound to the L1 domain of IGF-1R (Appendix II) generated from the crystal structure of IR ectodomain inclusive of residues 693-710. The backbone of the respective L1 domain is shown as an orange coil, the side chains of residues within the L1 domain that interact with the respective bound peptide are shown with green carbon atoms, red oxygen atoms and blue nitrogen atoms, and the backbone of the bound peptide helix is shown as a blue coil. Selected peptide residues that interact with the L1 domain are shown with cyan carbon atoms, red oxygen atoms and blue nitrogen atoms. The remaining peptide residues, which have more limited or no interaction with the L1 domain are represented only by their α-carbon atoms shown as spheres embedded in the peptide coil, with other atoms within these residues omitted for clarity. Residues that lie in the C-terminal region of IR α-chain are underlined for clarity.

Figure 8:
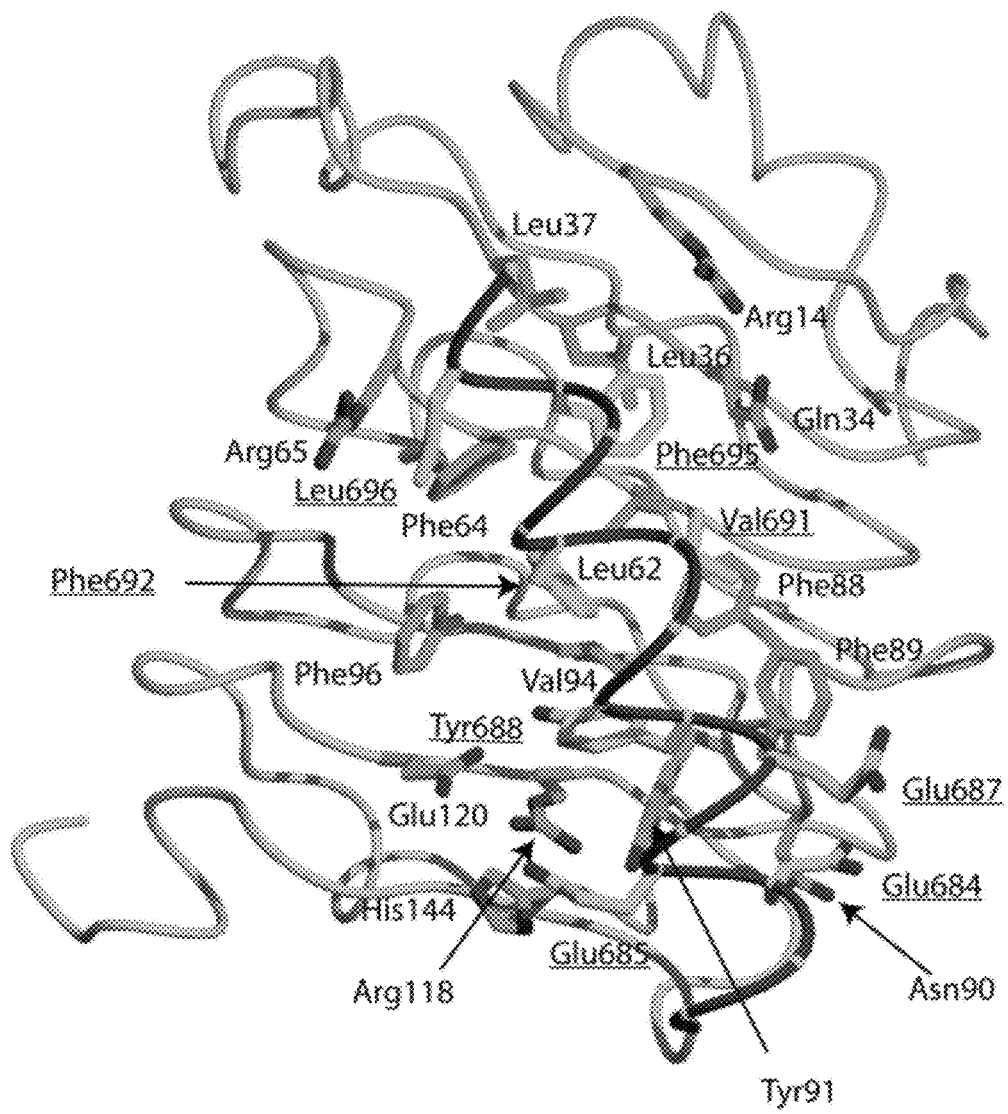

FIG. 8. Model structure of the C-terminal region of IGF-1R α-chain bound to the L1 domain of IR (Appendix III). Colouring and style is as described above for FIG. 7.

Figure 9:
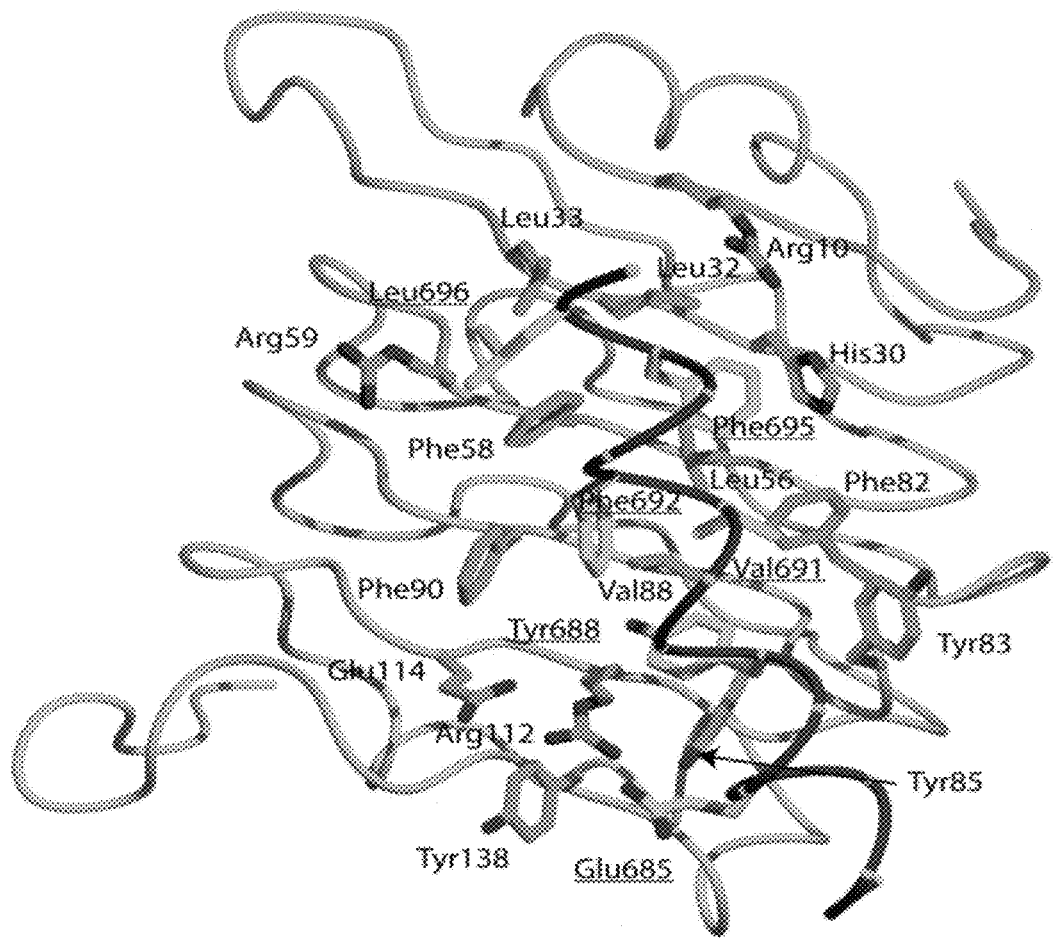

FIG. 9. Model structure of the C-terminal region of IGF-1R α-chain bound to the L1 domain of IGF-1R (Appendix IV). Colouring and style is as described above for FIG. 7.

Figure 10:
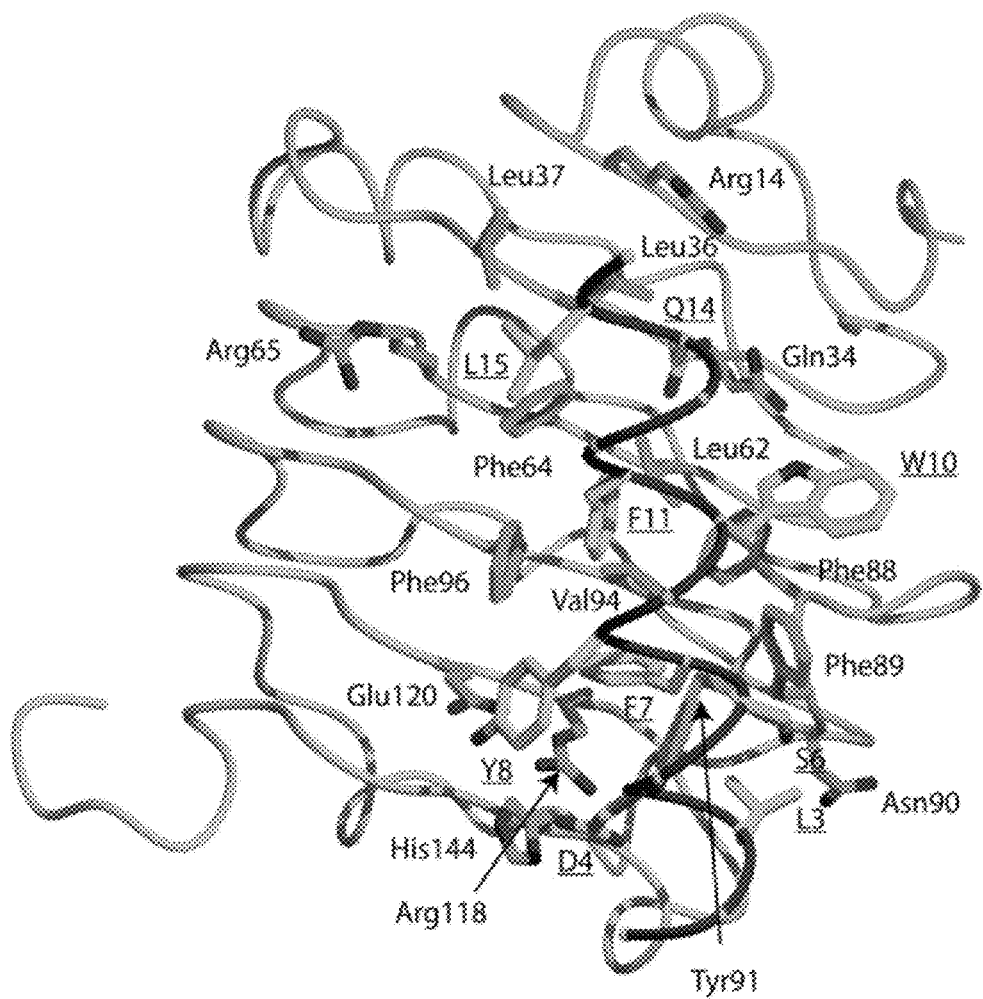

FIG. 10. Model structure of the S519C16 peptide bound to the L1 domain of IR (Appendix V). Colouring and style is as described above for FIG. 7.

Figure 11:
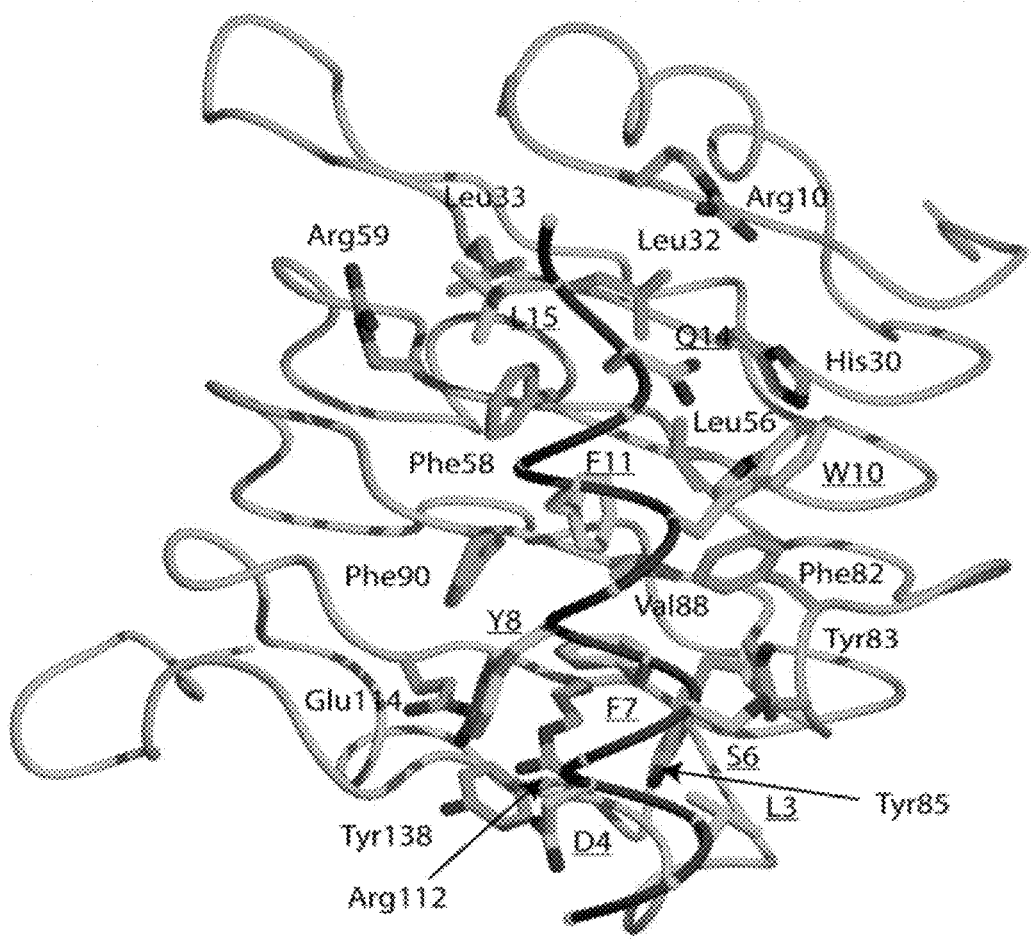

FIG. 11. Model structure of the S519C16 peptide bound to the L1 domain of IGF-1R (Appendix VI). Colouring and style is as described above for FIG. 7.

Figure 12:
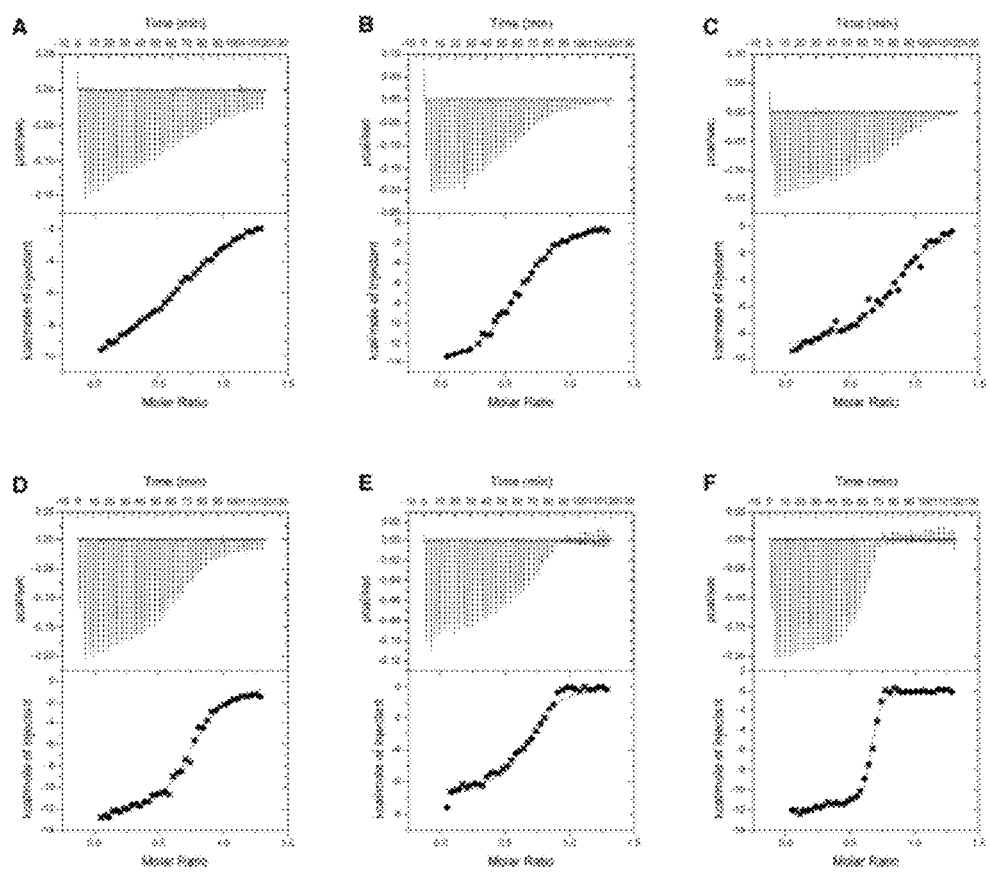

FIG. 12. Sample isothermal titration calorimetry curves obtained for the titration against insulin mini-receptor IR485 of N-terminally biotinylated αCT peptide 698-719 containing the following respective mutations: (A) wild type, (B) T704Y, (C) R702W, (D) R702Y, (E) T704W and (F) R702Y/T704W.

KEY TO THE SEQUENCE LISTING

SEQ ID NO: 1—Amino acid sequence of mature human insulin receptor ectodomain (isoform A).
SEQ ID NO: 2—Amino acid sequence of mature human insulin receptor ectodomain (isoform B).
SEQ ID NO: 3—Amino acid sequence of mouse insulin receptor.
SEQ ID NO: 4—Amino acid sequence of rhesus monkey insulin receptor, predicted.
SEQ ID NO: 5—Amino acid sequence of bovine insulin receptor, predicted.
SEQ ID NO: 6—Amino acid sequence of mature human insulin-like growth factor receptor 1 (IGF-1R) ectodomain.
SEQ ID NO: 7—Amino acid sequence of mouse insulin-like growth factor receptor 1 (IGF-1R).
SEQ ID NO: 8—Amino acid sequence of rhesus monkey insulin-like growth factor receptor 1 (IGF-1R), predicted.
SEQ ID NO: 9—Amino acid sequence of bovine insulin-like growth factor receptor 1 (IGF-1R), predicted.
SEQ ID NO: 10—Amino acid sequence of IR485.
SEQ ID NO: 11—Amino acid sequence of the classical α-chain C-terminal peptide (αCT) of human IR.
SEQ ID NO: 12—Amino acid sequence of the F714A mutant of the classical α-chain C-terminal peptide ('αCT') of human IR.
SEQ ID NO: 13—Amino acid sequence of the C-terminal region of the α-chain of human IR.
SEQ ID NO: 14—Amino acid sequence of the classical α-chain C-terminal peptide (αCT) of human IGF-1R.
SEQ ID NO: 15—Amino acid sequence of the C-terminal region of the α-chain of human IGF-1R.
SEQ ID NO: 16—Amino acid sequence of the S519 peptide.
SEQ ID NO: 17—Amino acid sequence of the S519N20 peptide.
SEQ ID NO: 18—Amino acid sequence of the S519C16 peptide.
SEQ ID NO:19—FYXWF motif.

DETAILED DESCRIPTION OF THE INVENTION

Unless defined otherwise, all technical and scientific terms used herein have the same meaning as commonly understood by one of ordinary skill in the art (e.g. in molecular biology, biochemistry, structural biology, and computational biology). Standard techniques are used for molecular and biochemical methods (see generally, Sambrook et al., 2001, and Ausubel et al., 1999, which are incorporated herein by reference) and chemical methods.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

IR Ectodomain Crystals and Crystal Structure

The present invention provides a crystal comprising a C-terminal region of the IR α-chain based on the IRΔβ construct (see Examples).

As used herein, the term "crystal" means a structure (such as a three dimensional (3D) solid aggregate) in which the plane faces intersect at definite angles and in which there is a regular structure (such as internal structure) of the constituent chemical species. The term "crystal" refers in particular to a solid physical crystal form such as an experimentally prepared crystal.

Crystals according to the invention may be prepared using any IR ectodomain, i.e. the IR polypeptide containing the extracellular domain and lacking the transmembrane domain and the intracellular tyrosine kinase domain. Typically, the extracellular domain comprises residues 1 to 917 (mature receptor numbering) of human IR, or the equivalent thereof together with any post-translational modifications of these residues such as N- or O-linked glycosylation.

In a preferred embodiment the IR polypeptide is human IR (SEQ ID NOs: 1 and 2). However, the IR polypeptide may also be obtained from other species, such as other mammalian, vertebrate or invertebrate species. Examples of IR polypeptides from other species are given in SEQ ID NOs: 3 to 5.

Crystals may be constructed with wild-type IR polypeptide ectodomain sequences or variants thereof, including allelic variants and naturally occurring mutations as well as genetically engineered variants. Typically, variants have at least 95 or 98% sequence identity with a corresponding wild-type IR ectodomain polypeptide.

Optionally, the crystal of IR ectodomain may comprise one or more molecules which bind to the ectodomain, or otherwise soaked into the crystal or cocrystallised with IR ectodomain. Such molecules include ligands or small molecules, which may be candidate pharmaceutical agents intended to modulate the interaction between IR and its biological targets. The crystal of IR ectodomain may also be a molecular complex with other receptors of the IGF receptor family such as IGF-1R. The complex may also comprise additional molecules such as the ligands to these receptors.

The production of IR ectodomain crystals is described below.

In a preferred embodiment, an IR ectodomain crystal of the invention comprising the C-terminal segment of the IR α-chain has the atomic coordinates set forth in Appendix I. As used herein, the term "atomic coordinates" or "set of coordinates" refers to a set of values which define the position of one or more atoms with reference to a system of axes. It will be understood by those skilled in the art that atomic coordinates may be varied, without affecting significantly the accuracy of models derived therefrom. Thus, although the invention provides a very precise definition of a preferred atomic structure, it will be understood that minor variations are envisaged and the claims are intended to encompass such variations.

It will be understood that any reference herein to the atomic coordinates or subset of the atomic coordinates shown in Appendix I shall include, unless specified otherwise, atomic coordinates having a root mean square deviation of backbone atoms of not more than 1.5 Å, preferably not more than 1 Å, when superimposed on the corresponding backbone atoms described by the atomic coordinates shown in Appendix I. Also, any reference to the atomic coordinates or subset of the atomic coordinates shown in Appendixes II to VI shall include, unless specified otherwise, atomic coordinates having a root mean square deviation of backbone atoms of not more than 2.5 Å when superimposed on the corresponding backbone atoms described by the atomic coordinates shown in Appendixes II to VI.

The following defines what is intended by the term "root mean square deviation (RMSD)" between two data sets. For each element in the first data set, its deviation from the corresponding item in the second data set is computed. The squared deviation is the square of that deviation, and the mean squared deviation is the mean of all these squared deviations. The root mean square deviation is the square root of the mean squared deviation.

Preferred variants are those in which the RMSD of the x, y and z coordinates for all backbone atoms other than hydrogen is less than 1.5 Å (preferably less than 1 Å, 0.7 Å or less than 0.3 Å) compared with the coordinates given in Appendix I. It will be readily appreciated by those skilled in the art that a 3D rigid body rotation and/or translation of the atomic coordinates does not alter the structure of the molecule concerned.

In a highly preferred embodiment, the crystal has the atomic coordinates as shown in Appendix I.

The present invention also provides a crystal structure of the low affinity insulin binding site of IR ectodomain polypeptide comprising the C-terminal region of the IR α-chain, or a region thereof.

The atomic coordinates obtained experimentally for amino acids 4 to 655, 693 to 710 (the "C-terminal region of the IR α-chain"), and 755 to 909 of human IR-A (mature receptor numbering; SEQ ID NO: 1) are shown in Appendix I. However, a person skilled in the art will appreciate that a set of atomic coordinates determined by X-ray crystallography is not without standard error. Accordingly, any set of structure coordinates for an IR ectodomain polypeptide comprising the C-terminal region of the IR α-chain that has a root mean square deviation of protein backbone atoms of less than 0.75 Å when superimposed (using backbone atoms) on the atomic coordinates listed in Appendix I shall be considered identical.

The present invention also comprises the atomic coordinates of the C-terminal region of the IR α-chain that substantially conforms to the atomic coordinates listed in Appendix I.

A structure that "substantially conforms" to a given set of atomic coordinates is a structure wherein at least about 50% of such structure has an RMSD of less than about 1.5 Å for the backbone atoms in secondary structure elements in each domain, and more preferably, less than about 1.3 Å for the backbone atoms in secondary structure elements in each domain, and, in increasing preference, less than about 1.0 Å, less than about 0.7 Å, less than about 0.5 Å, and most preferably, less than about 0.3 Å for the backbone atoms in secondary structure elements in each domain.

In a more preferred embodiment, a structure that substantially conforms to a given set of atomic coordinates is a structure wherein at least about 75% of such structure has the recited RMSD value, and more preferably, at least about 90% of such structure has the recited RMSD value, and most preferably, about 100% of such structure has the recited RMSD value.

In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

The present invention also provides a preferred subset of the atomic coordinates listed in Appendixes I and II comprising the C-terminal region of the IR ectodomain α-chain spanning residues 693 to 710 (SEQ ID NO: 13).

As used herein, the term "IR ectodomain" refers to the extracellular domain of IR lacking the transmembrane domain and the intracellular tyrosine kinase domain of IR, typically comprising residues 1 to 917 (mature IR-A receptor numbering) of human. IR, or the equivalent thereof, together with any post-translational modifications of these residues such as N- or O-linked glycosylation.

As used herein, the term "low affinity binding site" for IR means the regions of IR involved in forming the low affinity binding site (also known as "Site 1") of IR for insulin, comprising the C-terminal region of the IR α-chain and additionally one or both of the L1 domain of IR and the CR domain of IR. Insulin binding to the low affinity binding site of IR induces formation of the high affinity insulin binding site of IR and subsequent signal transduction.

As used herein, the term "C-terminal region" of the IR α-chain refers to amino acids 693-710 of isoform A (IR-A) of the human IR α-chain as given in SEQ ID NO: 13, with numbering according to mature isoform A of human IR (SEQ ID NO: 1). However, a person skilled in the art will appreciate that the corresponding region (amino acids 693-710) of the IR α-chain from isoform B of the mature human IR (SEQ ID NO: 2) could alternatively be used in the present invention.

As used herein, the term "classical α-chain C-terminal peptide", or "αCT", refers in IR to a region of the C-terminal α-chain of IR previously described in the literature as being important for, insulin binding (Kurose et al., 1994; Kristensen et al, 2002), and comprising amino acids 704-719 (mature IR-A receptor numbering) as given in SEQ ID NO: 11.

As used herein, the term "leucine-rich repeat domain 1" or "L1 domain" refers in IR to a leucine-rich domain comprising amino acids 1-156 of mature human IR (SEQ ID NO: 1). The L1 domain of IR comprises a central β-sheet, which comprises amino acids selected from 10-15, 32-37, 60-65, 88-97, 116-121 and 142-147 of mature human IR (SEQ ID NO: 1).

As used herein, the term "leucine-rich repeat domain 2" or "L2 domain" refers in IR to a leucine-rich domain comprising amino acids 310-469 of mature human IR (SEQ ID NO: 1).

As used herein, the term "loop in the fourth leucine-rich repeat (LRR) rung of the L1 domain", or variations thereof, refers in IR to a leucine-rich domain comprising amino acids 85-91 of mature human IR (SEQ ID NO: 1).

As used herein, the term "cysteine-rich domain" or "CR domain" refers in IR to a cysteine-rich domain comprising amino acids 157-309 of mature human IR (SEQ ID NO: 1).

The CR domain contains many different modules. As used herein, the term "module 6 of the CR domain" refers in IR to amino acids 256-286 of mature human IR (SEQ ID NO: 1).

IGF-1R Ectodomain Structure

Due to the high sequence homology and structural similarity between IR and IGF-1R, the present invention also provides a model for the C-terminal region of IGF-1R α-chain as it associates with IGF-1R to form the low affinity IGF binding site. The present invention provides a preferred subset of the atomic coordinates listed in Appendixes III and IV comprising the C-terminal region of the IGF-1R ectodomain α-chain spanning residues 681-697 (SEQ ID NO: 15).

As used herein, the term "IGF-1R ectodomain" refers to the extracellular domain of IGF-1R lacking the transmembrane domain and the intracellular tyrosine kinase domain of IGF-1R, typically comprising residues 1 to 905 (mature receptor numbering) of human IGF-1R, or the equivalent, thereof, together with any post-translational modifications of these residues such as N- or O-linked glycosylation.

As used herein, the term "low affinity binding site" for IGF-1R means the regions of IGF-1R involved in forming the low affinity binding site (also known as "Site 1") of IGF-1R for IGF, comprising the C-terminal region of the IGF-1R α-chain and additionally one or both of the L1 domain of IGF-1R and the CR domain of IGF-1R. IGF binding to the low affinity binding site of IGF-1R induces formation of the high affinity IGF binding site of IGF-1R and subsequent signal transduction.

As used herein, the term "C-terminal region" of the IGF-1R α-chain refers to amino acids 681-697 of human IGF-1R α-chain as given in SEQ ID NO: 15, with numbering according to mature human IGF-1R (SEQ ID NO: 6).

As used herein, the term "classical α-chain C-terminal peptide", or "αCT", refers in IGF-1R to a region of IGF-1R corresponding to the C-terminal α-chain of IR previously described in the literature as being important for insulin binding (Kurose et al., 1994; Kristensen et al, 2002), and comprising amino acids 691-706 of IGF-1R (mature IGF-1R numbering) as given in SEQ ID NO: 14.

As used herein, the term "leucine-rich repeat domain 1" or "L1 domain" refers in IGF-1R to a leucine-rich domain comprising amino acids 1-149 of mature human IGF-1R (SEQ ID NO: 6).

As used herein, the term "leucine-rich repeat domain 2" or "L2 domain" refers in IGF-1R to a leucine-rich domain comprising amino acids 300-459 of mature human IGF-1R (SEQ ID NO: 6).

As used herein, the term "that part of the second LRR containing Ser35" refers in IGF-1R to amino acids 35-41 of mature human IGF-1R (SEQ ID NO: 6).

As used herein, the term "cysteine-rich domain" or "CR domain" refers in IGF-1R to a cysteine-rich domain comprising amino acids 150-299 of mature human IGF-1R (SEQ ID NO: 6). The CR domain contains many different modules. As used herein, the term "module 6 of the CR domain" refers to amino acids 249-275 of mature human IGF-1R (SEQ ID NO: 6).

Manipulation of the Atomic Coordinates of the Invention

It will be appreciated that a set of atomic coordinates for a polypeptide is a relative set of points that define a shape in three dimensions. Thus, it is possible that an entirely different set of coordinates could define a similar or identical shape. Moreover, slight variations in the individual coordinates will have little effect on overall shape.

The variations in coordinates may be generated due to mathematical manipulations of the atomic coordinates. For example, the atomic coordinates set forth in Appendix I could be manipulated by crystallographic permutations of the atomic coordinates, fractionalisation of the atomic coordinates, integer additions or subtractions to sets of the structure coordinates, inversion of the atomic coordinates, or any combination thereof.

Alternatively, modification in the crystal structure due to mutations, additions, substitutions, and/or deletions of amino acids, or other changes in any of the components that make up the crystal could also account for variations in atomic coordinates.

Various computational analyses are used to determine whether a molecular complex or a portion thereof is sufficiently similar to all or parts of the structure of the extracellular domain of IR described above. Such analyses may be carried out in current software applications, such as the *Sequoia* program (Bruns et al., 1999).

The Molecular Similarity program permits comparisons between different structures, different conformations of the same structure, and different parts of the same structure.

Comparisons typically involve calculation of the optimum translations and rotations required such that the root mean square deviation of the fit over the specified pairs of equivalent atoms is an absolute minimum. This number is given in Angstroms.

Accordingly, atomic coordinates of an IR and/or IGF-1R ectodomain comprising the low affinity binding site of the present invention include atomic coordinates related to the atomic coordinates listed in Appendixes I to VI by whole body translations and/or rotations. Accordingly, RMSD values listed above assume that at least the backbone atoms of the structures are optimally superimposed which may require translation and/or rotation to achieve the required optimal fit from which to calculate the RMSD value.

A three dimensional structure of an IR and/or IGF-1R ectodomain polypeptide or region thereof which substantially conforms to a specified set of atomic coordinates can be modelled by a suitable modeling computer program such as MODELLER (Sali & Blundell, 1993), using information, for example, derived from the following data: (1) the amino acid sequence of the human IR and/or IGF-1R ectodomain polypeptide; (2) the amino acid sequence of the related portion(s) of the protein represented by the specified set of atomic coordinates having a three dimensional configuration; and, (3) the atomic coordinates of the specified three dimensional configuration. A three dimensional structure of an IR and/or IGF-1R ectodomain polypeptide which substantially conforms to a specified set of atomic coordinates can also be calculated by a method such as molecular replacement, which is described in detail below.

Atomic coordinates are typically loaded onto a machine-readable medium for subsequent computational manipulation. Thus models and/or atomic coordinates are advantageously stored on machine-readable media, such as magnetic or optical media and random-access or read-only memory, including tapes, diskettes, hard disks, CD-ROMs and DVDs, flash memory cards or chips, servers and the interne. The machine is typically a computer.

The atomic coordinates may be used in a computer to generate a representation, e.g. an image, of the three-dimensional structure of the IR and/or IGF-1R ectodomain crystal which can be displayed by the computer and/or represented in an electronic file.

The atomic coordinates and models derived therefrom may also be used for a variety of purposes such as drug discovery, biological reagent (binding protein) selection and X-ray crystallographic analysis of other protein crystals.

Molecular Replacement/Binding

The structure coordinates of IR and/or IGF-1R comprising the C-terminal region of the α-chain, such as those set forth in Appendixes I to IV, can also be used for determining the three-dimensional structure of a molecular complex which contains at least the C-terminal region of the α-chain of IR and/or IGF-1R. In particular, structural information about another crystallised molecular complex may be obtained. This may be achieved by any of a number of well-known techniques, including molecular replacement.

Methods of molecular replacement are generally known by those of skill in the art (generally described in Brunger, 1997; Navaza & Saludjian, 1997; Tong & Rossmann, 1997; Bentley, 1997; Lattman, 1985; Rossmann, 1972; McCoy, 2007).

Generally, X-ray diffraction data are collected from the crystal of a crystallised target structure. The X-ray diffraction data is transformed to calculate a Patterson function. The Patterson function of the crystallised target structure is compared with a Patterson function calculated from a known structure (referred to herein as a search structure). The Patterson function of the search structure is rotated on the target structure Patterson function to determine the correct orientation of the search structure in the crystal. A translation function is then calculated to determine the location of the search structure with respect to the crystal axes. Once the search structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and beta-strands or beta-sheets) of the search molecule are related to the crystallised target structure.

The electron density map can, in turn, be subjected to any well-known model building and structure refinement techniques to provide a final, accurate structure of the unknown (i.e. target) crystallised molecular complex (e.g. see Jones et al., 1991; Brünger et al., 1998).

Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory starting estimate of the phases for the unknown structure.

By using molecular replacement, all or part of the structure coordinates of IR and/or IGF-1R comprising the C-terminal region of the α-chain provided herein (and set forth in Appendixes I to IV) can be used to determine the structure of a crystallised molecular complex whose structure is unknown more rapidly and efficiently than attempting to determine such information ab initio. This method is especially useful in determining the structure of IR and/or IGF-1R mutants and homologues.

The structure of any portion of any crystallised molecular complex that is sufficiently homologous to any portion of the extracellular domain of IR and/or IGF-1R can be solved by this method.

Such structure coordinates are also particularly useful to solve the structure of crystals of IR and/or IGF-1R co-complexed with a variety of molecules, such as chemical entities. For example, this approach enables the determination of the optimal sites for the interaction between chemical entities, and the interaction of candidate IR and/or IGF-1R agonists or antagonists.

All of the complexes referred to above may be studied using well-known X-ray diffraction techniques and may be refined against 1.5-3.5 Å resolution X-ray data to an R value of about 0.25 or less using computer software, such as X-PLOR (Yale University, distributed by Molecular Simulations, Inc.; see Brünger, 1996). This information may thus be used to optimize known IR and/or IGF-1R agonist/antagonists, such as anti-IR and/or anti-IF-1R antibodies, and more importantly, to design new or improved IR and/or IGF-1R agonists/antagonists.

Target Sites for Compound Identification, Design or Screening

The three-dimensional structure of the low affinity binding site of IR and/or IGF-1R provided by the present invention (Appendixes I to IV) can be used to identify potential target binding sites in the low affinity insulin binding site of IR and/or IGF-1R (i.e. to identify those regions of the low affinity binding site of IR and/or IGF-1R involved in and important to the binding of insulin and/or IGF and subsequent signal transduction) as well as in methods for identifying or designing compounds which interact with the low affinity binding site of IR and/or IGF-1R e.g. potential modulators of IR and/or IGF-1R.

The three-dimensional structure of IR and/or IGF-1R provided by the present invention (Appendixes I to IV) can be used to identify potential target binding sites in the L1 domain of IR and/or IGF-1R important for binding to the C-terminal region of the IR and/or IGF-1R α-chain (i.e. to identify those regions of the L1 domain of IR and/or IGF-1R involved in and important to the binding of C-terminal region of the IR and/or IGF-1R α-chain) as well as in methods for identifying or designing compounds which interact with the L1 domain of IR and/or IGF-1R in a manner similar to the C-terminal region of the IR and/or IGF-1R α-chain e.g. potential modulators of IR and/or IGF-1R.

The low affinity binding site of IR is a region of IR ectodomain involved in insulin docking to the receptor. Preferred low affinity target binding sites comprise the C-terminal region of the α-chain and one or more regions from the L1 domain and/or the CR domain of IR ectodomain. With regards to the L1 domain, the target binding site preferably comprises portions of the molecular surface of the central β-sheet of L1 and portions of the molecular surface of the second leucine-rich repeat (LRR) which contain Phe39 or the loop in the fourth LRR rung of L1, or preferably both, as defined above. With regards the CR domain, the target binding site preferably comprises module 6 of the CR domain, as defined above.

Alternatively; the low affinity target binding site in IR may comprise one or more amino acids from amino acids 693-710 (encompassing the C-terminal region of the IR α-chain) plus one or more of the following amino acid sequences: (i) amino acids 1-156; (ii) amino acids 157-310, and; (iii) amino acids 594 and 794.

With regards to amino acids 1-156, the target binding site preferably comprises at least one amino acid selected from Arg14, Asn15, Gln34, Leu36, Leu37, Phe39, Pro43, Phe46, Leu62, Phe64, Leu87, Phe88, Phe89, Asn90, Phe96, Glu97, Arg118, Glu120 or His 144.

With regards to amino acids 157-310, the target binding site preferably comprises at least one amino acid from the amino acid sequence 192-310, more preferably at least one amino acid from the sequence 227-303, yet more preferably least one amino acid selected from the sequence 259-284.

With regards to amino acids 594 and 794, the target binding site preferably comprises at least one amino acid selected from Asn594 or Arg794.

In a preferred embodiment, van der Waals and/or hydrophobic interactions account for the major portion of the binding energy between a compound and a low affinity insulin binding site of IR.

The three-dimensional structure of the C-terminal region of the IR α-chain provided by the present invention can also be used to identify or more clearly elucidate potential target binding sites on IGF-1R ectodomain (i.e. to identify those regions, or at least more accurately elucidate those regions, of IGF-1R ectodomain involved in and important to the binding of IGF and signal transduction) as well as in methods used for identifying or designing compounds which interact with potential target binding sites of IGF-1R ectodomain, e.g. potential modulators of IGF-1R.

Preferred target binding sites are those governing specificity, i.e. those regions of IGF-1R ectodomain involved in the initial low affinity binding of IGF (i.e. the initial binding of IGF to IGF-1R).

The low affinity binding site of IGF-1R is a region of IGF-1R ectodomain involved in IGF-I binding to the receptor. Preferred low affinity target binding sites comprise the C-terminal region of IGF-1R α-chain and one or more regions from the L1 domain and/or the CR domain of IGF-1R ectodomain. With regards to the L1 domain, the target binding site preferably comprises the central β-sheet of the L1 domain, and/or that part of the second LRR containing Ser35, and/or the loop in the fourth LRR rung of the L1 domain, or preferably all of these, as defined above. With regards the CR domain, the target binding site preferably comprises module 6 of the CR domain, as defined above.

Alternatively, the low affinity IGF binding site may comprise one or more amino acids from amino acids 681-697 (encompassing the C-terminal region of the IGF-1R α-chain) plus one or more amino acids from the following amino acid sequences: (i) amino acids 1-149; and (ii) amino acids 150-298.

With regards to amino acids 1-149, the target binding site preferably comprises at least one amino acid from the amino acid sequence 1-62, preferably 1-49, and more preferably amino acid sequence 23-49. With regards to amino acids 150-298, the target binding site preferably comprises at least one amino acid from the amino acid sequence 185-298, more preferably at least one amino acid from the sequence 220-294, yet more preferably least one amino acid selected from the sequence 252-273. The target binding site preferably comprises at least one amino acid selected from Arg10, His30, Leu32; Leu33, Leu56, Phe58, Arg59, Phe82, Tyr83, Asn84, Tyr85, Val88, Phe90, Arg112 and Asn136.

In a preferred embodiment, van der Waals and/or hydrophobic interactions account for the major portion of the binding energy between a compound and a low affinity binding site of IGF-1R.

Additional preferred binding sites in the case of both IR and IGF-1R, particularly for biological macromolecules such as proteins or aptamers, are those that are devoid of glycosylation or devoid of steric hindrance from glycan covalently attached to the polypeptide at sites in the spatial vicinity.

Design, Selection, Fitting and Assessment of Chemical Entities that Bind IR and/or IGF-1R Using a variety of known modelling techniques, the crystal structure of the present invention can be used to produce a model for the low affinity binding site of IR and/or IGF-1R, or at least part of the C-terminal region of the α-chain of IR or IGF-1R.

As used herein, the term "modelling" includes the quantitative and qualitative analysis of molecular structure and/or function based on atomic structural information and interaction models. The term "modelling" includes conventional numeric-based molecular dynamic and energy minimisation models, interactive computer graphic models, modified molecular mechanics models, distance geometry and other structure-based constraint models.

Molecular modelling techniques can be applied to the atomic coordinates of the low affinity binding site of IR and/or IGF-1R, or at least part of the C-terminal region of the α-chain of IR or IGF-1R, or a region thereof to derive a range of 3D models and to investigate the structure of binding sites, such as the binding sites of monoclonal antibodies, nonimmunoglobulin binding proteins and inhibitory peptides.

These techniques may also be used to screen for or design small and large chemical entities which are capable of binding IR and modulating the ability of IR to interact with extracellular biological targets, such as insulin or members of the IGF receptor family e.g. which modulate the ability of IR to heterodimerise. The screen may employ a solid 3D screening system or a computational screening system.

Such modelling methods are to design or select chemical entities that possess stereochemical complementary to the low affinity binding site of IR and/or IGF-1R, or to the regions of the L1 domain of IR and/or IGF-1R with which the C-terminal region of the α-chain of IR and/or IGF-1R interact. By "stereochemical complementarity" we mean that the compound or a portion thereof makes a sufficient number of energetically favourable contacts with the receptor as to have a net reduction of free energy on binding to the receptor.

Such stereochemical complementarity is characteristic of a molecule that matches intra-site surface residues lining the groove of the receptor site as enumerated by the coordinates set out in Appendix I, optionally also utilising the coordinates set out in Appendixes II to VI. By "match" we mean that the identified portions interact with the surface residues, for example, via hydrogen bonding or by non-covalent Van der Waals and Coulomb interactions (with surface or residue) which promote desolvation of the molecule within the site, in such a way that retention of the molecule at the binding site is favoured energetically.

It is preferred that the stereochemical complementarity is such that the compound has a $K_d$ for the receptor site of less than $10^{-4}$M, more preferably less than $10^{-5}$M and more preferably $10^{-6}$M. In a most preferred embodiment, the $K_d$ value is less than $10^{-8}$M and more preferably less than $10^{-9}$M.

Chemical entities which are complementary to the shape and electrostatics or chemistry of the receptor site characterised by amino acids positioned at atomic coordinates set out in Appendixes I to IV will be able to bind to the receptor, and when the binding is sufficiently strong, substantially prohibit the interaction of the IR and/or IGF-1R ectodomain with biological target molecules such as insulin or IGF.

It will be appreciated that it is not necessary that the complementarity between chemical entities and the receptor site extend over all residues of the receptor site in order to inhibit binding of a molecule or complex that naturally interacts with IR and/or IGF-1R ectodomain.

A number of methods may be used to identify chemical entities possessing stereochemical complementarity to the low affinity binding site of IR and/or IGF-1R, or to the regions of the L1 domain of IR and/or IGF-1R with which the C-terminal region of the α-chain of IR and/or IGF-1R interact. For instance, the process may begin by visual inspection of the entire low affinity insulin binding site comprising the C-terminal region of the α-chain of IR, or the equivalent region in IGF-1R, on the computer screen based on the coordinates in Appendixes I to IV generated from the machine-readable storage medium. Alternatively, selected fragments or chemical entities may then be positioned in a variety of orientations, or docked, within the low affinity binding site of IR and/or IGF-1R, or within the L1 domain of IR and/or IGF-1R in a manner similar to the C-terminal region of the α-chain of IR or IGF-1R, as defined supra. Similar methods could be used to identify chemical entities or compounds that may interact with the L1 domain of IR and/or IGF-1R in a manner similar to that of the C-terminal region of the α-chain of IR and/or IGF-1R.

Modelling software that is well known and available in the art may be used (Guida, 1994). These include Discovery Studio (Accelrys Software Inc., San Diego), SYBYL (Tripos Associates, Inc., St. Louis, Mo., 1992), Maestro (Schrödinger LLC, Portland), MOE (Chemical Computing Group Inc., Montreal, Canada). This modelling step may be followed by energy minimization with standard molecular mechanics force fields such as AMBER (Weiner et al., 1984), OPLS (Jorgensen and Tirado-Rives, 1988) and CHARMM (Brooks et al., 1983). In addition, there are a number of more specialized computer programs to assist in the process of selecting the binding moieties of this invention.

Specialised computer programs may also assist in the process of selecting fragments or chemical entities. These include, inter alia:

1. GRID (Goodford, 1985). GRID is available from Molecular Discovery Ltd., Italy.
2. AUTODOCK (Goodsell & Olsen, 1990). AUTODOCK is available from Scripps Research Institute, La Jolla, Calif.
3. DOCK (Kuntz et al., 1982). DOCK is available from University Of California, San Francisco, Calif.
4. GLIDE (Friesner et al., 2004). GLIDE is available from Schrödinger LLC, Portland.
5. GOLD (Cole et al., 2005). GOLD is avaible from The Cambridge Crystallographic Data Centre, Cambridge, UK.

Once suitable chemical entities or fragments have been selected; they can be assembled into a single compound. In one embodiment, assembly may proceed by visual inspection of the relationship of the fragments to each other on the three-dimensional image displayed on a computer screen in relation to the structure coordinates of the low affinity binding site of IR and/or IGF-1R, or the L1 domain to which the C-terminal region of the α-chain of IR or IGF-1R binds. This is, followed by manual model building using software such as Discovery Studio, Maestro, MOE or Sybyl. Alternatively, fragments may be joined to additional atoms using standard chemical geometry.

The above-described evaluation process for chemical entities may be performed in a similar fashion for chemical compounds.

Useful programs to aid one of skilled in the art in connecting the individual chemical entities or fragments include:

1. CAVEAT (Bartlett et al., 1989). CAVEAT is available from the University of California, Berkeley, Calif.
2. GANDI (Day and Caflisch, 2008). GANDI is available from the University of Zurich.

Other molecular modeling techniques may also be employed in accordance with this invention, see, e.g., Cohen et al. (1990) and Navia & Murcko (1992).

There are two preferred approaches to designing a molecule according to the present invention that complement the stereochemistry of the low affinity binding site of IR and/or IGF-1R, or the L1 domain to which the C-terminal region of the α-chain of IR or IGF-1R binds. The first approach is to in silico directly dock molecules from a three-dimensional structural database, to the target binding site, using mostly, but not exclusively, geometric criteria to assess the goodness-of-fit of a particular molecule to the site. In this approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule).

Flexibility of the receptor, IR or IGFR, can be incorporated into the in silico screening by the application of multiple conformations of the receptor (Totrov and Abagyan, 2008). The multiple conformations of the receptor can, be generated from the coordinates listed in Appendixes 1 to VI computationally by use of molecular dynamics simulation or similar approaches.

This approach is illustrated by Kuntz et al. (1982) and Ewing et al. (2001), the contents of which are hereby incorporated by reference, whose algorithm for ligand design is implemented in a commercial software package, DOCK version 4.0, distributed by the Regents of the University of California and further described in a document, provided by the distributor, which is entitled "Overview of the DOCK program suite" the contents of which are hereby incorporated by reference. Pursuant to the Kuntz algorithm, the shape of the cavity in which the C-terminal region of the α-chain of IR or IGF-1R fits is defined as a series of overlapping spheres of different radii. One or more extant databases of crystallographic data, such as the Cambridge Structural Database System (The Cambridge Crystallographic Data Centre, Cambridge, U.K.), the Protein Data Bank maintained by the Research Collaboratory for Structural Bioinformatics (Rutgers University, N.J., U.S.A.), LeadQuest (Tripos Associates, Inc., St. Louis, Mo.), Available Chemicals Directory (Symyx Technologies Inc.), and the NCI database (National Cancer Institute, U.S.A) is then searched for molecules which approximate the shape thus defined.

Molecules identified on the basis of geometric parameters, can then be modified to satisfy criteria associated with chemical complementarity, such as hydrogen bonding, ionic interactions and van der Waals interactions. Different scoring functions can be employed to rank and select the best molecule from a database. See for example Bohm & Stahl (1999). The software package FlexX, marketed by Tripos Associates, Inc. (St. Louis, Mo.) is another program that can be used in this direct docking approach (see Rarey et al., 1996).

The second preferred approach entails an assessment of the interaction of respective chemical groups ("probes") with the active site at sample positions within and around the site, resulting in an array of energy values from which three-dimensional contour surfaces at selected energy levels can be generated. The chemical-probe approach to ligand design is described, for example, by Goodford, (1985), the contents of which are hereby incorporated by reference, and is implemented in several commercial software packages, such as GRID (product of Molecular Discovery Ltd., Italy).

Pursuant to this approach, the chemical prerequisites for a site-complementing molecule are identified at the outset, by probing the active site with different chemical probes, e.g., water, a methyl group, an amine nitrogen, a carboxyl oxygen, or a hydroxyl. Favoured sites for interaction between the active site and each probe are thus determined, and from the resulting three-dimensional pattern of such sites a putative complementary molecule can be generated. This may be done either by programs that can search three-dimensional databases to identify molecules incorporating desired pharmacophore patterns or by programs which use the favoured sites and probes as input to perform de novo design. Suitable programs for determining and designing pharmacophores include CATALYST (Accelrys Software, Inc), and CERIUS2, DISCO (Abbott Laboratories, Abbott Park, Ill.; distributed by Tripos Associates Inc.).

The pharmacophore can be used to screen in silico compound libraries/three-dimensional databases, using a program such as CATALYST (Accelrys Software, Inc) and Sybyl/3 DB Unity (Tripos Associates, Inc., St. Louis, Mo.).

Databases of chemical structures are available from a number of sources including Cambridge Crystallographic Data Centre (Cambridge, U.K.), Molecular Design, Ltd., (San Leandro; CA), Tripos Associates, Inc. (St. Louis, Mo.), Chemical Abstracts Service (Columbus, Ohio), the Available Chemical Directory (Symyx Technologies, Inc.), the Derwent World Drug Index (WDI), BioByteMasterFile, the National Cancer Institute database (NCI), Medchem Database (BioByte Cortp.), and the Maybridge catalogue.

De novo design programs include LUDI (Accelrys Software Inc., San Diego, Calif.), Leapfrog (Tripos Associates, Inc.), and LigBuilder (Peking University, China).

Once an entity or compound has been designed or selected by the above methods, the efficiency with which that entity or compound may bind to IR and/or IGF-1R can be tested and optimised by computational evaluation. For example, a compound that has been designed or selected to function as an IR binding compound must also preferably traverse a volume not overlapping that occupied by the binding site when it is bound to the native IR. An effective IR binding compound must preferably demonstrate a relatively small difference in energy between its bound and free states (i.e., a small deformation energy of binding). Thus, the most efficient IR and/or IGF-1R binding compound should preferably be designed with a deformation energy of binding of not greater than about 10 kcal/mole, preferably, not greater than 7 kcal/mole. IR and/or IGF-1R binding compounds may interact with IR and/or IGF-1R in more than one conformation that are similar in overall binding energy. In those cases, the deformation energy of binding is taken to be the difference between the energy of the free compound and the average energy of the conformations observed when the compound binds to the protein.

A compound designed or selected as binding to IR and/or IGF-1R may be further computationally optimised so that in its bound state it would preferably lack repulsive electrostatic interaction with the target protein.

Such non-complementary (e.g., electrostatic) interactions include repulsive charge-charge, dipole-dipole and charge-dipole interactions. Specifically, the sum of all electrostatic interactions between the compound and the protein when the compound is bound to IR and/or IGF-1R, preferably make a neutral or favourable contribution to the enthalpy of binding.

Once an IR and/or IGF-1R-binding compound has been optimally selected or designed, as described above, substitutions may then be made in some of its atoms or side groups to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analysed for efficiency of fit to IR by the same computer methods described in detail above.

Specific computer software is available in the art to evaluate compound deformation energy and electrostatic interaction. Examples of programs designed for such uses include: Gaussian 03, (Frisch, Gaussian, Inc., Pittsburgh, Pa.); GAMESS (Gordon et al., Iowa State University); Jaguar (Schrödinger LLC, Portland); AMBER, version 9.0 (Case et al, University of California at San Francisco); CHARMM (Accelrys Software, Inc., San Diego, Calif.); and GROMACS version 4.0 (van der Spoel et al.).

The screening/design methods may be implemented in hardware or software, or a combination of both. However, preferably, the methods are implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system may also be considered to, be implemented as a computer-readable storage medium, configured with a computer program, where the storage medium so configured causes a computer to operate in a specific and predefined manner to perform the functions described herein.

Compounds

Compounds of the present invention include both those designed or identified using a screening method of the invention and those which are capable of recognising and binding to the low affinity binding sites of IR and/or IGF-1R, as defined above. Also encompassed by the present invention are compounds that bind to the L1 domain of IR and/or IGF-1R in a manner similar to that of the C-terminal region of the α-chain of IR and/or IGF-1R; i.e. compounds which mimic the C-terminal region of the α-chain of IR and/or IGF-1R.

Compounds capable of recognising and binding to the low affinity binding site of IR and/or IGF-1R may be produced using a screening method based on use of the atomic coordinates corresponding to the 3D structure of the low affinity binding site of IR and/or IGF-1R, or alternatively may be identified by screening against a specific target molecule which is indicative of the capacity to bind to the low affinity binding site of IR and/or IGF-1R.

Compounds capable of recognising and binding to the L1 domain of IR and/or IGF-1R in a manner similar to that of the C-terminal region of the α-chain of IR and/or IGF-1R (i.e. compounds which mimic the C-terminal region of the α-chain of IR and/or IGF-1R) may be produced using a screening method based on use of the atomic coordinates corresponding to the 3D structure of the C-terminal region of the α-chain of IR and/or IGF-1R in isolation or as it associates with IR and/or IGF-1R, or alternatively may be identified by screening against a specific target molecule which is indicative of the capacity to bind to the low affinity binding site of IR and/or IGF-1R.

The candidate compounds and/or compounds identified or designed using a method of the present invention may be any suitable compound, synthetic or naturally occurring, preferably synthetic. In one embodiment, a synthetic compound selected or designed by the methods of the invention preferably has a molecular weight equal to or less than about 5000, 4000, 3000, 2000, 1000 or 500 daltons. A compound of the present invention is preferably soluble under physiological conditions.

The compounds may encompass numerous chemical classes, though typically they are organic molecules, preferably small organic compounds having a molecular weight of more than 50 and less than about 2,500 daltons, preferably less than 1500, more preferably less than 1000 and yet more preferably less than 500. Such compounds can comprise functional groups necessary for structural interaction with proteins, particularly hydrogen bonding, and typically include at least an amine, carbonyl, hydroxyl or carboxyl group, preferably at least two of the functional chemical groups. The compound may comprise cyclical carbon or heterocyclic structures and/or aromatic or polyaromatic structures substituted with one or more of the above functional groups. Compounds can also comprise biomolecules including peptides, saccharides, fatty acids, steroids, purines, pyrimidines, derivatives, structural analogs, or combinations thereof.

Compounds may include, for example: (1) Peptides such as soluble peptides, including Ig-tailed fusion peptides and members of random peptide libraries (see, e.g., Lam et al., 1991; Houghten et al., 1991) and combinatorial chemistry-derived molecular libraries made of D- and/or L-configuration amino acids; (2) Phosphopeptides (e.g., members of random and partially degenerate, directed phosphopeptide libraries, see, e.g., Songyang et al., 1993); (3) Antibodies (e.g., polyclonal, monoclonal, humanized, anti-idiotypic, chimeric, and single chain antibodies as well as Fab, (Fab)$_2$, Fab expression library and epitope-binding fragments of antibodies); (4) Nonimmunoglobulin binding proteins such as but not restricted to avimers, DARPins and lipocalins; (5) Nucleic acid-based aptamers; and (6) Small organic and inorganic molecules.

Ligands can be obtained from a wide variety of sources including libraries of synthetic or natural compounds. Synthetic compound libraries are commercially available from, for example, Maybridge Chemical Co. (Tintagel, Cornwall; UK), AMRI (Budapest, Hungary) and ChemDiv (San Diego, Calif.), Specs (Delft, The Netherlands).

Natural compound libraries comprising bacterial, fungal, plant or animal extracts are available from, for example, Pan Laboratories (Bothell, Wash.), TimTec (Newark, Del.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al., 1993; Erb et al., 1994; Zuckermann et al., 1994; Cho et al., 1993; Carell et al., 1994a; Carell et al., 1994b; and Gallop et al., 1994). In addition, natural or synthetic compound libraries and compounds can be readily modified through conventional chemical, physical and biochemical means (see, e.g., Blondelle and Houghton, 1996), and may be used to produce combinatorial libraries. In another approach; previously identified pharmacological agents can be subjected to directed or random chemical modifications, such as acylation, alkylation, esterification, amidification, and the analogs can be screened for IR and/or IGF-1R-modulating activity.

Numerous methods for producing combinatorial libraries are known in the art, including those involving biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide or peptide libraries, while the other four approaches are applicable to polypeptide, peptide, nonpeptide oligomer, or small molecule libraries of compounds (Lam, 1997).

Compounds also include those that may be synthesized from leads generated by fragment-based drug design, wherein the binding of such chemical fragments is assessed by soaking or co-crystallizing such screen fragments into crystals provided by the invention and then subjecting these to an X-ray beam and obtaining diffraction data. Difference Fourier techniques are readily applied by those skilled in the art to determine the location within the IR ectodomain and/or IGF-1R ectodomain structure at which these fragments bind, and such fragments can then be assembled by synthetic chemistry into larger compounds with increased affinity for the receptor.

Isolated Peptides or Mimetics Thereof

Compounds identified or designed using the methods of the invention can be a peptide or a mimetic thereof. Furthermore, in one aspect the present invention provides an isolated peptide or mimetic thereof which binds the L1 domain of IR and/or the L1 domain of IGF-1R, the peptide comprising:

i) an amino acid sequence as provided in SEQ ID NO: 13 or SEQ ID NO: 15;
ii) an amino acid sequence which is at least 50% identical to SEQ ID NO: 13 and/or SEQ ID NO: 15; or
iii) a fragment of i) or ii) which binds the L1 domain of IR and/or the L1 domain of IGF-1R, wherein the peptide has a helical structure.

The isolated peptides or mimetics of the invention may be conformationally constrained molecules or alternatively molecules which are not conformationally constrained such as, for example, non-constrained peptide sequences. The term "conformationally constrained molecules" means conformationally constrained peptides and conformationally constrained peptide analogues and derivatives.

The term "analogues" refers to molecules having a chemically analogous structure to naturally occurring α-amino acids. Examples include molecules containing gem-diaminoalkyl groups or alklylmalonyl groups.

The term "derivatives" includes α-amino acids wherein one or more side groups found in the naturally occurring α-amino acids have been modified. Thus, for example the amino acids may be replaced with a variety of uncoded or modified amino acids such as the corresponding D-amino acid or N-methyl amino acid. Other modifications include substitution of hydroxyl, thiol, amino and carboxyl functional groups with chemically similar groups.

With regard to peptides and mimetics thereof, other examples of other unnatural amino acids or chemical amino acid analogues/derivatives which can be introduced as a substitution or addition include, but are not limited to, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

The mimetic may be a peptidomimetic. A "peptidomimetic" is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics for use in the methods of the invention, and/or of the invention, provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

There are sometimes advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are generally cheaper to produce than peptides.

Suitable peptidomimetics based on the C-terminal region of the α-chain of IR and/or IGR-1R can be developed using readily available techniques. Thus, for example, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics derived from peptides of the C-terminal region of the IR and/or IGF-1R α-chain can be aided by reference to the three dimensional structure of these residues as provided in Appendixes I to IV. This structural information can be used to search three-dimensional databases to identify molecules having a similar structure, using programs such as Sybyl/3DB Unity (Tripos Associates, St. Louis, Mo.).

Those skilled in the art will recognize that the design of a peptidomimetic may require slight structural alteration or adjustment of a chemical structure designed or identified using the methods of the invention. In general, chemical compounds identified or designed using the methods of the invention can be synthesized chemically and then tested for ability to modulate IR and/or IGF-1R activity using any of the methods described herein. The methods of the invention are particularly useful because they can be used to greatly decrease the number potential mimetics which must be screened for their ability to modulate IR and/or IGF-1R activity.

The peptides or peptidomimetics of the present invention can be used in assays for screening for candidate compounds which bind to regions of IR and/or IGF-1R and potentially interfere with the binding of insulin to IR and/or signal transduction and/or the binding of IGF to IGF-1R and/or signal transduction. Peptides or peptidomimetics which mimic target binding sites are particularly useful as specific target molecules for identifying potentially useful ligands for IR and/or IGF-1R.

Standard solid-phase ELISA assay formats are particularly useful for identifying compounds that bind to the receptor. In accordance with this embodiment, the peptide or peptidomimetic immobilized on a solid matrix, such as, for example an array of polymeric pins or a glass support. Conveniently, the immobilized peptide or peptidomimetic is a fusion polypeptide comprising Glutathione-S-transferase (GST; e.g. a CAP-ERK fusion), wherein the GST moiety facilitates immobilization of the protein to the solid phase support. This assay format can then be used to screen for candidate compounds that bind to the immobilised peptide or peptidomimetic and/or intereefere with binding of a natural binding partner of IR and/or IGF-1R to the immobilised peptide or peptidomimetic.

As used herein a "fragment" is a portion of a peptide of the invention which maintains a defined activity of the "full-length" peptide, namely the ability to bind to the low affinity binding site of IR and/or IGF-1R, or to bind to the L1 domain of IR and/or IGF-1R. Fragments can be any size as long as they maintain the defined activity. Preferably, the fragment maintains at least 50%, more preferably at least 75%, of the activity of the full length polypeptide.

The % identity of a peptide is determined by GAP (Needleman and Wunsch, 1970) analysis (GCG program) with a gap creation penalty=5, and a gap extension penalty=0.3. The query sequence is at least 10 amino acids in length, and the GAP analysis aligns the two sequences over a region of at least 10 amino acids. More preferably, the GAP analysis aligns two sequences over their entire length.

With regard to a defined peptide, it will be appreciated that % identity figures higher than those provided above will encompass preferred embodiments. Thus, where applicable, in light of the minimum % identity figures, it is preferred that the peptide comprises an amino acid sequence which is at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the peptides identified or designed using the methods of the invention, and/or of the present invention, can be prepared by introducing appropriate nucleotide changes into a nucleic acid of the present invention, or by in vitro synthesis of the desired peptide. Such mutants include, for example, deletions, insertions or substitutions of residues within the amino acid sequence. A combination of deletion, insertion and substitution can be made to arrive at the final construct, provided that the final peptide product possesses the desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Substitution mutants have at least one amino acid residue in the peptide removed and a different residue inserted in its place. Sites of interest are those in which particular residues obtained from various strains or species are identical. These sites, especially those falling within a sequence of at least three other identically conserved sites, are preferably substituted in a relatively conservative manner. Such conservative substitutions are shown in Table 1 under the heading of "exemplary substitutions".

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment a mutant/variant peptide has one or two or three or four conservative amino acid changes when compared to a peptide defined herein. Details of conservative amino acid changes are provided in Table 1.

Also included within the scope of the invention are peptides which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the peptide.

The residues that form the IR segment 693-710 can be grouped into three classes:—Class A: those whose side chains are completely buried in the interface with L1 (viz. F701 and F705); Class B: those whose side chains lie at the periphery of the interface with L1 (viz. K694, E697, E698, S700, R702, T704, Y708 and L709); and Class C: those whose side chains appear to have no interaction with L1 (viz. L693, E695, L696, S699, K703, E706, D707 and H710). In terms of using the 693-710 peptide itself as a scaffold for mimetics that might compete with the C-terminal region of the IR α-chain peptide in its binding to the L1 domain, design might focus in the first instance on substitution of those residues in belonging to Class B, given that the two residues lying in Class A are relatively optimally packed within the interface and already have few degrees of freedom. Higher affinity binding might be achieved by substitution of one or more of the Class B residues with either naturally-occurring amino acids or non-natural amino acids. For example, the substitution of one or more of the charged residues K694, E697, E698 and R702 with residues that have reduced rotameric degrees of freedom (i.e. reduced entropy) may lead to higher affinity binding or altered physicochemical properties of the compound. Such modification for example may include substitution by the naturally occurring amino acids Phe, Tyr or Trp. As a further example, in the case of K694 and R702, it may be possible to substitute these residues by more bulky non-natural amino acids that retain the terminal cationic character, for example substitution by the basic phenyl propanoic acid derivatives App (L-2-amino-3-(4-aminophenyl)propanoic acid) and/or Gpp, (L-2-amino-3-(4-guanidinophenyl)propanoic acid) (Svenson et al., 2009). A further strategy for design might involve substitutions to improve the overall stability of the helical structure (for example helix stapling—see Danial et al., 2008). Such substitutions would likely be made within Class C residues. A yet further strategy to improve affinity or physicochemical properties might involve truncation of the helical segment and/or attaching an N- or C-terminal group also designed to improve affinity. Similar principles of design may be applied to generate modified peptides based on the native IGF-1R peptide 681-697 as outlined above for the IR peptide.

In a particularly preferred embodiment, a peptide or mimetic thereof of the invention does not comprise any one of the following described in U.S. Pat. No. 7,173,005:

a) $X_1 X_2 X_3 X_4 X_5$ wherein $X_1$ $X_2$, $X_4$ and $X_5$ are aromatic amino acids, and $X_3$ is any polar amino acid;

b) $X_6 X_7 X_8 X_9 X_{10} X_{11} X_{12} X_{13}$ wherein $X_6$ and $X_7$ are aromatic amino acids, $X_8$, $X_9$, $X_{11}$ and $X_{12}$ are any amino acid, and $X_{10}$ and $X_{13}$ are hydrophobic amino acids;

c) $X_{14} X_{15} X_{16} X_{17} X_{18} X_{19} X_{20} X_{21}$ wherein $X_{14}$, and $X_{17}$ are hydrophobic amino acids, $X_{15}$, $X_{16}$, $X_{18}$ and $X_{19}$ are any amino acid, and $X_{20}$ and $X_{21}$, are aromatic amino acids;

d) $X_{22} X_{23} X_{24} X_{25} X_{26} X_{27} X_{28} X_{29} X_{30} X_{31} X_{32} X_{33} X_{34} X_{35} X_{36} X_{37} X_{38} X_{39} X_{40} X_{41}$ wherein $X_{22}$, $X_{25}$, $X_{28}$, $X_{29}$, $X_{30}$, $X_{33}$, $X_{34}$, $X_{35}$, $X_{36}$, $X_{37}$, $X_{38}$, $X_{40}$, and $X_{41}$ are any amino acid, $X_{35}$ and $X_{37}$ may be any amino acid for binding to IR, whereas $X_{35}$ is preferably a hydrophobic amino acid and $X_{37}$ is preferably glycine for binding to IGF-1R and possess agonist or antagonist activity. $X_{23}$ and $X_{26}$ are hydrophobic amino acids. This sequence further comprises at least two cysteine residues, preferably at $X_{25}$ and $X_{40}$ $X_{31}$ and $X_{32}$ are small amino acids;

e) $X_{42} X_{43} X_{44} X_{45} X_{46} X_{47} X_{48} X_{49} X_{50} X_{51} X_{52} X_{53} X_{54} X_{55} X_{56} X_{57} X_{58} X_{59} X_{60} X_{61}$ wherein $X_{42}$, $X_{43}$, $X_{44}$, $X_{45}$, $X_{53}$, $X_{55}$, $X_{56}$, $X_{58}$, $X_{60}$ and $X_{61}$ may be any amino acid, $X_{43}$, $X_{46}$, $X_{49}$, $X_{50}$, $X_{54}$ are hydrophobic amino acids, $X_{47}$ and $X_{59}$ are preferably cysteines, $X_{48}$ is a polar amino acid, and $X_{51}$, $X_{52}$ and $X_{57}$ are small amino acids;

f) $X_{62} X_{63} X_{64} X_{65} X_{66} X_{67} X_{68} X_{69} X_{70} X_{71} X_{72} X_{73} X_{74} X_{75} X_{76} X_{77} X_{78} X_{79} X_{80} X_{81}$ wherein $X_{62}$, $X_{65}$, $X_{68}$, $X_{69}$, $X_{71}$, $X_{73}$, $X_{76}$, $X_{77}$, $X_{78}$, $X_{80}$, and $X_{81}$ may be any amino acid; $X_{63}$, $X_{70}$, $X_{74}$ are hydrophobic amino acids; $X_{64}$ is a polar amino acid, $X_{67}$ and $X_{75}$ are aromatic amino acids and $X_{72}$ and $X_{79}$ are preferably cysteines capable of forming a loop;

g) H $X_{82} X_{83} X_{84} X_{85} X_{86} X_{87} X_{88} X_{89} X_{90} X_{91} X_{92}$ wherein $X_{82}$ is proline or alanine, $X_{83}$ is a small amino acid, $X_{84}$ is selected from leucine, serine or threonine, $X_{85}$ is a polar amino acid, $X_{86}$, $X_{88}$, $X_{89}$ and $X_{90}$ are any amino acid, and $X_{87}$, $X_{91}$ and $X_{92}$ are an aliphatic amino acid;

h) $X_{104} X_{105} X_{106} X_{107} X_{108} X_{109} X_{110} X_{111} X_{112} X_{113} X_{114}$ wherein at least one of the amino acids of $X_{106}$ through $X_{111}$, and preferably two, are tryptophan separated by three amino acids, and wherein at least one of $X_{104}$, $X_{105}$ and $X_{106}$ and at least one of $X_{112}$, $X_{113}$ and $X_{114}$ are cysteine;

i) an amino acid sequence comprising the sequence JBA5: DYKDLCQSWGVRIGWLAGLCPKK or JBA5 minus FLAG® tag and terminal lysines: LCQSWGVRIGWLA-GLCP (Formula 9); and j) W $X_{123}$ G Y $X_{124}$ W $X_{125} X_{126}$ wherein $X_{123}$ is selected from proline, glycine, serine, arginine, alanine or leucine, but more preferably proline; $X_{124}$ is any amino acid, but preferably a charged or aromatic amino acid; $X_{125}$ is a hydrophobic amino acid preferably leucine or phenylalanine, and most preferably leucine. $X_{126}$ is any amino acid, but preferably a small amino acid.

In a further preferred embodiment, a peptide or mimetic thereof of the invention is more structurally similar to the native C-terminal region of the α-chain of IR and/or the C-terminal region of the α-chain of IGF-1R than it is to any one of a) to j) above (such as the peptides provided as SEQ ID Nos: 16 to 18).

The design of synthetic non-peptide mimetics of α-helices is an established art (see for example Davis et al., 2006). In particular, methods of mimicry of i, i+4, i+7 motifs (such as those identified within the C-terminal helical region of the α-chain of IR and IGF-1R and which interact the respective L1 domains (i.e. IR residues Phe701, Phe705, Tyr708 and IGF-1R residues Tyr688, Phe 692, Phe 695) are known. For example, these motifs may be mimicked by terphenyl, oligophenyl, chalcone or 1,4-benzodiazepine-2,5-dione scaffolds (Davis et al., 2006) or by benzoylurea scaffolds (US 2008153802). Non-peptide mimetics of α-helices have been investigated as therapeutics in a number of disease contexts, for example HIV1 infection (disruption of the assembly of the hexameric helical bundle (Ernst et al., 2001)) and cancer (disruption of the assembly of the HDM2-p53 complex (Yin et al., 2005); inhibitors of Bcl-2 family heterodimerisation (Degterev et al., 2001).

With regard to redesigning compounds using a method of the invention, in an embodiment the compound is redesigned to be more structurally similar to the native C-terminal region of the α-chain of IR and/or the C-terminal region of the α-chain of IGF-1R. Examples of peptides which could be redesigned in this manner include, but are not limited to, those described by Schäffer et al. (2003) and/or U.S. Pat. No. 7,173,005 (see above).

Interaction of Compounds with IR and/or IGF-1R

A compound may interact with the low affinity binding site of IR and/or IGF-1R by binding either directly or indirectly to that region. A compound which binds directly, binds to the specified region. A compound which binds indirectly, binds to a region in close proximity to or adjacent to the low affinity binding site of IR and/or IGF-1R with the result that it interferes with the ability of IR to bind to insulin, or IGF-1R to bind IGF, either antagonistically or agonistically. Such interference may be steric, electrostatic, or allosteric. Preferably, a compound interacts with the low affinity binding site of IR and/or IGF-1R by binding directly to the specified region. In the case of compounds that bind to specific target molecules, such compounds bind directly to the specific target molecule.

A compound may alternatively interact with the L1 domain of IR and/or IGF-1R in a manner similar to that of the C-terminal region of the α-chain of IR and/or IGF-1R by binding either directly or indirectly to that region. A compound which binds directly, binds to the specified region. A compound which binds indirectly, binds to a region in close proximity to or adjacent to the L1 domain of IR and/or IGF-1R in a manner similar to that of the C-terminal region of the α-chain of IR and/or IGF-1R with the result that it interferes with the ability of IR to bind to insulin, or IGF-1R to bind IGF, either antagonistically or agonistically. Such interference may be steric, electrostatic, or allosteric. Preferably, a compound interacts with the L1 domain of IR and/or IGF-1R in a manner similar to that of the C-terminal region of the α-chain of IR and/or IGF-1R by binding directly to the specified region. In the case of compounds that bind to specific target molecules, such compounds bind directly to the specific target molecule.

Binding can be either by covalent or non-covalent interactions, or both. Examples of non-covalent interactions include electrostatic interactions, van der Waals interactions, hydrophobic interactions and hydrophilic interactions.

When a compound of the invention interacts with IR and/or IGF-1R, it preferably "modulates" IR or IGF-IR, respectively. By "modulate" we mean that the compound changes an activity of IR or IGF-1R by at least 10%. Suitably, a compound modulates IR or IGF-1R by increasing or decreasing signal transduction via IR or IGF-1R, respectively. The phrase "decreases signal transduction" is intended to encompass partial or complete inhibition of signal transduction via IR or IGF-1R. The ability of a candidate compound to increase or decrease signal transduction via IR or IGF-1R can be assessed by any one of the IR or IGF-1R cell-based assays described herein.

Compounds may act as antagonists or agonists for insulin binding to IR or as antagonists or agonists for IGF binding to IGF-1R.

Compounds of the present invention preferably have an affinity for IR or IGF-1R sufficient to provide adequate binding for the intended purpose. Suitably, such compounds and compounds which bind to specific target molecules of IR or IGF-1R have an affinity ($K_d$) of from $10^{-5}$ to $10^{-15}$ M. For use as a therapeutic, the compound suitably has an affinity ($K_d$) of from $10^{-7}$ to $10^{-15}$ M, preferably from $10^{-8}$ to $10^{-12}$ M and more preferably from $10^{-10}$ to $10^{-12}$ M. Where a compound is to be used as a reagent in a competitive assay to identify other ligands, the compound suitably has an affinity ($K_d$) of from $10^{-5}$ to $10^{-12}$ M.

As will be evident to the skilled person, the crystal structures presented herein have enabled, for the first time, direct comparison of the regions controlling insulin or IGF binding in the closely related IR and IGF-1R. The structures have enabled the identification of the C-terminal region of the α-chain of IR and IGF-1R, critical for the initial binding of insulin or IGF, respectively, and in the subsequent formation of the high affinity insulin-IR or IGF-IGF-1R complex that leads to signal transduction.

In one preferred embodiment, a compound has a high specificity for IR and/or a specific target molecule of IR but not for IGF-1R, i.e. a compound selectively binds to IR or has enhanced selectivity for IR over IGF-1R. In this respect, a compound suitably has an affinity ($K_d$) for IR and/or a specific target molecule of IR of no more than $10^{-5}$ M, preferably no more than $10^{-7}$ M, and an affinity for IGF-1R of at least $10^{-5}$ M, preferably at least $10^{-3}$ M. Such compounds are desirable as, for example, IR agonists where the propensity to interact with IGF-1R and thus, for example, promote undesirable cell proliferation, is reduced.

In a preferred embodiment, the (IR or specific target molecule of IR)/IGF-1R binding affinity ratio for a compound is at least 10 and preferably at least 100.

In another preferred embodiment, a compound has a high specificity for IGF-1R and/or a specific target molecule of IGF-1R but not for IR, i.e. a compound selectively binds to IGF-1R or has enhanced selectivity for IGF-1R over IR. In this respect, a compound suitably has an affinity ($K_d$) for IGF-1R and/or a specific target molecule of IGF-1R of no more than $10^{-5}$ M, preferably no more than $10^{-7}$ M, and an affinity for IR of at least $10^{-5}$ M, preferably at least $10^{-3}$ M. Such compounds are desirable as, for example, IGF-1R agonists where there propensity to interact with IR and thus, for example, promote glucose uptake and metabolism, is reduced.

In a preferred embodiment, the (IGF-1R or specific target molecule of IGF-IR)/(IR) binding affinity ratio for a compound is at least 10 and preferably at least 100.

Screening Assays and Confirmation of Binding

Compounds of the invention may be subjected to further confirmation of binding to IR and/or IGF-1R by cocrystallization of the compound with IR and/or IGF-1R and structural determination, as described herein.

Compounds designed or selected according to the methods of the present invention are preferably assessed by a number of in vitro and in vivo assays of IR and/or IGF-1R function to confirm their ability to interact with and modulate IR and/or IGF-1R activity. For example, compounds may be tested for their ability to bind to IR and/or IGF-1R and/or for their ability to modulate e.g. disrupt, IR and/or IGF-1R signal transduction.

Libraries may be screened in solution by methods generally known in the art for determining whether ligands competitively bind at a common binding site. Such methods may include screening libraries in solution (e.g., Houghten, 1992), or on beads (Lam, 1991), chips (Fodor, 1993), bacteria or spores (U.S. Pat. No. 5,223,409), plasmids (Cull et al., 1992), or on phage (Scott & Smith, 1990; Devlin, 1990; Cwirla et al., 1990; Felici, 1991; U.S. Pat. No. 5,223,409).

Where the screening assay is a binding assay, IR or IGF-1R may be joined to a label, where the label can directly or indirectly provide a detectable signal. Various labels include radioisotopes, fluorescent molecules, chemiluminescent molecules, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc., which are used to facilitate optimal protein-protein binding and/or reduce non-specific or background interactions. Reagents that improve the efficiency of the assay, such as protease inhibitors, nuclease inhibitors, antimicrobial agents, etc., may be used. The components are added in any order that produces the requisite binding. Incubations are performed at any temperature that facilitates optimal activity, typically between 4 and 40° C.

Direct binding of compounds to IR or IGF-1R can also be done by Surface Plasmon Resonance (BIAcore) (reviewed in Morton & Myszka, 1998). Here the receptor is immobilized on a CM5 or other sensor chip by either direct chemical coupling using amine or thiol-disulphide exchange coupling (Nice & Catimel, 1999) or by capturing the receptor ectodomain as an Fc fusion protein to an appropriately derivatised sensor surface (Morten & Myszka, 1998). The potential binding molecule (called an analyte) is passed over the sensor surface at an appropriate flow rate and a range of concentrations. The classical method of analysis is to collect responses for a wide range of analyte concentrations. A range of concentrations provides sufficient information about the reaction, and by using a fitting algorithm such as CLAMP (see Morton & Myszka, 1998), rate constants can be determined (Morton & Myszka, 1998; Nice & Catimel, 1999). Normally, the ligand surface is regenerated at the end of each analyte binding cycle. Surface regeneration ensures that the same number of ligand binding sites is accessible to the analyte at the beginning of each cycle.

Incubation periods are selected for optimum activity, but may also be optimized to facilitate rapid high-throughput screening. Normally, between 0.1 and 1 hour will be sufficient. In general, a plurality of assay mixtures is run in parallel with different test agent concentrations to obtain a differential response to these concentrations. Typically, one of these concentrations serves as a negative control, i.e. at zero concentration or below the level of detection.

The basic format of an in vitro competitive receptor binding assay as the basis of a heterogeneous screen for small organic molecular replacements for insulin may be as follows: occupation of the low affinity binding site of IR and/or IGF-1R is quantified by time-resolved fluorometric detection (TRFD) as described by Denley et al., 2004. R$^-$IR-A, R$^-$IR-B and P6 cells are used as sources of IR-A, IR-B and IGF-1R respectively. Cells are lysed with lysis buffer (20 mM HEPES, 150 mM NaCl, 1.5 mM MgCl$_2$, 10% (v/v) glycerol, 1% (v/v) Triton X-100, 1 mM EGTA pH 7.5) for 1 hour at 4° C. Lysates are centrifuged for 10 minutes at 3500 rpm and then 100 µl is added per well to a white Greiner Lumitrac 600 plate previously coated with anti-insulin receptor antibody 83-7 or anti-IGF-1R antibody 24-31. Neither capture antibody interferes with receptor binding by insulin, IGF-I or IGF-II. Approximately 100,000 fluorescent counts of europium-labelled insulin or europium-labelled IGF-I are added to each well along with various amounts of unlabelled competitor and incubated for 16 hours at 4° C. Wells are washed with 20 mM Tris, 150 mM NaCl, 0.05% (v/v) Tween 20 (TBST) and DELFIA enhancement solution (100 µl/well) is added. Time-resolved fluorescence is measured using 340 nm excitation and 612 nm emission filters with a BMG Lab Technologies Polarstar™ Fluorimeter or a Wallac Victor II (EG & G Wallac, Inc.).

Examples of other suitable assays which may be employed to assess the binding and biological activity of compounds to and on IR are well known in the art. For example, suitable assays may be found in PCT International Publication Number WO 03/027246. Examples of suitable assays include the following:

(i) Receptor autophosphorylation (as described by Denley et al., 2004). R$^-$IR-A, R$^-$IR-B cells or P6 cells are plated in a Falcon 96 well flat bottom plate at $2.5 \times 10^4$ cells/well and grown overnight at 37° C., 5% CO$_2$. Cells are washed for 4 hours in serum-free medium before treating with one of either insulin, IGF-I or IGF-II in 100 µl DMEM with 1% BSA for 10 minutes at 37° C., 5% CO$_2$. Lysis buffer containing 2 mM Na$_3$VO$_4$ and 1 mg/ml NaF is added to cells and receptors from lysates are captured on 96 well plates precoated with antibody 83-7 or 24-31 and blocked with 1×TBST/0.5% BSA. After overnight incubation at 4° C., the plates are washed with 1×TBST. Phosphorylated receptor is detected with europium-labelled antiphosphotyrosine antibody PY20 (130 ng/well, room temperature, 2 hours). DELFIA enhancement solution (100 µl/well) is added and time resolved fluorescence detected as described above.

(ii) Glucose uptake using 2-deoxy-[U-14C] glucose (as described by Olefsky, 1978). Adipocytes between days 8-12 post-differentiation in 24-well plates are washed twice in Krebs-Ringer Bicarbonate Buffer (25 mM Hepes, pH 7.4 containing 130 mM NaCl, 5 mM KCl, KH$_2$PO$_4$, 1.3 mM MgSO$_4$.7H$_2$O, 25 mM NaHCO$_3$ and 1.15 mM CaCl$_2$) supplemented with 1% (w/v) RIA-grade BSA and 2 mM sodium pyruvate. Adipocytes are equilibrated for 90 min at 37° C. prior to insulin addition, or for 30 min prior to agonist or antagonist addition. Insulin (Actrapid, Novogen) is added over a concentration range of 0.7 to 70 nM for 30 min at 37° C. Agonist or antagonist (0 to 500 µM) is added to adipocytes for 90 min followed by the addition of insulin in the case of antagonists. Uptake of 50 µM 2-deoxy glucose and 0.5 µCi 2-deoxy-[U-$^{14}$C] glucose (NEN, PerkinElmer Life Sciences) per well is measured over the final 10 min of agonist stimulation by scintillation counting.

(iii) Glucose transporter GLUT4 translocation using plasma membrane lawns (as described by Robinson & James (1992) and Marsh et al. (1995)).

(iv) GLUT4 translocation using plasma membrane lawns (as described by Marsh et al., 1995). 3T3-L1 fibroblasts are grown on glass coverslips in 6-well plates and differentiated into adipocytes. After 8-12 days post-differentiation, adipocytes are serum-starved for 18 hrs in DMEM containing 0.5% FBS. Cells are washed twice in Krebs-Ringer Bicarbonate Buffer, pH 7.4 and equilibrated for 90 min at 37° C. prior to insulin (100 nM) addition, or for 30 min prior to compound (100 μM) addition. After treatments, adipocytes are washed in 0.5 mg/ml poly-L-lysine in PBS, shocked hypotonically by three washes in 1:3 (v/v) membrane buffer (30 mM Hepes, pH 7.2 containing 70 mM KCl, 5 mM $MgCl_2$, 3 mM EGTA and freshly added 1 mM DTT and 2 mM PMSF) on ice. The washed cells are then sonicated using a probe sonicator (Microson) at setting 0 in 1:1 (v/v) membrane buffer on ice, to generate a lawn of plasma membrane fragments that remain attached to the coverslip. The fragments are fixed in 2% (w/v) paraformaldehyde in membrane buffer for 20 min at 22° C. and the fixative quenched by 100 mM glycine in PBS. The plasma membrane fragments are then blocked in 1% (w/v) Blotto in membrane buffer for 60 min at 22° C. and immunolabelled with an in-house rabbit affinity purified anti-GLUT4 polyclonal antibody (clone R10, generated against a peptide encompassing the C-terminal 19 amino acids of GLUT4) and Alexa 488 goat anti-rabbit secondary antibody (Molecular Probes; 1:200). Coverslips are mounted onto slides using FluoroSave reagent (Calbiochem), and imaged using an OptiScan confocal laser scanning immunofluorescence microscope (Optiscan, VIC., Australia). Data are analysed using ImageJ (NIH) imaging software. At least six fields are examined within each experiment for each condition, and the confocal microscope gain settings over the period of experiments are maintained to minimise between-experiment variability.

Insulin agonist activity may be determined using an adipocyte assay. Insulin increases uptake of $^3H$ glucose into adipocytes and its conversion into lipid. Incorporation of $^3H$ into a lipid phase is determined by partitioning of lipid phase into a scintillant mixture, which excludes water-soluble $^3H$ products. The effect of compounds on the incorporation of $^3H$ glucose at a sub-maximal insulin dose is determined, and the results expressed as increase relative to full insulin response. The method is adapted from Moody et al., (1974). Mouse epididymal fat pads are dissected out, minced into digestion buffer (Krebs-Ringer 25 mM HEPES, 4% HSA, 1.1 mM glucose, 0.4 mg/ml Collagenase Type 1, pH 7.4), and digested for up to 1.5 hours at 36.5 C. After filtration, washing (Krebs-Ringer HEPES, 1% HSA) and resuspension in assay buffer (Krebs-Ringer HEPES, 1% HSA), free fat cells are pipetted into 96-well Picoplates containing test solution and approximately an $ED_{20}$ insulin.

The assay is started by addition of $^3H$ glucose (e.g. ex. Amersham TRK 239), in a final concentration of 0.45 mM glucose. The assay is incubated for 2 hours at 36.5° C., in a Labshaker incubation tower, 400 rpm, then terminated by the addition of Permablend/Toluene scintillant (or equivalent), and the plates sealed before standing for at least 1 hour and detection in a Packard Top Counter or equivalent. A full insulin standard curve (8 dose) is run as control on each plate.

Data are presented graphically, as the effect of the compound on an (approximate). $ED_{20}$ insulin response, with data normalized to a full insulin response. The assay can also be run at basal or maximal insulin concentration.

To test the in vivo activity of a compound, an intravenous blood glucose test may be carried out on Wistar rats as follows. Male Mol: Wistar rats, weighing about 300 g, are divided into two groups. A 10 μl sample of blood is taken from the tail vein for determination of blood glucose concentration. The rats are then anaesthetized (e.g. with Hypnorm/Dormicum) at t=30 min and blood glucose measured again at t=−20 min and at t=0 min. After the t=0 sample is taken, the rats are injected into the tail vein with vehicle or test substance in an isotonic aqueous buffer at a concentration corresponding to a 1 ml/kg volume of injection. Blood glucose is measured at times 10, 20, 30, 40, 60, 80, 120 and 180 min. The anaesthetic administration is repeated at 20 min intervals.

Additional assays to determine the effect of binding molecules on IGF-1R activity are as follows:

(i) Cell Viability Assay on HT29 cells with induction of Apoptosis: The ability of compounds to inhibit IGF-mediated rescue from apoptosis is measured using the colorectal cell line HT29 cells (ATCC: HTB 38) after induction with Na Butyrate. The HT29 cells are plated out onto white Fluoronunc 96 well plates (Nunc) at 12,000 cells/ml and incubated at 37° C., 5% $CO_2$ for 48 hours. Media is aspirated and 100 μl/well of serum free DMEM/F12 is added for 2 hours to serum starve cells. IGF (100 μl/well 0.05-50 nM dilutions) in the presence and the absence of inhibitory compound is added in 0.1% BSA solution (Sigma) in DMEM/F12 (Gibco) in triplicate. A final concentration of 5 mM Butyrate (Sigma) is added to each well. Plates are incubated at 37° C., 5% $CO_2$ for a further 48 hours. Plates are brought to room temperature and developed (as per instructions for CTG Assay (Promega)). Luminescence signal is measured on the Polarstar plate reader and data is evaluated using table curve to obtain the specific ED50.

(ii) Cell Migration Assay: The migration assays are performed in the modified 96-well Boyden chamber (Neuroprobe, Bethesda, Mass.). An 8 μM polycarbonate filter, which is pre-soaked in 25 μg/ml of collagen in 10 mM acetic acid overnight at 4° C., is placed so as to divide the chamber into an upper & lower compartment. Varying concentrations of the IGF-I analogues (25 μl of 0-100 nM) diluted in RPMI (Gibco) with 0.5% BSA (Sigma) tested for their migration inducing ability, are placed in the lower compartment in quadruplicates. The wells of the upper chamber are seeded with 50 μl/well of $2 \times 10^5$ SW480 (ATCC:CCL 228) pre-incubated for 30 mins/37° C. with 1.1 μl of 2 μM Calcein (Molecular Probes). Cells migrate for 8 hours at 37° C., 5% $CO_2$. Unmigrated cells are removed by wiping the filter. The filter is then analysed in the Polarstar for fluorescence at excitation wavelength of 485 nm and emission wavelength of 520 nm. Data is evaluated using table curve to obtain the specific ED50 value.

(iii) Mouse Xenograft studies for anti-IGF-1R antibodies: In vivo studies are performed in 56-week-old female athymic BALBc nude mice, homozygous for the nunu allele. Mice are maintained in autoclaved micro-isolator cages housed in a positive pressure containment rack (Thoren Caging Systems Inc., Hazelton, Pa., USA. To establish xenografts, mice are injected subcutaneously into the left inguinal mammary line with $3 \times 10^6$ or $5 \times 10^6$ cells in 100 μl of PBS. Tumour volume (TV) is calculated by the formula (length× $width^2$)/2 (Clarke et al., 2000), where length is the longest axis and width the measurement at right angles to length.

Initial biodistribution of potential binding molecules are ascertained by injecting 40 BALBc nude mice with established xenografts with radiolabelled $^{111}$In- or $^{125}$I-anti-IGFR antibody (3 μg, 10 μCi) intravenously via the tail vein (total volume=0.1 ml). At designated time points after injection of the radioconjugates (t=4 h, days 1, 2, 3, 5 and 7), groups of mice (n=35) are killed by Ethrane anaesthesia. Mice are then exsanguinated by cardiac puncture, and tumours and organs (liver, spleen, kidney, muscle, skin, bone (femur), lungs, heart, stomach, brain, small bowel, tail and colon) are resected immediately. All samples are counted in a dual gamma scintillation counter (Packard Instruments). Triplicate standards prepared from the injected material are counted at each time point with tissue and tumour samples enabling calculations to be corrected for the physical decay of the isotopes. The tissue distribution data are calculated as the mean±s.d. percent injected dose per gram tissue (% ID $g^{-1}$) for the candidate molecule per time point.

Pharmacokinetics for the candidate compounds are ascertained as follows: Serum obtained from mice bearing xenografts, following infusion of radiolabelled-binding molecule as described above, is aliquoted in duplicate and counted in a gamma scintillation counter (Packard Instruments, Melbourne, Australia). Triplicate standards prepared from the injected material are counted at each time point with serum samples to enable calculations to be corrected for the isotope physical decay. The results of the serum are expressed as % injected dose per litre (% ID $l^{-1}$). Pharmacokinetic calculations are performed of serum data using a curve fitting program (WinNonlin, Pharsight Co., Mountain View, Calif., USA). A two-compartment model is used to calculate serum pharmacokinetic parameters of AUC (area under the serum concentration curve extrapolated to infinite time), CL (total serum clearance), $T_{1/2\alpha}$ and $T_{1/2\beta}$ (half-lives of the initial and terminal phases of disposition) for $^{125}$I- and $^{111}$In-labelled molecule.

(iv) Therapeutic in vivo studies: Tumour cells ($3\times10^6$) in 100 μl of media are inoculated subcutaneously into both flanks of 46-week-old female nude mice (n=5 $group^{-1}$). Candidate molecule treatment commences day 7 post-tumour cell inoculations (meant s.e. tumour volume=$60\times15$ $mm^3$) and consists of six intraperitoneal injections over 2 weeks of appropriate amounts of the candidate molecule or vehicle control. Tumour volume in $mm^3$ is determined as described previously. Data is expressed as mean tumour volume for each treatment group. Differences in tumour size between control and test groups are tested for statistical significance (p<0.05) by t-test.

Uses of Compounds

Compounds/chemical entities designed or selected by the methods of the invention described above may be used to modulate IR and/or IGF-1R activity in cells, i.e. activate or inhibit IR and/or IGF-1R activity. Such compounds may interact with the low affinity binding sites of IR and/or IGF-1R as defined herein, or mimic the C-terminal region of the α-chain of IR and/or IGF-1R as defined herein. They may also be used to modulate homodimerisation of IR and/or IGF-1R.

Modulation of homodimerisation of IR and/or IGF-1R may be achieved by direct binding of the chemical entity to a homodimerisation surface of IR and/or IGF-1R, and/or by an allosteric interaction elsewhere in the IR and/or IGF-1R extracellular domain.

Given that aberrant IR and/or IGF-1R activity is implicated in a range of disorders, the compounds described above may also be used to treat, ameliorate or prevent disorders characterised by abnormal IR and/or IGF-1R signalling. Examples of such disorders include malignant conditions including tumours of the brain, head and neck, prostate, ovary, breast, cervix, lung, pancreas and colon; and melanoma, rhabdomyosarcoma, mesothelioma, squamous carcinomas of the skin and glioblastoma.

The compounds designed to interact or identified as interacting with the extracellular domain of IR and/or IGF-1R, and in particular to interact with the target binding sites, are useful as agonists or antagonists against the action of insulin on IR and/or IGF on IGF-1R. The compounds are useful as assay reagents for identifying other useful ligands by, for example, competition assays, as research tools for further analysis of IR and/or IGF-1R and as potential therapeutics in pharmaceutical compositions.

Compounds provided by this invention are also useful as lead compounds for identifying other more potent or selective compounds. The mimetic compounds of the present invention are also potentially useful as inhibitors of the action of insulin and in the design of assay kits directed at identifying compounds capable of binding to the low affinity binding site for insulin on IR. The mimetic compounds of the present invention are also potentially useful as inhibitors of the action of IGF and in the design of assay kits directed at identifying compounds capable of binding to the low affinity binding site for IGF on IGF-1R. In particular, it is envisaged that compounds of the present invention will prove particularly useful in selecting/designing ligands which are specific for IR or IGF-1R.

In one embodiment, one or more of the compounds can be provided as components in a kit for identifying other ligands (e.g., small, organic molecules) that bind to IR or IGF-1R. Such kits may also comprise IR or IGF-1R, or functional fragments thereof. The compound and receptor components of the kit may be labeled (e.g. by radioisotopes, fluorescent molecules, chemiluminescent molecules, enzymes or other labels), or may be unlabeled and labelling reagents may be provided. The kits may, also contain peripheral reagents such as buffers, stabilizers, etc. Instructions for use can also be provided.

IR and IGF-1R agonists and antagonists, and in particular antagonists, provided by this invention are potentially useful as therapeutics. For example, compounds are potentially useful as treatments for cancers, including, but not limited to, breast, prostate, colorectal, and ovarian cancers. Human and breast cancers are responsible for over 40,000 deaths per year, as present treatments such as surgery, chemotherapy, radiation therapy, and immunotherapy show limited success. Recent reports have shown that a previously identified IGF-1R antagonist can suppress retinal neovascularization, which causes diabetic retinopathy (Smith et al., 1999). IGF-1R agonist compounds (i.e. existing IGF-1R compounds which have been modified employing methods of the present invention) are useful for development as treatments for neurological disorders, including stroke and diabetic neuropathy. Reports of several different groups implicate IGF-1R in the reduction of global brain ischemia, and support the use of IGF-I for the treatment of diabetic neuropathy (reviewed in Auer et al., 1998; Apfel, 1999). A number of therapeutics directed against IGF-1R are currently undergoing clinical trial as anti-cancer agents (Hewish et al., 2009)

The IGF-1R agonist peptides of the invention may be useful for enhancing the survival of cells and/or blocking apoptosis in cells.

Administration

Compounds of the invention, i.e. ligands of the invention or modulators of IR and/or IGF-1R identified or identifiable by the screening methods of the invention, may preferably be combined with various components to produce compositions of the invention. Preferably the compositions are combined with a pharmaceutically acceptable carrier or diluent to produce a pharmaceutical composition (which may be for human or animal use).

The formulation will depend upon the nature of the compound and the route of administration but typically they can be formulated for topical, parenteral, intramuscular, oral, intravenous, intra-peritoneal; intranasal inhalation, lung inhalation, intradermal or intra-articular administration. The compound may be used in an injectable form. It may therefore be mixed with any vehicle which is pharmaceutically acceptable for an injectable formulation, preferably for a direct injection at the site to be treated, although it may be administered systemically.

The pharmaceutically acceptable carrier or diluent may be, for example, sterile isotonic saline solutions, or other isotonic solutions such as phosphate-buffered saline. The compounds of the present invention may be admixed with any suitable binder(s), lubricant(s), suspending agent(s), coating agent(s), solubilising agent(s). It is also preferred to formulate the compound in an orally active form.

In general, a therapeutically effective daily oral or intravenous dose of the compounds of the invention, including compounds of the invention and their salts, is likely to range from 0.01 to 50 mg/kg body weight of the subject to be treated, preferably 0.1 to 20 mg/kg. The compounds of the invention and their salts may also be administered by intravenous infusion, at a dose which is likely to range from 0.001-10 mg/kg/hr.

Tablets or capsules of the compounds may be administered singly or two or more at a time, as appropriate. It is also possible to administer the compounds in sustained release formulations.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

The compositions (as well as the compounds alone) can also be injected parenterally, for example intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient.

The routes of administration and dosages described are intended only as a guide since a skilled practitioner will be able to determine readily the optimum route of administration and dosage for any particular patient depending on, for example, the age, weight and condition of the patient.

EXAMPLES

Example 1

A Thermodynamic Study of Ligand Binding to the First Three Domains of the Human Insulin Receptor (IR): Relationship Between the IR α-Chain C-Terminal Peptide (αCT) and the Site 1 Insulin Mimetic Peptides 1.1 Introduction In order to study ligand binding to the first three domains of IR ectodomain, isothermal titration calorimetry (ITC) was used. ITC allowed a direct assay of the interactions between the IR ectodomain classical αCT peptide (residues 704-719; SEQ ID NO: 11) and IR485 (a construct consisting of the first three N-terminal domains of the IR; SEQ ID NO: 10), as well as the interaction between the analogous peptide of human IGF-1R and IR485. At the same time the thermodynamics of binding of the N- and C-terminal segments of the insulin mimetic peptide S519 (Schäffer et al., 2003) to IR485, as well as the binding of S519 itself to IR485 were examined. S519 (SLEEEWAQVECEVYGRGCPSGSLDESFY-DWFERQLG; SEQ ID NO: 16) is a 36-residue peptide resulting from the affinity-optimization of two covalently-linked peptides, S371, a so-called "Site 1" peptide, and S446, a so-called "Site 2" peptide (Pillutla et al., 2002). S519 binds human IR with $K_d=2.0\times10^{-11}$ (Schäffer et al., 2003). Taken together, the results revealed a remarkable relationship between the IR αCT peptide and the Site 1 mimetic peptide, and suggested a previously undetected structural similarity between the mimetic peptides and insulin itself (Ward and Lawrence, 2009). Finally, the binding to IR485 of the IR αCT peptide carrying a F714A mutation (residues 704-719, TFEDYLHNVVAVPRPS; SEQ ID NO: 12) was examined.

1.2 Materials and Methods for Thermodynamic Experiments

Reagents

The IR485 construct of human IR was expressed in Lec8 mutant CHO cells and purified by gel filtration chromatography as described previously (Lou et al., 2006). IR485 consists of the first 485 residues of the mature human insulin receptor followed by the 16-residue sequence SDDDDKEQKLI-SEEDLN (SEQ ID NO: 10), which comprises a serine residue followed by an enterokinase cleavage site and a c-myc epitope tag. The c-myc tag was not removed for the ITC studies described here. IR485 was concentrated to 30 mg/ml in Tris-buffered saline (TBSA; 24.8 mM Tris-HCl (pH 8.0), 137 mM NaCl, 2.7 mM KCl and 0.02% sodium azide) using an Ultrafree centrifugal concentrator (Millipore, USA). Porcine insulin (Sigma-Aldrich, USA) was prepared in a zinc-free-form (termed ZFP-insulin) by extensive dialysis against 0.1% (v/v) acetic acid followed by lyophilization. Human IGF-I was obtained from Novozymes GroPep (Australia) as "receptor grade" material.

The IR classical αCT peptide (residues 704-719, TFEDYLHNVVFVPRPS; SEQ ID NO: 11), the IGF-1R classical αCT peptide (residues 691-706, VFEN-FLHNSIFVPRPE; SEQ ID NO: 14) as well as the F714A mutant of IR αCT (denoted IR αCT.714A; SEQ ID NO: 12) were obtained from Genscript Corporation (USA) at the >98% level of purity. The S519N20 peptide (SLEEE-WAQVECEVYGRGCPS; SEQ ID NO: 17) and the S519C16 peptide (GSLDESFYDWFERQLG; SEQ ID NO: 18) were obtained from AusPep (Australia) at the >90% level of purity.

The S519 peptide (SLEEEWAQVECEVYGRGCPSGSL DESFYDWFERQLG; SEQ ID NO: 16) was obtained from Activotec (UK) at the >85% purity. Peptides were prepared by dissolving in 10 mM HCl at ~4 mg/ml concentration and then diluting with TBSA. Oxidation of peptides S519N20 and S519 (which contain two cysteine residues) was carried out by incubating the respective peptide (prepared at 1 mg/ml in 50 mM ammonium bicarbonate adjusted to pH 8.5 with ammonia solution) in the dark at room temperature for 2 days and then lyophilizing before use. Oxidation was complete as determined by analysis with Ellman's reagent (5,5'-dithiobis-2-nitrobenzoate). All protein concentrations were determined by absorbance measurement at 280 nm using a NanoDrop 1000 spectrophotometer (Thermo Scientific, USA).

Isothermal Titration Calorimetry

ITC experiments were performed using a VP-ITC isothermal titration calorimeter (MicroCal Inc., USA) with the calorimeter cell held at 25° C. All samples were degassed prior to injection or placement into the cell, and the instrument was temperature equilibrated prior to the start of the injections. In all experiments the volume of sample placed in the cell was 1.4 ml and the titrant was injected in 7 μl volumes over 14 s at 3 min intervals, with the total number of injections being 40. The sample contents were stirred at a speed of 310 rpm over the duration of the titration. All titrants (i.e. ZFP-insulin, IGF-I, IR αCT peptide, IGF-1R αCT peptide, IR αCT.714A peptide, S519, S519N20, and S519C20) were first injected into a solution of TBSA alone in order ascertain the heat of dilution, which was then subtracted from the data of interest as appropriate. Data were analyzed using the instrument's software incorporated within the Origin 7 software (Origin-Lab, USA) and in all cases fitted as a single-site interaction using the methodologies outlined in the instrument's manual. All measurements showing quantifiable interaction were done in triplicate (in some cases at varying concentrations) and the resultant ITC-derived thermodynamic parameters averaged.

Dynamic Light Scattering (DLS)

DLS measurements were carried out using a Zetasizer NanoZS (Malvern Instruments Ltd, England). Samples of IR485 and IR485 in combination with IR αCT and/or ZFP-insulin at various concentrations were prepared in TBSA and equilibrated overnight at 4° C. Samples were spun at 13,000 g using a benchtop centrifuge to pellet any macroscopic particulates and then pipetted into a 45 μl glass cuvette held at 20° C. Data were analysed using the instrument's Dispersion Technology Software version 5.0.2 to yield a volume distribution for the scattering particles present in the solution. The results presented were representative of several sets of experiments.

1.3 Results from Thermodynamic Experiments
The Pairwise Interactions of IR485, Hormones and αCT Peptides ITC experiments investigated the pairwise interaction between selected combinations of IR485, ZFP-insulin, IGF-I, IR αCT peptide, IGF-1R αCT peptide and IR αCT.714A peptide. The results of the analyses are presented in Table 2. The mean dissociation constants ($K_d$) of the interaction between (i) IR αCT and IR485, (ii) IGF-1R αCT and IR 485, and (iii) IR αCT.714A and IR485 were determined to be 3.9±1.1 μM, 17.6±2.1 μM and 6.5±1.7 μM respectively. Representative ITC profiles for these measurements are presented in FIG. 2. The dissociation constant (IQ) for the interactions between (i) ZFP-insulin and the IR αCT peptide, (ii) IGF-I and the IGF-1R αCT peptide, (iii) ZFP-insulin and IR485 and (iv) IGF-I and IR485 was in all cases estimated to be weaker than 1 mM.

TABLE 2

ITC analysis of pairwise interactions of IR485, hormone and αCT peptides[a].

| Sample | [Sample] (μM) | Titrant | [Titrant] (μM) | $K_d$ (μM) |
|---|---|---|---|---|
| ZFP-insulin | 20 | IR-αCT | 200 | 1000 |
| IGF-IR | 20 | IGF1R-αCT | 200 | 1000 |
| IR485 | 5 | ZFP-insulin | 50 | 1000 |
| IR485 | 10 | IGF-IR | 100 | 1000 |
| IR485 | 10 | IR-αCT | 60 | 3.9 ± 1.1 |
| IR485 | 20 | IGF1R-αCT | 120-150[b] | 17.6 ± 2.1 |
| IR485 | 10 | IR-αCT.714A | 60 | 6.5 ± 1.7 |

[a]$K_d$ values are of the mean of three experiments with each set of experimental data being modeled as a single-site interaction between titrant and sample (see Materials and Methods). The error stated is the standard error of the mean. The relatively low value of the Wiseman parameter c coupled with the noise in the data precludes accurate determination of $\Delta H^0$ (and hence of $-T\Delta S^0$).
[b]Ranges are quoted for sample or titrant concentration where these vary across the three measurements.

The Interaction of Hormone with αCT Peptide Pre-Complexed IR485

ITC experiments investigated the interaction of ZFP-insulin and IGF-I with IR485 pre-complexed with a ten-fold molar ratio of either IR αCT or IGF-1R αCT peptide. Given that the αCT peptides displayed micromolar affinity for IR485 (see above), it was calculated that, at the concentrations of IR485 and αCT peptide employed in this set of experiments, >90% of the IR485 molecules within the ITC cell were in complex with αCT peptide prior to injection of hormone. The results of the ITC investigations are presented in Table 3 with representative ITC curves being presented in FIG. 3. The dissociation constant of ZFP-insulin with respect to IR485 in the presence of a 10-fold molar ratio of IR αCT peptide was 17±4 nM and in the presence of a 10-fold molar ratio of IGF-1R αCT peptide was 5.7±1.1 nM. In contrast, the dissociation constant of IGF-I with respect to IR485 in the presence of a 10-fold excess of IR αCT peptide was 490±75 nM and in the presence of a 10-fold excess of IGF-1R αCT peptide was 22±3 nM, with no correction being made for the incomplete saturation of IR485 with peptide prior to injection. The thermodynamic parameters presented in Table 3 show that in all four cases the binding of hormone to αCT peptide pre-complexed IR485 is enthalpically driven.

TABLE 3

Isothermal titration of ZFP-insulin and IGF-IR against IR485 pre-mixed with a 10-fold molar ratio of either IR or IGF-1R αCT peptide[a].

| Sample | [Sample] (μM) | Titrant | [Titrant] (μM) | $K_d$ (nM) | $\Delta H^0$ (kJ/mol) | $-T\Delta S^0$ (kJ/mol) |
|---|---|---|---|---|---|---|
| IR485 + (10 × IR-αCT) | 5 | ZFP-insulin | 50 | 17 ± 4 | −67 ± 1 | 22 ± 2 |

TABLE 3-continued

Isothermal titration of ZFP-insulin and IGF-IR against IR485
pre-mixed with a 10-fold molar ratio of either IR or IGF-1R αCT peptide[a].

| Sample | [Sample] (μM) | Titrant | [Titrant] (μM) | $K_d$ (nM) | $\Delta H^0$ (kJ/mol) | $-T\Delta S^0$ (kJ/mol) |
|---|---|---|---|---|---|---|
| IR485 + (10 × IGF1R-αCT) | 4-10[b] | ZFP-insulin | 32-60 | 5.7 ± 1.1 | −97 ± 2 | 50 ± 2 |
| IR485 + (10 × IR-αCT) | 5-10 | IGF-IR | 50-80 | 490 ± 75 | −89 ± 2 | 53 ± 2 |
| IR485 + (10 × IGF1R-αCT) | 4-5 | IGF-IR | 40-50 | 22 ± 3 | −101 ± 1 | 57 ± 1 |

[a] $K_d$, $\Delta H^0$ and $-T\Delta S^0$ values are of the mean of three experiments with each set of experimental data being modeled as a single-site interaction between titrant and sample (see Materials and Methods). The error stated is the standard error of the mean.
[b] Ranges are quoted for sample or titrant concentration where these vary across the three measurements.

The Interaction of Insulin Mimetic Peptides with IR485

ITC experiments investigated the interaction of the insulin mimetic peptides S519 (SEQ ID NO: 16), S519N20 (a Site 2 peptide, corresponding to the 20 N-terminal residues of 5519; SEQ ID NO: 17) and S519C16 (a Site 1 peptide, corresponding to the 16 C-terminal residues of S519; SEQ ID NO: 18) with IR485. The results are presented in Table 4, with representative ITC curves being presented in FIG. 4. S519 was found to bind IR485 with a dissociation constant of 11±3 nM, whilst S519C16 bound IR485 with somewhat higher affinity ($K_d$=2.6±0.7 nM). The binding of both S519 and S519C16 to IR485 appeared to be enthalpically driven. When IR485 was in the presence of a 10-fold molar ratio of IR αCT peptide, the dissociation constant of S519C16 increased to 16±6 nM. The dissociation constant for the interaction between S519N20 and IR485 was estimated to be weaker than 1 mM, with accurate determination of $K_d$ precluded at the concentrations of reactants employed.

TABLE 4

Isothermal titration of insulin mimetics peptides S519, S519N20 and S519C16 against IR485[a].

| Sample | [Sample] (μM) | Titrant | [Titrant] (μM) | $K_d$ (nM) | $\Delta H^0$ (kJ/mol) | $-T\Delta S^0$ (kJ/mol) |
|---|---|---|---|---|---|---|
| R485 | 4.5-5[b] | S519 | 40-50 | 11 ± 3 | −69 ± 6 | 24 ± 6 |
| R485 | 5 | S519C16 | 50 | 2.6 ± 0.7 | −61 ± 4 | 12 ± 4 |
| R485 + 10 × IR-αCT) | 3-5 | S519C16 | 45-50 | 16 ± 6 | −33 ± 2 | −11 ± 3 |
| R485 | 5 | S519N20 | 50 | 1 mM | [c] | |

[a] $K_d$, $\Delta H^0$ and $-T\Delta S^0$ values are of the mean of three experiments with each set of experimental data being modeled as a single-site interaction between titrant and sample (see Materials and Methods). The error stated is the standard error of the mean.
[b] Ranges are quoted for sample or titrant concentration where these vary across the three measurements.
[c] The affinity of interaction of S519N20 with IR485 is too weak to allow meaningful calculation of either $\Delta H^0$ or $-T\Delta S^0$.

The Multimeric State of IR485 in the Presence of IR αCT Peptide

The DLS-determined volume distribution of IR485 at 6 mg/ml (a concentration at which IR485 is overwhelmingly dimeric (Lou et al., 2006) showed a single broad peak centred at a particle diameter of 9.7 nm (FIG. 5a). The half-width of the peak was 3.1 nm and the assumption of a spherical particle lead to a calculated scattering particle molecular weight of 136 kDa, closely similar to the molecular weight of ~140 kDa estimated by size-exclusion chromatography. Instrumental limitations precluded DLS measurement of IR485 at concentrations at which IR485 was known to be overwhelmingly monomeric (i.e. at <0.025 mg/ml, (Lou et al., 2006). However, at 0.5 mg/ml, the DLS-determined volume distribution of IR485 showed a single broad peak at a particle diameter of 8.2 nm (FIG. 5b). The half-width of the peak was 2.2 nm and the assumption that the scattering arose from a single species of spherical scattering particle lead to a calculated molecular weight of 91 kDa, consistent with the solution being predominantly monomeric. Using this pair of observations as reference values, it was then observed that (i) an addition of a three-fold molar ratio of IR αCT peptide to a 6 mg/ml solution of IR485 resulted in a DLS-determined volume distribution which had a single peak centred at 8.6 nm (FIG. 5c), and (ii) an addition of a three-fold molar ratio of IR αCT peptide together with a 2-fold molar ratio of ZFP-insulin to a 6 mg/ml solution of IR485 resulted, in a volume distribution which had a single peak centred at 8.2 nm (FIG. 5d). The half-width of these latter two peaks was 2.4 nm and the calculated molecular weights of the scattering particles (again assuming a single species of spherical scatterers) was 102 kDa and 92 kDa respectively. These data implied that addition of either (i) IR αCT peptide or (ii) IR αCT peptide plus ZFP-insulin to a 6 mg/ml solution of IR485 resulted in a change in its hydrodynamic diameter consistent with the construct undergoing a transition from being overwhelmingly dimeric in solution to predominantly monomeric in solution.

Example 2

Solving the Crystal Structure of the C-Terminal Region of the α-Chain of IR 2.1 Introduction: Ambiguous Electron Density As described previously (WO 07/147,213), an area of strand-like ambiguous electron density was present near the L1-β2 face of IR. However, despite numerous different processing and refinement protocols, the density was impossible to interpret in terms of any peptide sequence. The data described in Example 1 above implied a surprising and previously unexpected sequence relationship between the S519C16 peptide (SEQ ID NO: 18) and the 'classical' αCT peptide region (residues 704-719; SEQ ID NO: 11) described previously in the literature (Kurose et al., 1994). X-ray data obtained in WO 07/147,213 were revisited and further reviewed with the possibility then in mind that the ambiguous electron density near the L1-β2 face of IR could have been due to the 'classical' αCT peptide region of the IR α-chain.

2.2 Protein Production, Crystallisation and Data Collection from IR Ectodomain Crystals Production of IR ectodomain protein, subsequent crystallization and data collection were performed as described previously (WO 07/147,213).

2.3 Diffraction Data Processing and Crystallographic Refinement

The diffraction images used were those used in the native structure determination of the human insulin receptor ectodomain homodimers ("Native 2" data set, see Table 3 of WO 07/147,213). The diffraction images were re-processed using XDS (version 10-September-2008; Kabsch, 1993), including reflections to a maximum resolution of 3.8 Å. Diffraction data processing statistics from XDS are shown in Table 5. About a 1 Å difference in the longest cell dimension was observed as compared to analysis previously with the D*trek (Pflugrath, 1999) program.

The receptor ectodomain monomer complexed with Fab 83-7 and Fab 83-14 (Protein Data Bank entry 2DTG, with minor prior in house improvement) was subjected to individual domain rigid body crystallographic refinement against the XDS-processed diffraction data set using PHENIX v1.3b (Adams et al., 2002). A total of fourteen rigid body domains were defined for this purpose (i) chain E and residues 4-191, (ii) chain E and residues 192-311, (iii) chain E and residue's 312-464, (iv) chain E and residues 465-594, (v) chain E and residues 595-817, (vi) chain E and residues 818-909, (vii) chain A and residues 1-112, (viii) chain B and residues 1-109, (ix) chain A and residues 113-220, (x) chain B and residues 110-219, (xi) chain C and residues 1-109, (xii) chain C and residues 110-207, (xiii) chain D and residues 1-106, (xiv) chain D and residues 107-214). Rigid body refinement was then followed by atomic coordinate refinement and finally by TLS (translation, libration and screw-rotation displacement) refinement, using default protocols within PHENIX. A $\sigma_A$-weighted $2F_o$-$F_c$ difference electron map was then calculated using structure factors whose amplitudes had been artificially inflated by the application of a B value (−153 Å$^2$) equal to the negative of that determined by a Wilson plot (Brünger et al., 2009). The map was then visually inspected using O v12.0 (Jones, 2004). At this stage the segment of electron density previously discerned on the L1-β2 face of IR (WO 07/147, 213) had a surprisingly clear helical conformation with sufficient variation in side chain electron density to suggest that sequence assignment was possible (see below). O was then used for all subsequent model building of the IR segment 693-710, with model building being iterated with crystallographic refinement within PHENIX. Final crystallographic refinement statistics are shown in Table 5.

2.4 Assigning Structure to the C-Terminal Region of the IR α-Chain

Following the refinement protocol detailed above, sequence assignment to the C-terminal region of the IR α-chain was possible and based on the following observations (i) the segment Glu698 to Tyr708 was the only region of the insert domain predicted to have helix-forming propensity (Ward and Lawrence, 2009), (ii) inspection of the density at the side-chain positions i, i+4 and i+7 showed that they likely arose from three large (most likely aromatic) residues, that these could in all likelihood be used to define the sequence register, and that the discerned helix would then span residues i−8 to i+9, (iii) the direction of the polypeptide chain within the helix was readily apparent from helical "tree" averaging of the difference electron density (Jones, 2004), and (iv) the only possible assignment of the sequence, to the i, i+4, i+7 all-aromatic motif of (ii) above was to associate these residues with Phe701, Phe705 and Tyr708, respectively.

TABLE 5

Data processing and crystallographic refinement statistics from IR ectodomain crystal IR IRAβ data processed using XDS.

| Data processing | |
| --- | --- |
| Space group | C222$_1$ |
| Cell dimensions | |
| a, b, c (Å) | 123.03, 318.65, 204.64 |
| Resolution (Å) | 30.64 (3.80)* |
| R$_{sym}$ | 14.6 (198.9) |
| I/σI | 0.96 |
| Completeness (%) | 93.8 (93.4) |
| Redundancy | 5.47 (5.35) |
| Refinement | |
| Resolution (Å) | 30.64 – 3.80 |
| No. reflections | 39268 |
| R$_{work}$/R$_{free}$ | 0.225/0.289 |
| No. atoms | |
| Protein | 13041 |
| B-factors | |
| Protein (Å$^2$) | 180.68 |
| R.m.s. deviations. | |
| Bond lengths (Å) | 0.011 |
| Bond angles (°) | 1.558 |

*Values in parentheses are for highest-resolution shell. Data were collected from a single crystal.

The observed helical region of density spanned IR residues 693 to 710 (SEQ ID NO: 13; FIG. 6). The direction of the polypeptide was consistent with having the inter-monomer disulphide bond-forming triplet Cys682/Cys683/Cys685 (Sparrow et al., 1997) in close proximity to the ectodomain two-fold axis (McKern et al., 2006). Subsequent model-building of insulin receptor residues 693-710 (SEQ ID NO: 13) into the difference electron density further supported the correctness of the sequence register assignment by virtue of the shape and electrostatic complementarity of the packing at the interface between L1 and the helical segment.

The side-chains of Phe701 and Phe705 pack adjacent to each other into a hydrophobic pocket formed by the side-chains of the L1 residues Phe64, Phe88, Phe96, Tyr91 and Arg 118 (FIG. 6b). The side-chain of Tyr708 is packed approximately parallel to the surface and interacts with the L1 residues Leu62, Gln34 and Phe64. The side-chains of the residue pair Glu698 and Arg702 lie in close proximity and are juxtaposed against the side chains of the L1 residue pair Arg118 and Asp 120 respectively, the four side chains forming a symmetric charge-compensating cluster. The final interaction between the helix and the surface of the central b-sheet of L1 arises from an interaction between the side chain of Leu709 with the side chains of the L1 residues Leu37 and Phe64. On the opposite surface of the helix side chains of the residue pair Lys703 and Asp707 are in proximity to each other and also likely charge compensate. Further crystallographic refinement of the (IR+Fab 83-7+Fab 83-14) structure, now inclusive of IR residues 693-710, lead to a reduction of 0.5% in the free R-factor. The shape complementarity (Lawrence and Colman, 1993) of the interface between the insulin receptor residues 693-710 and the L1 domain of the receptor, computed after crystallographic refinement, is high (0.72). Taken together, these results gave overwhelming support to the correctness of the assignment of sequence to the helical density segment.

The structure provided herein (Appendix I) enables, for the first time, a view of the intact low affinity insulin receptor binding site that includes the critically-important C-terminal region of the receptor α-chain (SEQ ID NO: 13). The atomic coordinates of IR+Fab 83-7+Fab 83-14 inclusive of the helical segment are now included in Appendix I and are depicted in FIG. 6. The modelled helical segment of the IR α-chain (residues 693-710, herein termed. 'the C-terminal region of the α-chain of IR'; LKELEESSFRKTFEDYLH; SEQ ID NO: 13) surprisingly encompasses residues N-terminal of the "classical" αCT peptide of IR (residues 704-719; TFEDYLHNVVFVPRPS; SEQ ID NO: 11) described previously in the literature (Kurose et al., 1994; FIG. 6c). The original demarcation of this segment arose from a tryptic digest aimed at isolating receptor segments that were experimentally cross-linked to bound insulin. Tryptic cleavage at Lys703 resulted in the isolation of the segment 704-719 crosslinked to insulin. The involvement of residues immediately N-terminal of 704 in both the formation of the low affinity insulin binding site and in attachment of α-chain C-terminus to the first three domains of the receptor had not been contemplated previously.

Example 3

Molecular Modelling 3.1 Introduction

There is a high level of sequence identity between, on the one hand, the L1 domains of IGF-1R and IR, and, on the other hand, between the C-terminal regions of the α-chain of IGF-1R and IR (FIG. 1 and FIG. 6c). Accordingly, models of IR in complex with S519C16 and the IGF-1R α-chain residues 681-697, respectively, were constructed using the MODELLER program (Sali and Blundell, 1993) with the crystallographic structure of IR ectodomain presented in the main text as a template. Models of the ectodomain of IGF-1R in complex, respectively, with the IGF-1R α-chain residues 681-697 (SEQ ID NO: 15), S519C16 (SEQ ID NO: 18) and the IR α-chain residues 693-710 (SEQ ID NO: 13) were constructed employing the crystal structure of the first three domains of IGF-1R (Garrett et al., 1998), the structure of the IR ectodomain presented here and the known sequence relationship between IR and IGF-1R (Adams et al., 2000).

3.2 Materials and Methods for Modelling

Twenty-five instances of each model were prepared and the structure with lowest DOPE score (Eramian et al., 2006) selected for further molecular dynamics (MD) simulation. The L1-domains of IR and IGF-1R, residues Pro4-Gln189 and residues Glu1-Gln189, respectively, in complex with the various peptides were excised from the full-length models prepared by MODELLER for use in the MD calculations. MD simulations were performed using the GROMACS v4.0 suite (van der Spoel et al., 2005) with the OPLS-aa force field (Jorgensen and Tirado-Rives, 1988). The proteins were solvated in a box of water and the total charge of the system neutralized by replacing water molecules with sodium ions. The LINCS algorithm was used to constrain bond lengths (Hess et al., 1977). Protein and solvent (including ions) were coupled separately to a thermal bath at 300 K using velocity resealing (Bussi et al., 2007) applied with a coupling time of 0.1 ps. All simulations were performed with a single non-bonded cutoff of 10 Å, applying a neighbour-list update frequency of 10 steps (20 fs). The particle mesh Ewald method was applied to deal with long-range electrostatics with a grid width of 1.2 Å and fourth-order spline interpolation. All simulations consisted of an initial minimization to remove close contacts, followed by 100 ps of positional restrained MD to equilibrate the water molecules with the protein fixed. The time step used in all the simulations was 2 fs. MD simulations for each system were run for a total length of 2.0 ns.

3.3 Molecular Models

The following models were created using MODELLER and subjected to MD simulations as described above:

the C-terminal region of IR α-chain (SEQ ID NO: 13) bound to the L1 domain of IGF-1R (Appendix II; FIG. 7), the C-terminal region of IGF-1R α-chain (SEQ ID NO: 15) bound to the L1 domain of IR (Appendix III; FIG. 8), the C-terminal region of IGF-1R α-chain (SEQ ID NO: 15) bound to the L1 domain of IGF-1R (Appendix IV; FIG. 9), S519C16 mimetic peptide (SEQ ID NO: 18) bound to the L1 domain of IR (Appendix V; FIG. 10), and S519C16 mimetic peptide (SEQ ID NO: 18) bound to the L1 domain of IGF-1R (Appendix VI; FIG. 11).

The above models are presented schematically in FIGS. 7 to 11, with coordinates in Appendixes II to VI, respectively. These models define a common binding surface on IR and IGF-1R capable of binding the C-terminal region of the α-chain of the receptors. The following interactions were observed:

(i) IGF-1R/IR α-chain residues 693-710 (FIG. 7): This interaction is characterized by several polar and ionic interactions—Y83 of the receptor hydrogen bonds the hydroxyl side-chains of S700 and T704 of the ligand, and E698 and R702 of the ligand form salt bridges with R112 and E114 of the receptor, respectively. Hydrophobic residues on the ligand pack into a hydrophobic pocket on the receptor formed by in part by L32, L33, L56, F58, F82, Y83, Y85, V88 and F90.

(ii) IR/IGF-1R α-chain residues 681-697 (FIG. 8): The complex between IR and the IGF-1R α-chain (residues 681-697) consists of charged interactions between R118 and E120 of IR, and E685 and Y688 of the peptide, respectively—the latter of these interactions can be mediated by a water molecule. There are a large number of hydrophobic residues on IR that contact the peptide, formed in part by L36, L37, L62, F64, F88, F89, Y91, V94 and F96.

(iii) IGF-1R/IGF-1R α-chain residues 681-697 (FIG. 9): This interaction is characterized by a salt bridge between R112 of the receptor and E685 of the peptide. Additionally, the hydroxy group on the side-chain of Y688 in hydrogen bonded to a water molecule (not shown) that is itself hydrogen bonded to E114 of the receptor. The hydrophobic resides Y688, F192, F195 and L196 pack into the hydrophobic pocket on the surface of the receptor formed in part by the side-chains of L32, L56, F58, F82, Y83, Y85, V88 and F90.

(iv) IR/S519C16 (FIG. 10): Throughout the MD simulation of the complex between IR (L1 domain) and the S519C16 peptide several hydrogen-bond interactions are observed—between R119 of IR and D4 of the peptide, between E120 of IR and Y8 of the peptide, and between Q14 of the peptide with both residues R14 and Q34 of IR. The interaction between receptor and peptide involves the aromatic side-chains of several residues—F7 and F11 of the peptide bind a pocket on the surface of IR flanked by the residues L62, F64, F88, F89, Y91 and F96. Additionally, L15 of the peptide packs against the hydrophobic side-chains of L37 and F64.

(v) IGF-1R/S519C16 (FIG. 11): D4 and Y8 of the peptide hydrogen bonds R112 and E114 of the receptor, respectively. The aromatic side-chains of F7 and F11 of the peptide bind the hydrophobic pocket on the receptor formed by L56, F58, F82, Y83, V88 and F90. W10 of the peptide can conceivably contact the hydrophobic side-chains of L32 and F82, increasing its affinity.

The models presented herein can now be used to improve the insulin mimetic peptides developed by Schäffer and co-workers (Schäffer et al., 2003). Isothermal titration calorimetry experiments (see Example 1 above) indicated that a prototypical Site 1 mimetic peptide S519C16 competes with the IR C-terminal peptide 704-719 in binding to a construct consisting of the first three domains of the insulin receptor. The two major residues involved in the interaction between the C-terminal segment of the insulin receptor α-chain and the L1 domain (viz. Phe701 and Phe705) are conserved in S519C16 (FIG. 3). Of the remaining residues involved in the interaction between the C-terminus of the α-chain and L1, Tyr708 is replaced with an asparagine residue in S519C16, Glu698 is either conserved or replaced by an aspartate residue, Arg702 is replaced by a tyrosine residue and Leu709 is conserved. The two phenylalanine residues form part of the motif FYXWF (SEQ ID NO: 19) that characterizes the Site 1 mimetic peptides (Schäffer et al., 2003). Modelling undertaken with MODELLER and subsequent MD showed that it is possible to dock the S519C16 peptide onto the L1 surfaces of IR and IGF-1R in a way analogous to the docking of cognate peptides (see FIGS. 6-11).

Example 4

Binding of Mutant αCT Peptides to an Insulin Mini-Receptor (IR485 Construct)

4.1 Introduction

Insulin-mimetic peptides have been discovered by phage display technology and classified as "Site" 1, 2 or 3 on the basis of competition of binding to insulin receptor (Pillutla et al., 2002). The affinity-matured Site 1 peptides are characterized by a FYXWF motif (SEQ ID NO: 19) (Pillutla et al., 2002); selected Site 1 and 2 peptides have been covalently tethered to yield agonists with up to picomolar affinity for insulin receptor (Schäffer et al., 2003). A sequence relationship has been shown (see FIG. 6c) between the αCT region and the prototypic Site 1 mimetic peptide that places the αCT region residues Phe701 and Phe705 in respective alignment with the two flanking phenylalanine residues in the FYXWF motif. This relationship was used to explain the competitive binding of the αCT peptide and the prototypic Site 1 mimetic peptide to the insulin mini-receptor IR485, a construct which consists of the receptor L1-CR-L2 domains only. If this relationship was correct, then mutation of Arg702 and/or Thr704 within the αCT segment to either tyrosine or tryptophan would lead to significantly higher affinity of the segment for the insulin mini-receptor. It would also then be possible to model these substitutions directly onto the structure reported here. These hypotheses were tested as follows.

4.2 Materials and Methods for Thermodynamic Experiments

Biotinylated αCT peptides at >75% purity spanning residues 698-719 of the insulin receptor were obtained from Genscript Inc. (USA). The insulin mini-receptor IR485 construct was produced and purified as previously described (Lou et al., 2006), omitting the final ion-exchange chromatography step. Isothermal titration calorimetry (ITC) experiments were performed using a VP-ITC isothermal titration calorimeter (MicroCal Inc., USA) with the calorimeter cell held at about 25° C. The ITC cell contained insulin mini-receptor IR485 prepared at about 10 μM concentration in Tris-buffered saline plus azide (TBSA; about 24.8 mM Tris-HCl (pH 8.0), 137 mM NaCl, 2.7 mM KCl, and 0.02% sodium azide), and the syringe contained the peptide prepared at about 60 μM concentration in TBSA. All samples were degassed prior to injection or placement into the cell, and the instrument was temperature equilibrated prior to the start of the injections.

In all experiments the volume of the insulin mini-receptor IR485 sample placed in the cell was about 1.4 ml and the titrant was injected in about 7 μl volumes over 14 s at 3 min intervals, with the total number of injections being 40. The sample contents were stirred at a speed of about 310 rpm over the duration of the titration. All titrants were first injected into a solution of TBSA alone in order ascertain the heat of dilution, which was then subtracted from the data of interest as appropriate. Each experiment was performed three times, except for that employing the native peptide, which was performed twice. Data were analyzed using the instrument's software incorporated within the Origin 7 software (OriginLab, USA) and in all cases fitted as a single-site interaction using the methodologies outlined in the instrument's manual.

4.3 Results from Thermodynamic Experiments

Sample individual titration curves are provided in FIG. 12. Table 6 below presents ITC-derived dissociation constants and thermodynamic parameters for a set of mutant αCT peptides titrated against the insulin mini-receptor IR485.

TABLE 6

Derived thermodynamic parameters for the titration against IR485 of the N-terminally biotinylated IR peptide 698-719 containing the following respective mutations: wild-type, T704Y, R702W, R702Y, T704W and R702Y/T704W.

| Titrant peptide* | $K_d$ peptide (nM) | $\Delta H^0$ (kJ mol$^{-1}$) | $T\Delta S^0$ (kJ mol$^{-1}$) | $\Delta G^0$ (kJ mol$^{-1}$) |
|---|---|---|---|---|
| wt | 1340 ± 230† | −48 ± 1 | −14 ± 1 | −33.5 ± 0.4 |
| T704Y | 740 ± 210 | −46 ± 9 | −11 ± 9 | −35 ± 0.7 |
| R702W | 309 ± 36 | −35 ± 5 | −3 ± 5 | −37.2 ± 0.3 |
| R702Y | 249 ± 3 | −50 ± 3 | −12 ± 2 | −37.67 ± 0.03 |
| T704W | 201 ± 16 | −26 ± 2 | 11 ± 2 | −38.2 ± 0.2 |
| R702Y/T704W | 18 ± 3 | −49 ± 2 | −5 ± 2 | −44.2 ± 0.4 |

*αCT peptides span residues 698-719 and have a biotin moiety attached at the N-terminus.
†Error estimates are the standard error of the mean.

Progressive inclusion of aromatic residues at positions 702 and 704 is seen to result in an up to 100-fold increase in affinity, supporting the view that there is a structural relationship between the Site-1 mimetic peptides and the native αCT segment. The docking of the single- and double-mutant αCT peptides to the surface of the L1 domain was investigated by molecular dynamics simulation using the GROMACS v4.0 suite (van der Spoel et al., 2005) with the OPLS-aa force field (Jorgensen et al., 1988) and revealed that the aromatic side chains of mutant αCT residues Trp702 and Tyr704 are likely to interact with the surface of the L1 domain and enhance the affinity of the interaction. At position 702 the aromatic side chain is docked into a pocket formed by the Phe96 and the alkyl portion of L1 side-chain Lys 121; the hydroxyl group of a variant tyrosine residue can in addition form a hydrogen bond with the Lys121 ε-amino group. At position 704 the aromatic side chain of the variants is docked against L1 side chains Phe88 and Phe89.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

This application claims priority from U.S. 61/214,472 filed 22 Apr. 2009, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References

Adams et al. (2000) Cell. Mol. Life. Sci., 57, 1050-1093.
Adams et al. (2002) Acta Cryst. D58, 1948-54.
Apfel (1999) Am. J. Med., 107, 34S-42S.
Auer (1998) Neurology, 51, S39-S43.
Ausubel et al. (1999) Short Protocols in Molecular Biology, 4$^{th}$ Ed, John Wiley & Sons, Inc.; and the full version entitled Current Protocols in Molecular Biology.
Bailyes et al. (1997) Biochem. J., 327, 209-215.
Bartlett et al. (1989) Royal Chem. Soc., 78, 182-196.
Bentley (1997) Methods Enzymol., 276, 611-619.
Binz et al. (2005) Nature Biotech., 23, 1257-1268.
Blondelle and Houghten (1996) Trends Biotechnol., 14, 60-65.
Bohm and Stahl (1999) M. Med. Chem. Res., 9, 445.
Brooks et al. (1983) Comp. Chem., 4, 187-217.
Brünger et al. (1998) Acta Cryst. D54, 905-921.
Brünger (1997) Methods Enzymol., 276, 558-580.
Brünger et al. (2009) Acta Cryst., D65, 128-33.
Bruns et al. (1999) J Mol Biol., 288, 427-439.
Bussi et al. (2007) M. J. Chem. Phys., 126, 14101.
Buttel et al. (1999) Immunol. Cell Biol., 77, 256-262.
Carell et al. (1994a) Angew. Chem. Int. Ed. Engl., 33, 2059.
Carell et al. (1994b) Angew. Chem. Int. Ed. Engl., 33, 2061.
Cho et al. (1993) Science, 261, 1303.
Chow et al. (1998) Biol. Chem., 273, 4672-4680.
Clarke et al. (2000) Cancer Res., 60, 4804-4811.
Cohen et al. (1990) J. Med. Chem., 33, 883-894.
Cole et al. (2005) in "Virtual Screening in Drug Discovery (Eds. B. Shoichet, J. Alvarez)", Taylor & Francis CRC Press, Florida, USA.
Cull et al. (1992) Proc. Natl. Acad. Sci. USA, 89, 1865-1869.
Cwirla et al. (1990) Proc. Natl. Acad. Sci. USA, 97, 6378-6382.
Danial et al. (2008) Nat. Med. 14, 144-153.
Davis et al. (2006) Chem. Soc. Rev. 36, 326-334.
Day and Caflisch (2008) J. Chem. Inform. Model. 48, 679-90.
Degterev et al. (2001) Nat. Cell. Biol. 3, 173-182.
De Meyts (1994) Diabetologia, 37, S135-S148.
De Meyts and Whittaker (2002) Nat. Rev. Drug Discov., 1, 769-783.
De Meyts (2004) Bioessays, 26, 1351-1362.
Denley et al. (2003) Horm. Metab. Res., 35, 778-785.
Denley et al. (2004) Mol. Endocrinol., 18, 2502-2512.
Devlin (1990) Science, 249, 404-406.
DeWitt et al. (1993) Proc. Natl. Acad. Sci. USA, 90, 6909.
Eramian et al. (2006) Protein Sci. 15, 1653-66.
Erb et al. (1994) Proc. Natl. Acad. Sci. USA, 91, 11422.
Ernst et al. (2000) J. Magn. Reson. Imaging, 12, 859-865.
Ewing et al. (2001) J. Comput-Aid. Mol. Design, 15, 411.
Felici (1991) J. Mol. Biol., 222, 301-310.
Fodor (1993) Nature, 364, 555-556.
Friesner et al. (2004) J. Med. Chem. 47, 1739-1749.
Garrett et al. (1998) Nature, 394, 395-399.
Gallop et al. (1994). J. Med. Chem., 37, 1233.
Goodford (1985) J. Med. Chem., 28, 849-857 (1985).
Goodsell and Olsen (1990) Proteins: Struct. Funct. Genet., 8, 195-202.
Guida (1994) Curr. Opin. Struct. Biol., 4, 777-781.
Hess et al. (1977) Comp. Chem. 18, 1463-1472.
Hewish et al. (2009) Recent Patents Anticancer Drug Discov, 4, 54-72.
Houghten et al. (1991) Nature, 354, 84-86.
Houghten (1992) Biotechniques, 13, 412-421.
Jones et al. (1991) Acta Cryst. A47, 110-119.
Jones (2004) Acta Cryst. D60, 2115-25.
Jorgensen and Tirado-Rives (1988) Am. Chem. Soc., 110, 1657-1666
Kabsch (1993) J. Appl. Cryst., 26, 795-800.
Kiselyov et al. (2009) Mol. Sys. Biol., 5, 243.
Kitamura et al. (2003) Annu. Rev. Physiol., 65, 313-332.
Kristensen et al. (2002) J. Biol. Chem., 277, 18340-18345.
Kuntz et al. (1982) J. Mol. Biol., 161, 269-288.
Kurose et al. (1994) J. Biol. Chem., 269, 29190-29197.
Lam et al. (1991) Nature, 354, 82-84.
Lam (1997) Anticancer Drug Des., 12, 145.
Lawrence and Colman (1993) J. Mol. Biol., 234, 946-950.
Lawrence et al. (2007) Curr. Opin. Struct. Biol., 17, 699-705.
Liu et al. (1993) Cell, 75, 59-72.
Lou et al. (2006) Proc. Natl. Acad. Sci. USA 103, 12429-12434.
Luo et al. (1999) Science, 285, 1077-1080.
Marsh et al. (1995) J. Cell Biol., 130, 1081-1091.
Martin (1992) J. Med. Chem., 35, 2145-2154.
McCoy (2007) Act Cryst D63, 32-41.
McKern et al. (2006) Nature, 443, 218-221.
Menting et al. (2009) Biochemistry (submitted).
Miranker and Karplus (1991) Proteins: Struct. Funct. Genet., 11, 29-34.
Moody et al. (1974) Horm. Metab. Res., 6, 12-16.
Morton and Myszka (1998) Methods Enzymol., 295, 268-294.
Navaza and Saludjian (1997) Methods Enzymol., 276, 581-594.
Navia and Murcko (1992) Curr. Opin. Struct. Biol., 2, 202-210.
Nice and Catimel (1999) Bioessays, 21, 339-352.
Olefsky (1978) Biochem. J., 172, 137-145.
Ottensmeyer et al. (2000) Biochemistry, 39, 12103-12112.
Ottensmeyer et al. (2001) Biochemistry, 40, 6988-6988.
Pflugrath (1999) Acta Cryst. D55, 1718-1725.
Pillutla et al. (2002) J. Biol. Chem., 277, 22590-22594.
Rarey et al. (1996) J. Mol. Biol., 261, 470.

Robinson and James (1992) Am. J. Physiol., 263, E383-E393.

Rossmann, ed. (1972) The Molecular Replacement Method, Int. Sci. Rev. Ser., No. 13, Gordon & Breach, New York.

Sali and Blundell (1993) J. Mol. Biol., 234, 779-815.

Sambrook et al. (2001) Molecular Cloning: A Laboratory Manual, 3$^{rd}$ ed. Cold Spring Harbor Laboratory Press, Cold Spring Harbor, N.Y.

Schäffer (1994) Eur. J. Biochem., 221, 1127-1132.

Schäffer et al. (2003) Proc. Natl. Acad. Sci. USA, 100, 4435-4439.

Scott and Smith (1990) Science, 249, 386-390.

Silverman et al. (2005) Nature Biotech., 23, 1556-1561.

Smith et al. (1999) Nat. Med., 5, 1390-1395.

Songyang et al. (1993) Cell, 72, 767-778.

Sparrow et al. (1997) J. Biol. Chem., 272, 29460-29467.

Stumpp et al. (2007) Curr. Opin. Drug Discov. Develop., 10, 153-159.

Surinya et al. (2008) J. Biol. Chem. 283, 5355-5363.

Svenson et al. (2009) Mol. Pharm., published online 2 Apr. 2009 (DOI: 10.1021/mp 900057k).

Tong and Rossmann, (1997) Methods Enzymol., 276, 594-611.

Totrov and Abagyan (2008) Curr. Opin. Struct. Biol., 18, 178-184.

Tulloch et al. (1999) J. Struct. Biol., 125, 11-18.

Ullrich et al. (1985) Nature, 313, 756-761.

Ullrich et al. (1986) EMBO J., 5, 2503-2512.

Ulrich (2006) Handb Exp Pharmacol., 173, 305-326.

van der Spoel et al. (2005) J. Comp. Chem., 26, 1701-1718.

Wada et al. (2005) J Pharmacol Sci., 99, 128-143.

Ward et al. (2003) Insulin-like growth factors (LeRoith D, Zumkeller, W. & Baxter R. (eds), Eurekah.com and Kluwer Academic/Plenum Publishers, 1-21.

Ward and Lawrence (2009) BioEssays, 31, 422-434.

Weiner et al. (1984) J. Am. Chem. Soc., 106, 765-784.

Yin et al. (2005) Angew. Chem. Int. Ed. Engl., 44, 2704-2707.

Yip et al. (1988) Biochem. Biophys. Res. Commun., 157, 321-329.

Yip and Ottensmeyer (2003) J. Biol. Chem., 278, 27329-27332.

Zuckermann et al. (1994) J. Med. Chem., 37, 2678.

Lengthy table referenced here
US08666718-20140304-T00001
Please refer to the end of the specification for access instructions.

Lengthy table referenced here
US08666718-20140304-T00002
Please refer to the end of the specification for access instructions.

Lengthy table referenced here
US08666718-20140304-T00003
Please refer to the end of the specification for access instructions.

Lengthy table referenced here
US08666718-20140304-T00004
Please refer to the end of the specification for access instructions.

Lengthy table referenced here
US08666718-20140304-T00005
Please refer to the end of the specification for access instructions.

Lengthy table referenced here
US08666718-20140304-T00006
Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08666718B2). An electronic copy of the table will also be available from the USPTO upon request and payment of the fee set forth in 37 CFR 1.19(b)(3).

The invention claimed is:

1. A computer-assisted method of identifying, designing or screening for a compound that potentially interacts with insulin receptor (IR), which method comprises (a) fitting the structure of a candidate compound to the structure of the low affinity insulin binding site of the IR, the structure having atomic coordinates shown in one or more of Appendixes I, III, and V, or a subset of atomic coordinates at least representing the C-terminal region of the α-chain of IR; and (b) detecting compounds having an energetically favoured interaction with a structure defined by the atomic coordinates of amino acids 693-710 of the IR α-chain (SEQ ID NO: 13).

2. The method according to claim 1, further comprising synthesising or obtaining an identified or designed candidate compound and determining the ability of the candidate compound to interact with IR.

3. The method according to claim 1, wherein the atomic coordinates of step (a) define one or more regions of the low affinity binding site of IR for insulin comprising the C-terminal region of the α-chain of IR.

4. The method according to claim 1, wherein the atomic coordinates of step (a) defining the low affinity insulin binding site of IR further comprise the leucine-rich repeat 1 (L1) domain and/or the cysteine-rich (CR) domain of the IR ectodomain.

5. The method according to claim 4, wherein the atomic coordinates of step (a) define portions of the molecular surface of the central β-sheet of the L1 domain and portions of the molecular surface of the second leucine-rich repeat (LRR) which contain Phe39 and/or the loop in the fourth LRR rung of the L1 domain.

6. The method according to claim 4, wherein the atomic coordinates of step (a) define module 6 of the CR domain of IR.

7. The method according to claim 3, wherein the atomic coordinates of step (a) further define one or more amino acid sequences selected from IR amino acid residues 1-156, 157-310, 594 and 794.

8. The method according to claim 7, wherein the one or more amino acids selected from IR amino acid residues 1-156 comprise at least one amino acid selected from Arg14, Asn15, Gln34, Leu36, Leu37, Phe39, Pro43, Phe46, Leu62, Phe64, Leu87, Phe88, Phe89, Asn90, Phe96, Glu97, Arg118, Glu120 and His 144.

9. The method according to claim 7, wherein the one or more amino acids selected from IR amino acid residues 157-310 comprise at least one of the amino acid sequences selected from 192-310, 227-303 and 259-284.

10. The method according to claim 2 wherein the a candidate compound for interacting with IR is chemically modified as result of structure-based evaluation.

11. The method according to claim 10, wherein the chemical modification is designed to either:
(i) reduce the potential for the candidate compound to bind to IR whilst maintaining binding to IGF-1R; or
(ii) reduce the potential for the candidate compound to bind to IGF-1R, whilst maintaining binding to IR.

* * * * *